(12) United States Patent
Isobe et al.

(10) Patent No.: US 8,511,195 B2
(45) Date of Patent: Aug. 20, 2013

(54) REMOTE-CONTROLLED ACTUATOR

(75) Inventors: Hiroshi Isobe, Shizuoka (JP);
Takayoshi Ozaki, Shizuoka (JP);
Yoshitaka Nagano, Shizuoka (JP);
Yukihiro Nishio, Shizuoka (JP)

(73) Assignee: NTN Corporation, Osaka (JP)

( * ) Notice: Subject to any disclaimer, the term of this patent is extended or adjusted under 35 U.S.C. 154(b) by 105 days.

(21) Appl. No.: 13/080,806

(22) Filed: Apr. 6, 2011

(65) Prior Publication Data

US 2011/0179894 A1 Jul. 28, 2011

Related U.S. Application Data

(63) Continuation of application No. PCT/JP2009/005106, filed on Oct. 2, 2009.

(30) Foreign Application Priority Data

| Oct. 8, 2008 | (JP) | 2008-261339 |
| Oct. 10, 2008 | (JP) | 2008-264437 |
| Oct. 10, 2008 | (JP) | 2008-264438 |
| Jan. 23, 2009 | (JP) | 2009-013009 |

(51) Int. Cl.
*B25J 17/00* (2006.01)
*B25J 17/02* (2006.01)
*B25J 18/00* (2006.01)
*A61B 17/14* (2006.01)
*A61B 17/32* (2006.01)

(52) U.S. Cl.
USPC .................. 74/490.01; 606/180; 901/28

(58) Field of Classification Search
USPC ............ 901/14, 15, 16, 19, 27, 28; 606/180; 74/490.1, 490.04, 500.5–503; 81/57.43, 81/57.27; 173/39
See application file for complete search history.

(56) References Cited

U.S. PATENT DOCUMENTS 2,487,203 A * 11/1949 Wilber .......................... 464/97
4,265,231 A   5/1981 Scheller, Jr. et al.
(Continued)

FOREIGN PATENT DOCUMENTS

JP 58-080213 5/1983
JP 06-011936 2/1994
(Continued)

OTHER PUBLICATIONS

Partial translation of Korean Patent Application No. 10-2011-7007861 First Office Action dated Oct. 12, 2012 (7 pages).

*Primary Examiner* — Troy Chambers
*Assistant Examiner* — Michael Gonzalez
(74) *Attorney, Agent, or Firm* — Pierce Atwood, LLP; Kevin M. Farrell, Esq.; Robert L. Hover, Esq.

(57) ABSTRACT

A remote controlled actuator includes a spindle guide section of an elongated configuration, a distal end member fitted to a tip end of the spindle guide section for alteration in attitude, and a drive unit housing to which a base end of the spindle guide section is connected. The distal end member rotatably supports a spindle then holding a tool. The spindle guide section includes a hollow outer shell pipe, a rotary shaft and a guide pipe, and an attitude altering member for altering an attitude of the distal end member is inserted within the guide pipe. A hollow of the outer shell pipe includes a round hole portion at a center and a grooved portion depressed radially outwardly from the round hole portion. The rotary shaft is arranged within the round hole portion whereas the guide pipe is arranged within the grooved portion.

15 Claims, 37 Drawing Sheets

(56) References Cited

U.S. PATENT DOCUMENTS

| | | | |
|---|---|---|---|
| 4,466,429 A | | 8/1984 | Loscher et al. |
| 4,483,562 A | * | 11/1984 | Schoolman .................... 294/104 |
| 4,751,821 A | * | 6/1988 | Birchard .......................... 60/698 |
| 5,002,543 A | * | 3/1991 | Bradshaw et al. ............... 606/62 |
| 5,405,344 A | | 4/1995 | Williamson et al. |
| 5,431,323 A | * | 7/1995 | Smith et al. ................. 227/177.1 |
| 5,702,408 A | * | 12/1997 | Wales et al. .................... 606/139 |
| 7,842,028 B2 | * | 11/2010 | Lee ................................... 606/1 |
| 2004/0138529 A1 | * | 7/2004 | Wiltshire et al. .............. 600/144 |
| 2007/0265653 A1 | | 11/2007 | Suzuki |

FOREIGN PATENT DOCUMENTS

| | | |
|---|---|---|
| JP | 07-163574 A | 6/1995 |
| JP | 2001-017446 A | 1/2001 |
| JP | 2001017446 A | 1/2001 |
| JP | 2005-528159 A | 9/2005 |
| JP | 2005528159 A | 9/2005 |
| JP | 2007-068636 A | 3/2007 |
| JP | 2007-301149 A | 11/2007 |
| WO | 03/101308 A1 | 12/2003 |
| WO | 2007143440 A2 | 12/2007 |
| WO | 2008038307 A1 | 4/2008 |

* cited by examiner

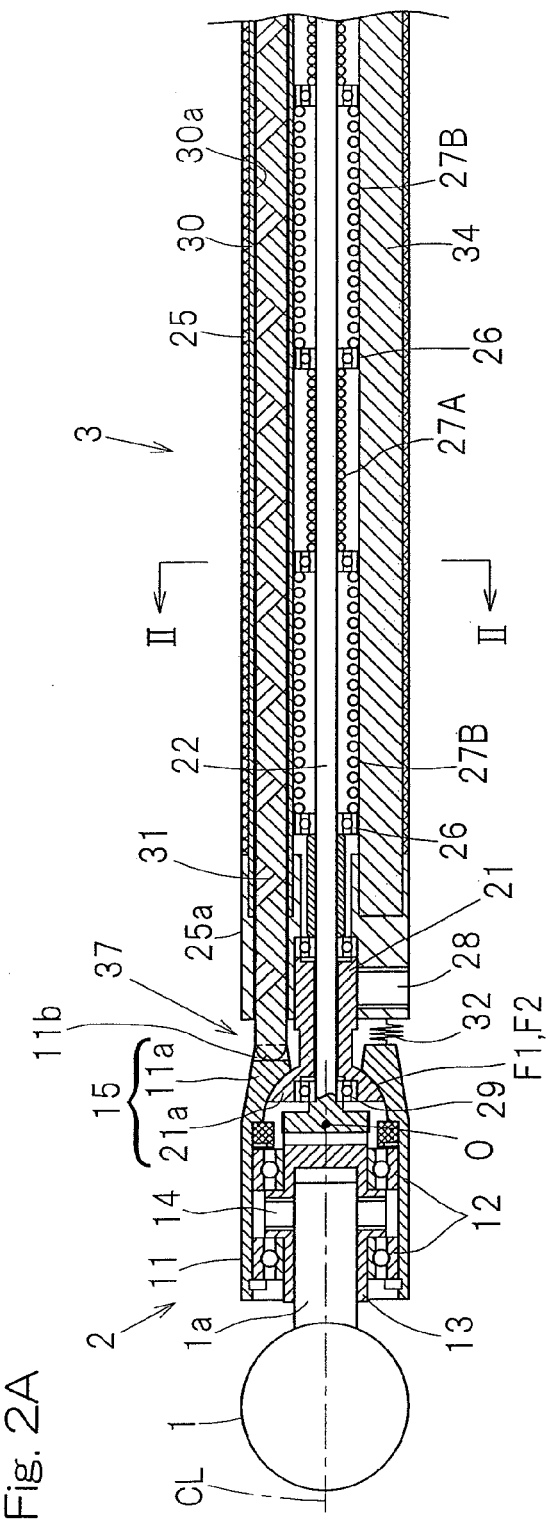
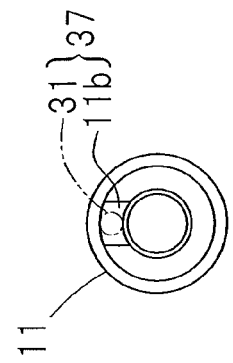
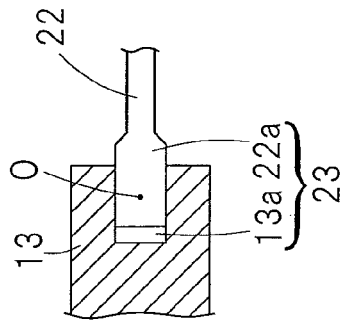
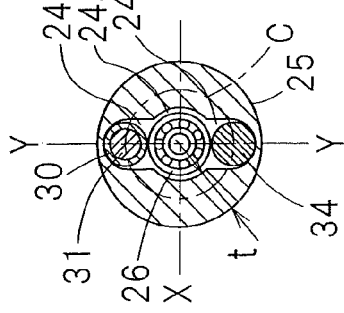

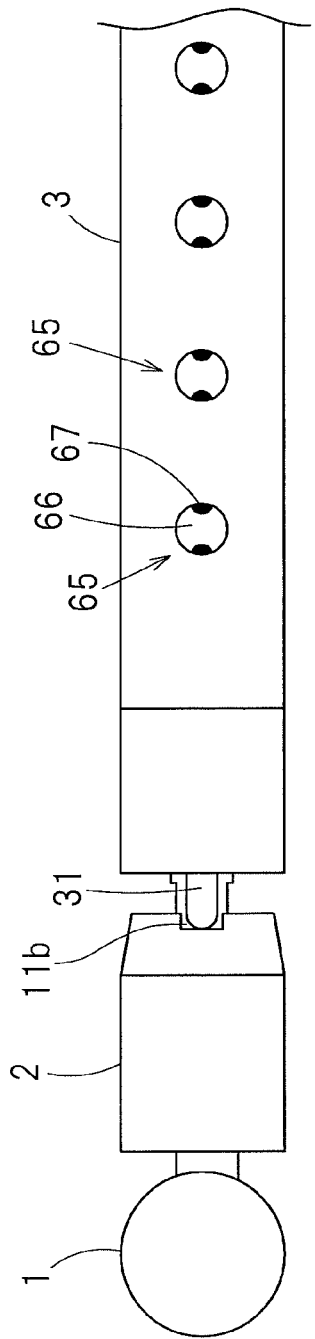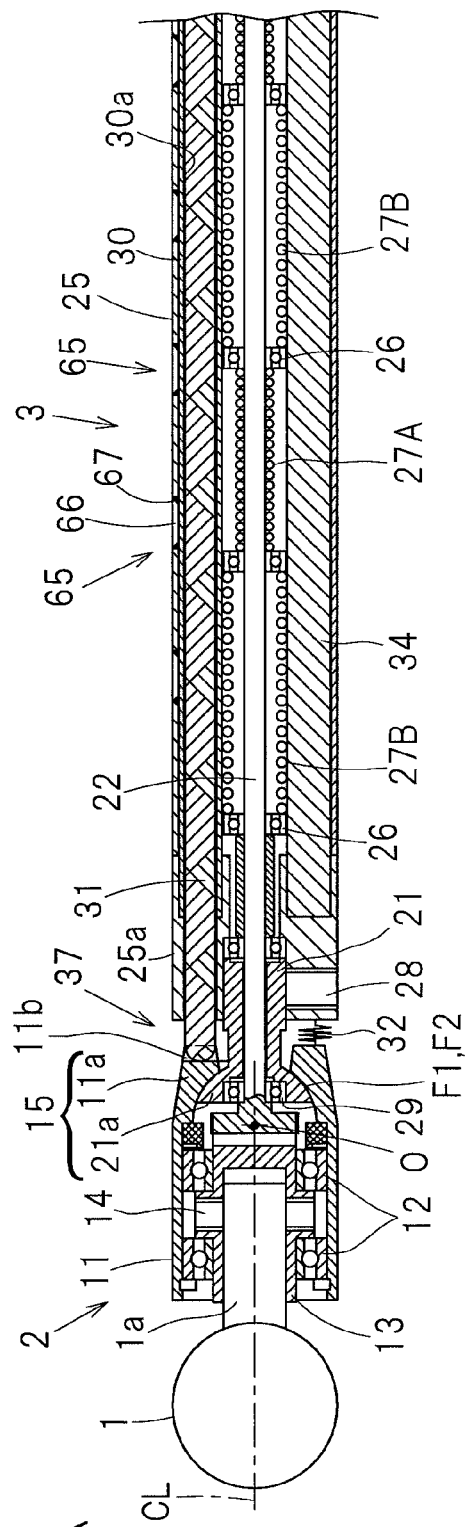

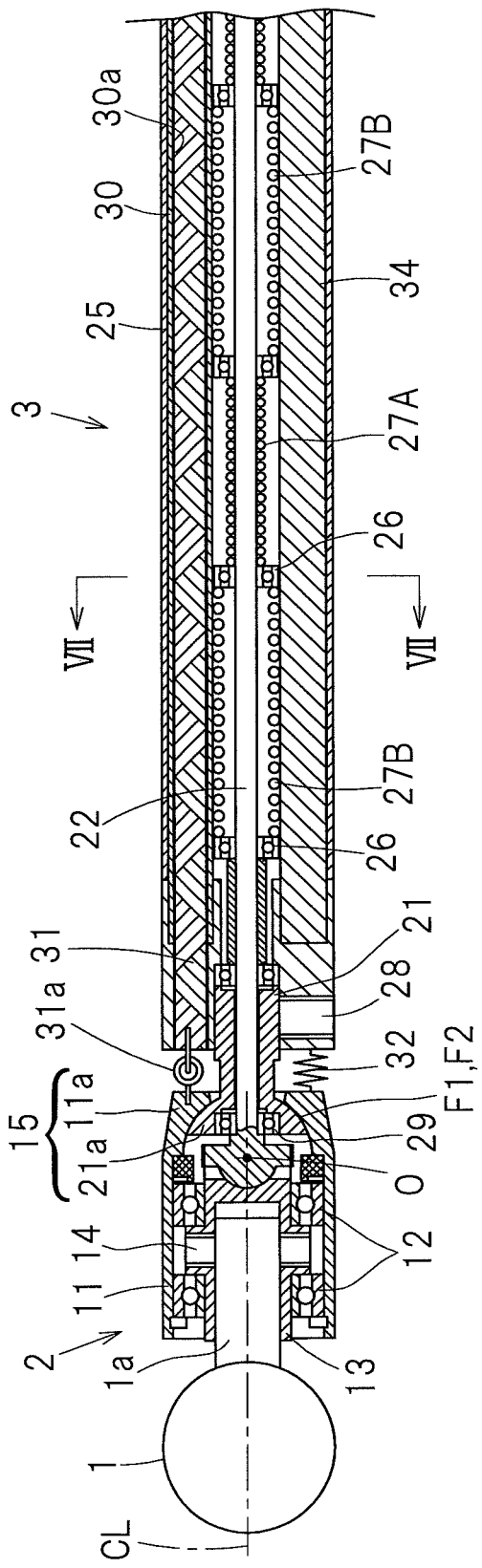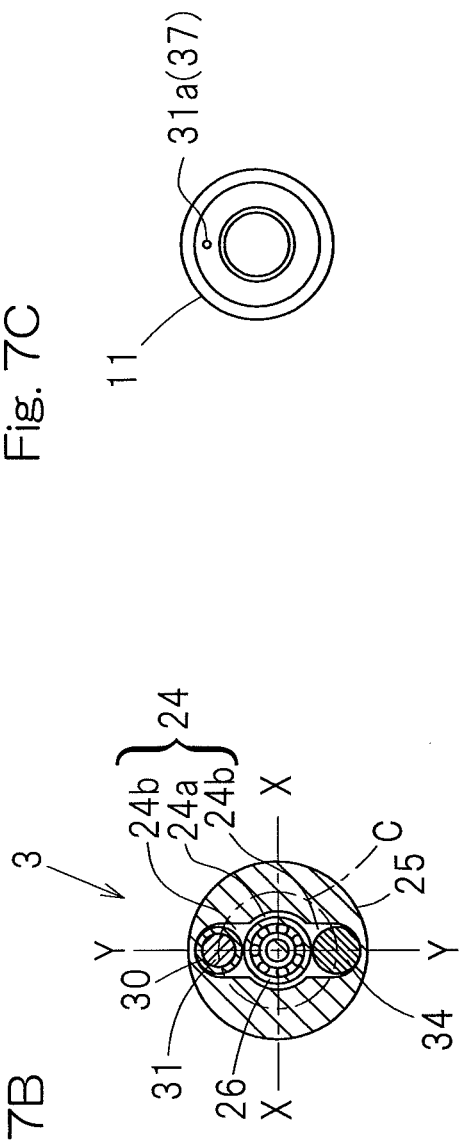

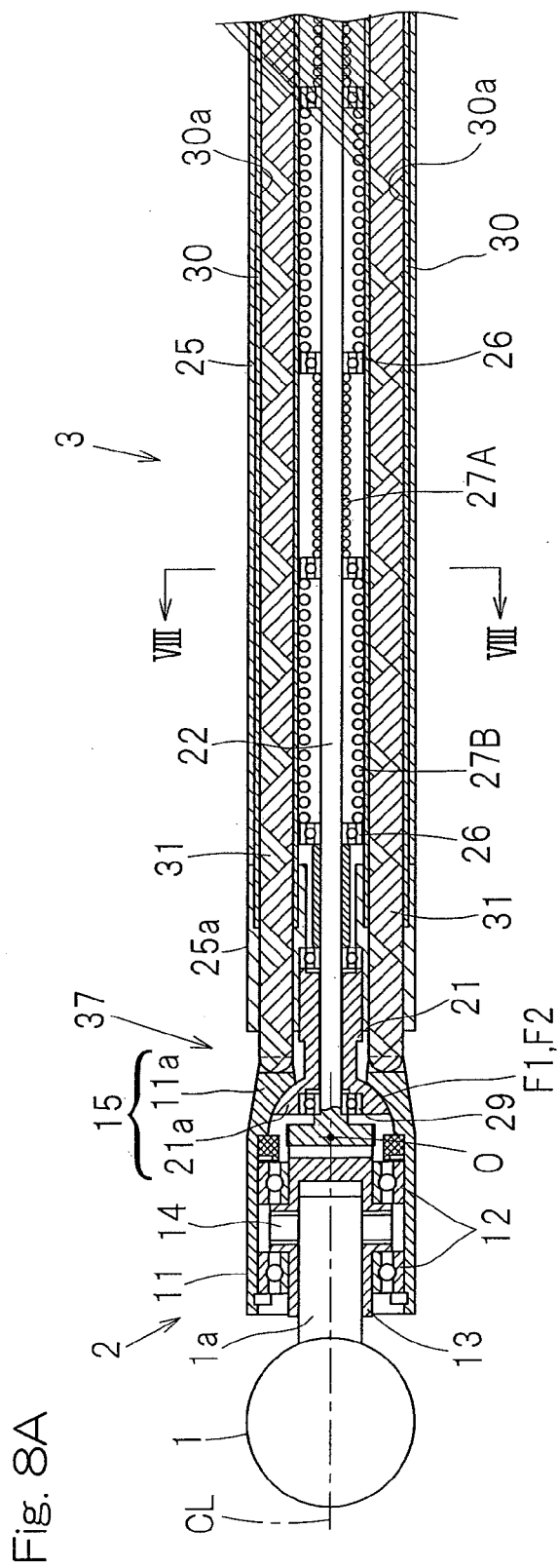
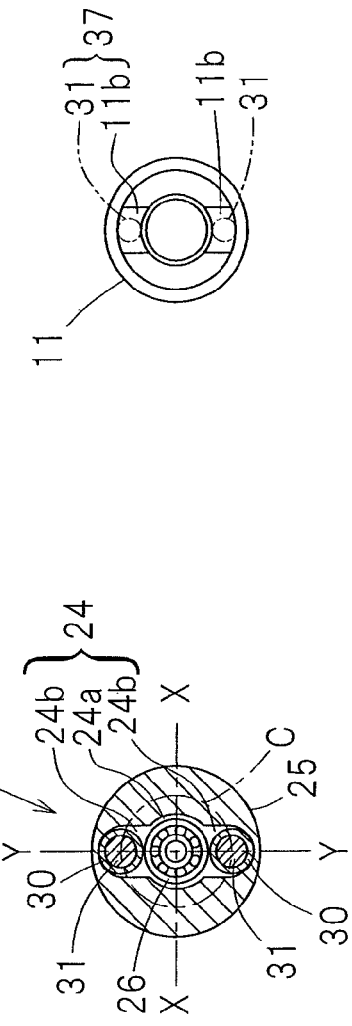
Fig. 8A
Fig. 8B
Fig. 8C

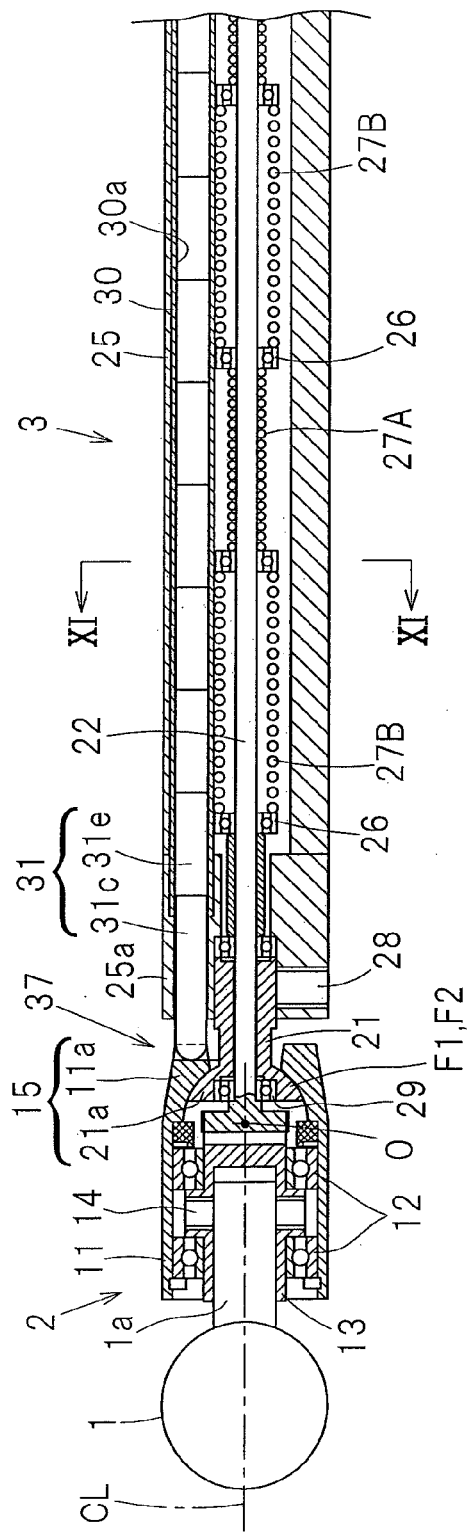
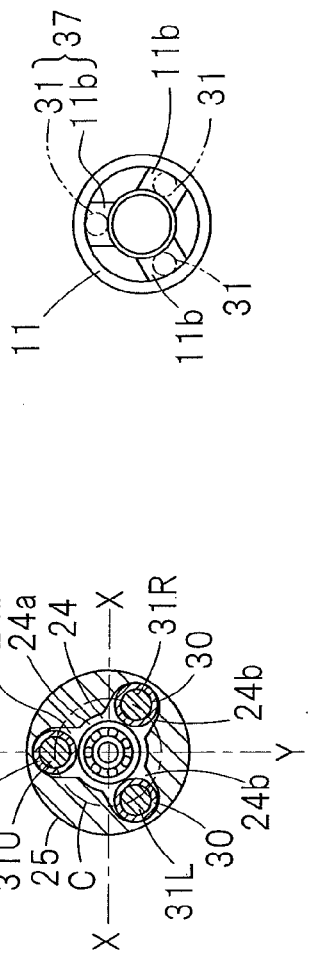
Fig. 11A
Fig. 11B
Fig. 11C

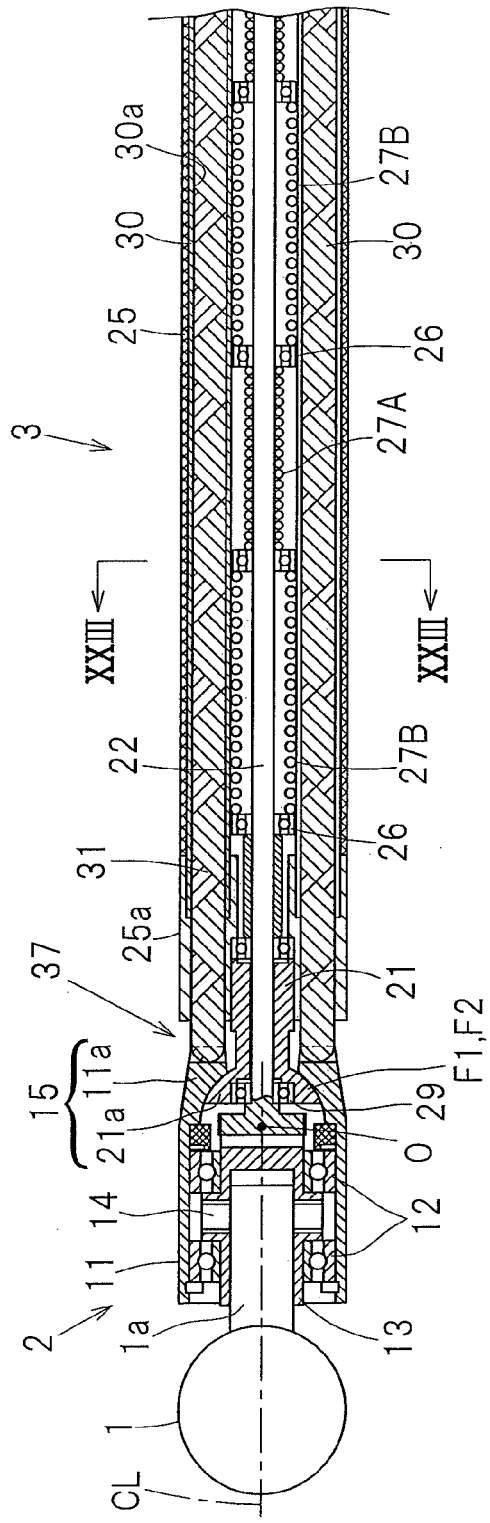
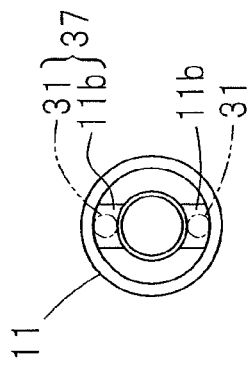
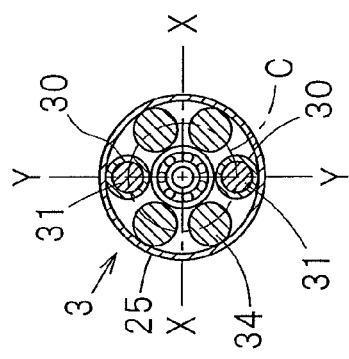

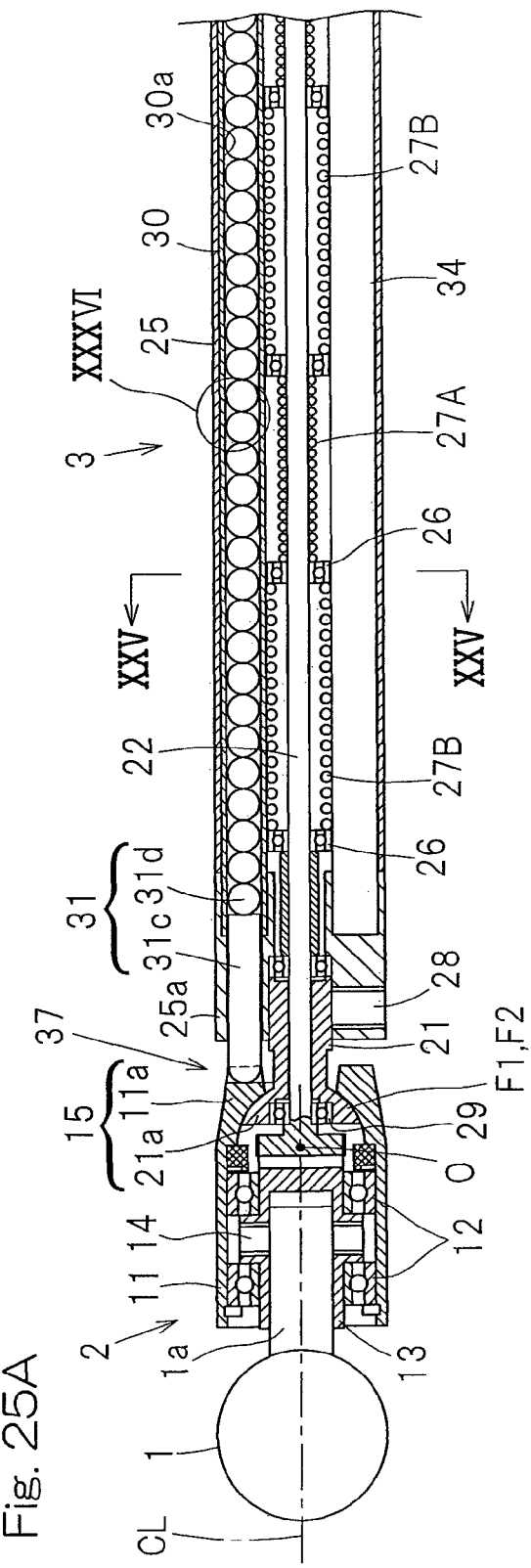
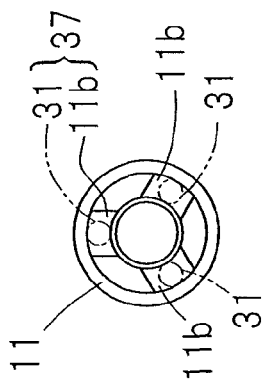
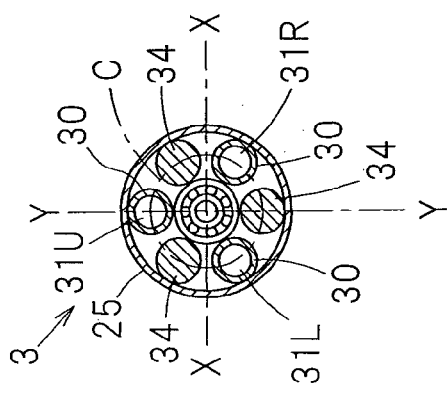

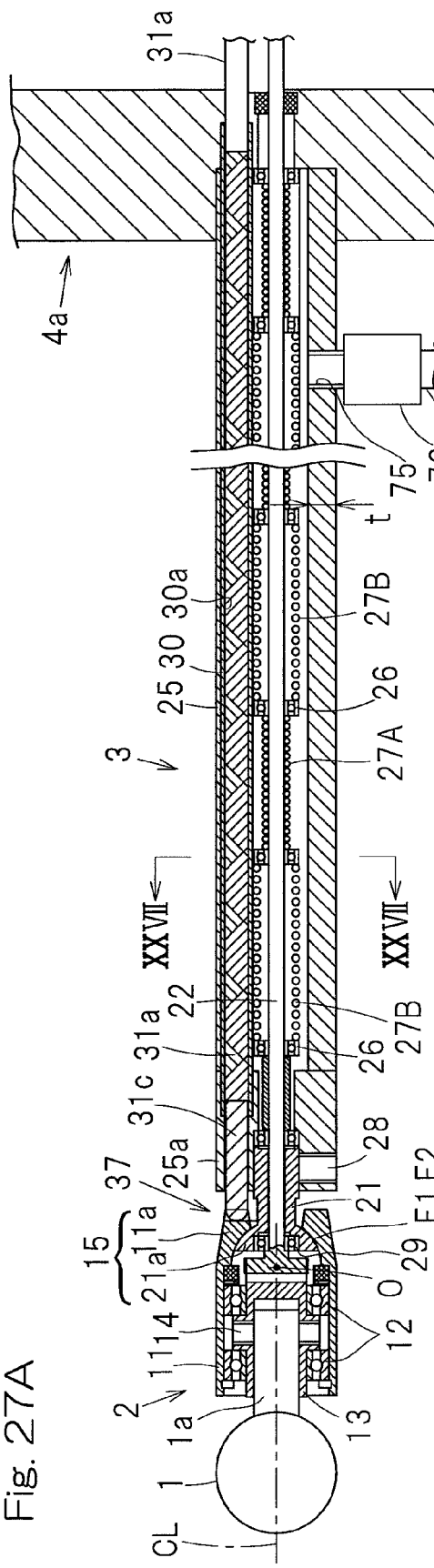
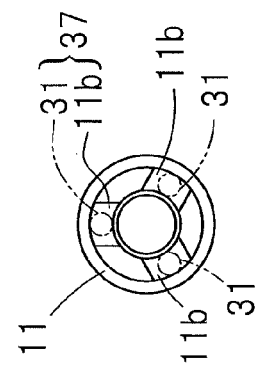
Fig. 27C
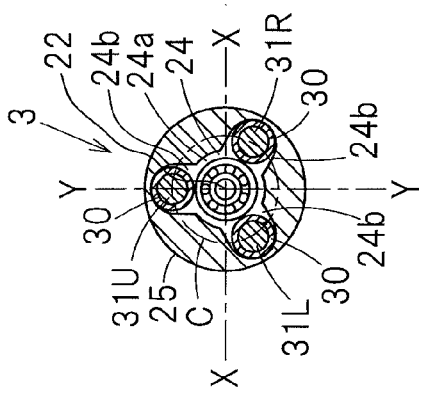
Fig. 27B

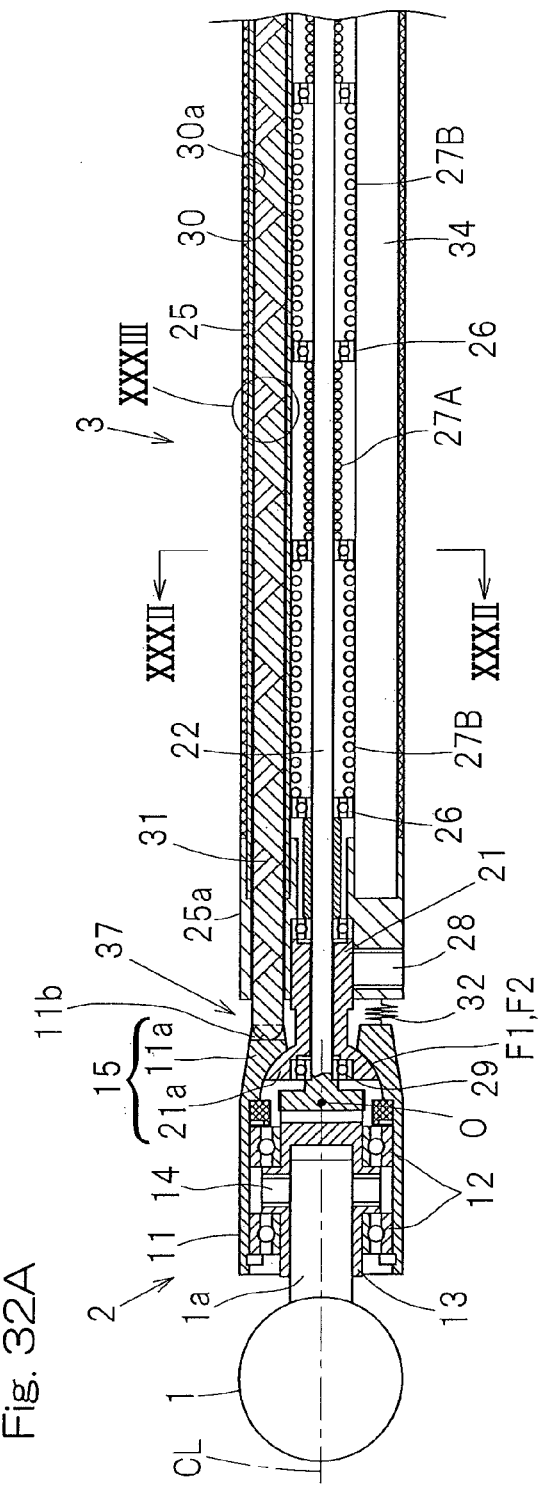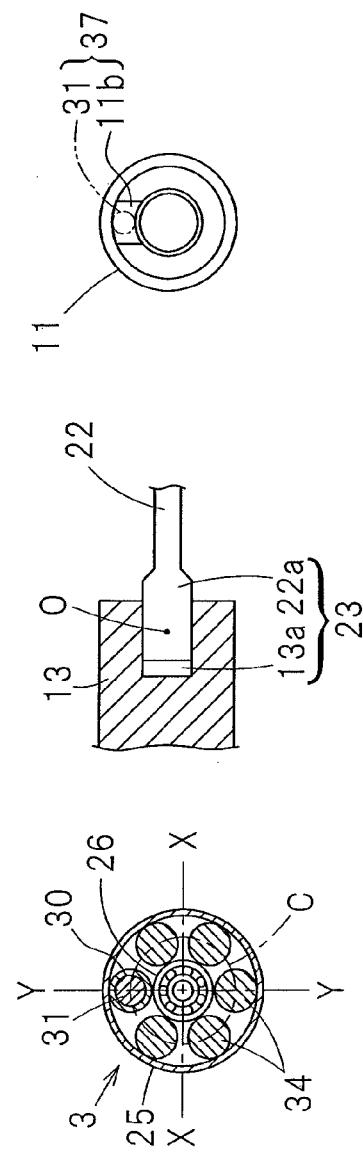
Fig. 32A
Fig. 32B
Fig. 32C
Fig. 32D

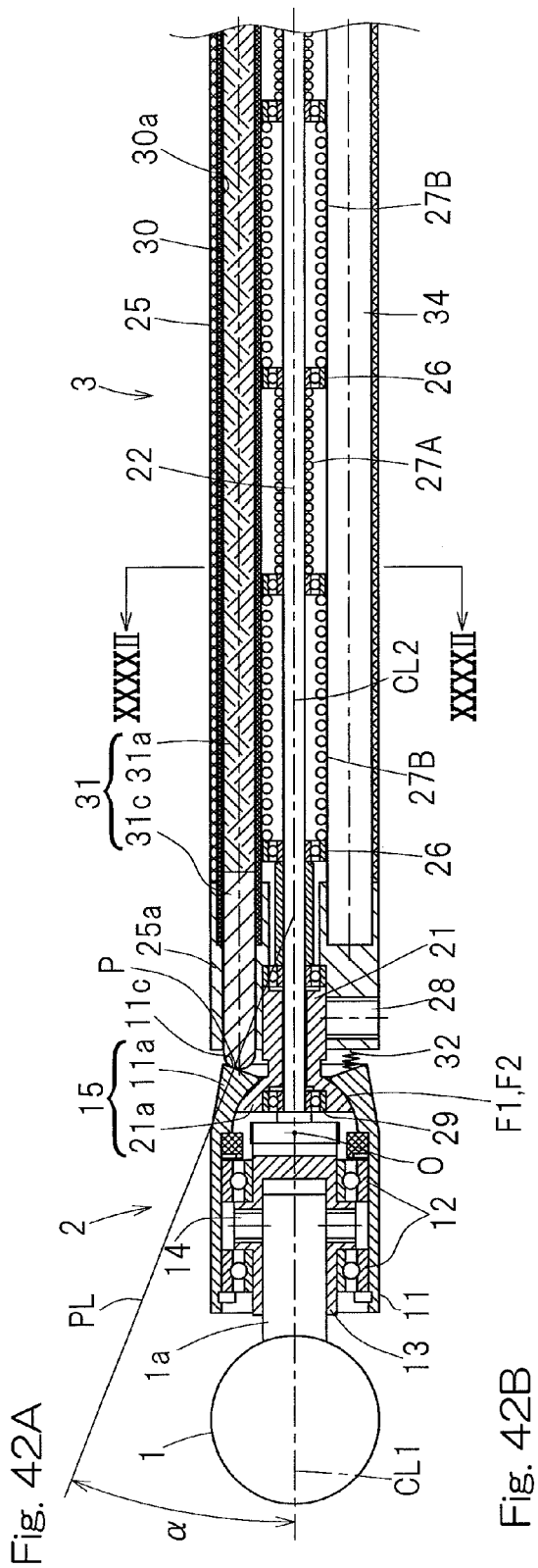
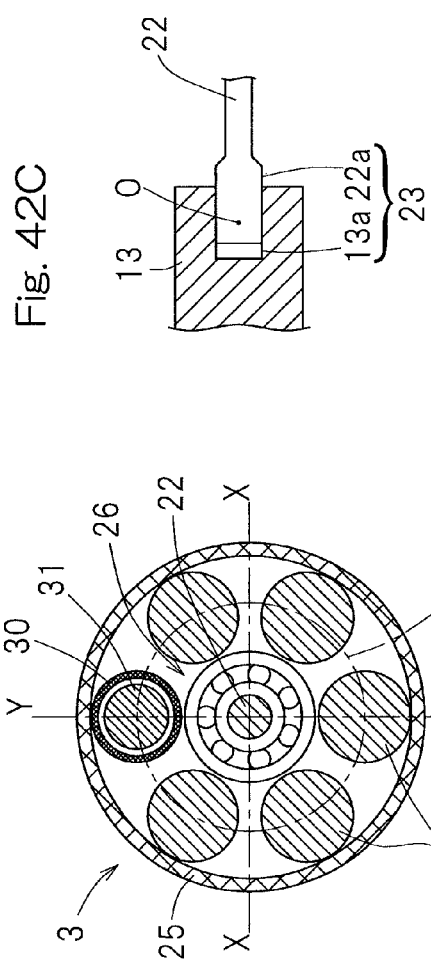
Fig. 42A
Fig. 42C
Fig. 42B

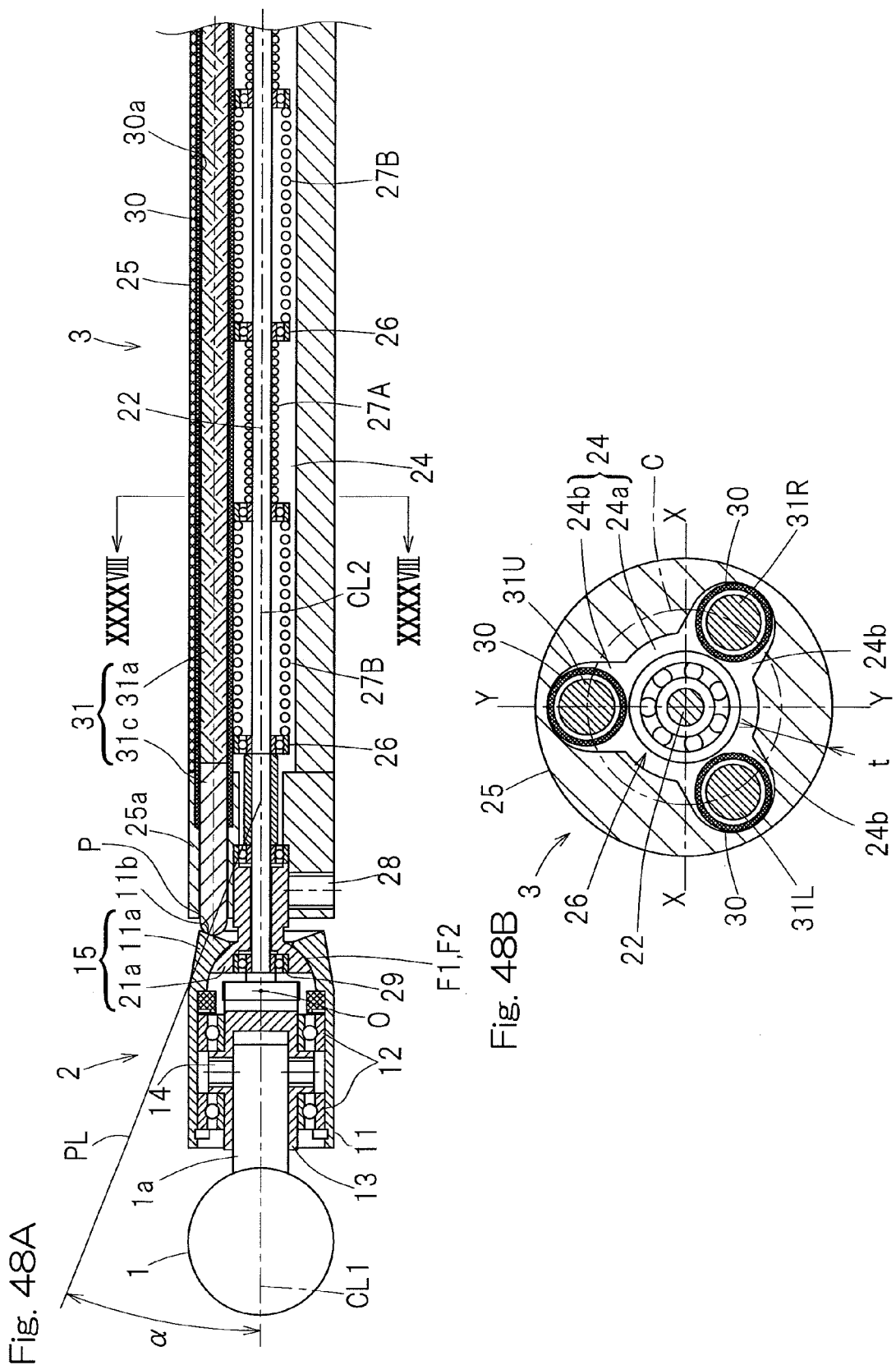

REMOTE-CONTROLLED ACTUATOR

CROSS REFERENCE TO THE RELATED APPLICATION

This application is a continuation application, under 35 U.S.C §111(a) of international application No. PCT/JP2009/005106, filed Oct. 2, 2009, which claims priority to Japanese patent application No. 2008-261339, filed Oct. 8, 2008; Japanese patent applications No. 2008-264437 and No. 2008-264438, both filed Oct. 10, 2008; and Japanese patent application No. 2009-013009, filed Jan. 23, 2009, the entire disclosures of which are herein incorporated by reference as a part of this application.

BACKGROUND OF THE INVENTION

1. Field of the Invention

The present invention relates to a remote controlled actuator for use in medical and machine processing fields and capable of changing the attitude of a machine tool.

2. Description of Related Art

Remote controlled actuators are currently available; some are used in the medical field for osteal treatment and some are used in the mechanical processing field for drilling and cutting a bone. Any of those remote controlled actuators controls by remote control a machine tool fitted to a distal end of an elongated pipe of a linear or curved configuration. However, since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip join replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet with this desire, the following technique has hitherto been suggested. For example, the Patent Document 2 listed below discloses the elongated pipe having its intermediate portion curved double to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated 180°.

PRIOR ART LITERATURE

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] JP Laid-open Patent Publication No. 2001-17446

If in a condition, in which the artificial joint is inserted into an artificial joint insertion hole formed in the living bone, a large gap exist between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever the pipe take any shape, the working range of the tool is limited by the shape of the pipe and, therefore, it is difficult to widen the working range of the tool to process the artificial joint insertion hole so that the living bone and the artificial joint may can have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant or assignee of the present invention has attempted to provide a remote controlled actuator of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe. It has, however, been found that since the tool is connected to the distal end of the elongated pipe, disposition of a mechanism for changing the attitude of the tool is considerably limited and, therefore, artifices are required to overcome those limitations. In addition, it is desirable that during the processing since not only the tool and the article to be processed, but also rotatable members of the actuator emit heat, those sites of heat emission can be efficiently cooled. Where a cooling unit is provided for this purpose, it is necessary to prevent the coolant liquid from adversely affecting mechanical portions. Also, it is expected that the pipe section may have a curved shape and, even in such case, it is desirable that the attitude can be accurately altered. In addition, in order to reduce the weight of and energies consumed by the actuator for medical use, it is desirable that the attitude altering drive source of a size as small as possible is used. Yet, so long as the actuator is used in the medical field, it is requires to avoid the use of a lubricant and/or a coating harmful to the human body and to enable the attitude of the tool to be altered smoothly. It is to be noted that in the case of the medical actuator having no elongated pipe used therein, a portion where the tool is mounted can change its attitude relative to a portion to be gripped by hand (See, for example, Patent Document 4 listed above.), but nothing has yet been suggested in the art that the attitude of the tool can be altered by remote control.

It may be expected that in the case of the remote controlled actuator utilizing the elongated pipe section having the tool fitted to the tip end thereof, the elongated pipe section flexes accompanied by displacement in position of the tool when an external force acts on, for example, the tool. Once the tool displaces in position, neither the accurate processing nor the accurate control of the attitude of the tool can be accomplished. Also, if the pipe section is apt to flex, a cutting force will hardly acts on the article to be processed in a direction normal thereto, thus reducing the machinability. In view of those particulars, it has been required for the pipe section to have a sufficient rigidity.

SUMMARY OF THE INVENTION

The present invention is intended to provide a remote controlled actuator of a type, in which the attitude of the tool fitted to the tip end of the elongated pipe section can be altered by remote control; a spindle guide section as the pipe section has a high rigidity; assemblability is good; sites tending to emit heat during processing can be efficiently cooled without adversely affecting any mechanical portion; the attitude can be accurately altered even when the spindle guide section as the pipe section is curved; a compact attitude altering drive source can be employed; and the attitude of the tool can be smoothly altered.

The remote controlled actuator according to the present invention includes a spindle guide section of an elongated configuration, a distal end member fitted to a tip end of the spindle guide section through a distal end member connecting unit for alteration in attitude, and a drive unit housing to which a base end of the spindle guide section is connected; in which the distal end member rotatably supports a spindle for holding a tool; in which the spindle guide section includes a hollow outer shell pipe forming an outer shell for the spindle guide section, a rotary shaft provided within a hollow of the outer shell pipe, which hollow extends to opposite ends of the outer shell pipe, for transmitting rotation of a tool rotating drive source, provided within the drive unit housing, to the spindle, a guide pipe provided within the hollow and having a guide hole so as to extend to opposite ends thereof, and one or a plurality of attitude altering members reciprocally movably inserted within the guide pipe for altering the attitude of the distal end member; in which one or a plurality of attitude altering members is, while a tip end thereof is held in contact with the distal end member, selectively advanced or retracted one at a time; in which an attitude altering drive source for selectively advancing or retracting the or each attitude altering member is provided within the drive unit housing; and in which the hollow has a round hole portion at a center and a grooved portion depressed radially outwardly from the round hole portion, and the rotary shaft is arranged within the round hole portion whereas the guide pipe is arranged within the grooved portion.

According to the above described construction, as a result of rotation of the tool fitted to the distal end member, cutting of the bone or the like takes place. In such case, when the or each attitude altering member is selectively advanced and retracted one at a time by the attitude altering drive source, the tip end of the or each attitude altering member works on the distal end member to allow the attitude of the distal end member, fitted to the tip end of the spindle guide section through the distal end member connecting unit for alteration in attitude, to alter. The attitude altering drive source is provided within the drive unit housing on the base end side of the spindle guide section and the alteration of the attitude of the distal end member is carried out by remote control. Since the or each attitude altering member is passed through the hollow guide pipe, the or each attitude altering member can work on the distal end member properly at all time without being displaced in a direction transverse to the longitudinal direction thereof, and the operation to alter the attitude of the distal end member takes place accurately.

Since the hollow of the outer shell pipe includes the round hole portion at the center and the grooved portion radially outwardly depressed from the round hole portion, the wall thickness of a site other than the grooved portion of the outer shell pipe can be increased. Accordingly, the rigidity (the geometrical moment of inertia) of the spindle guide section becomes high and as a result, the positioning accuracy of the distal end member can be increased, thus increasing the cutting capability. For example, the geometric moment of inertia of the outer shell pipe is chosen to be of a value equal to or larger than ½ of a solid shaft of the same outer diameter. Also, positioning of the guide pipe in the grooved portion facilitates the positioning of the guide pipe in the circumferential direction, resulting in a good assemblability.

In the present invention, the or each attitude altering member may include a plurality of force transmitting members arranged in a row extending in a direction along a lengthwise direction of the guide pipe, or a wire extending in a direction along the lengthwise direction of the guide pipe.

In either case, the or each attitude altering member can be selectively advanced and retracted by the attitude altering drive source. Also, the or each attitude altering member in its entirety has a flexibility and is therefore capable of following flexure of the spindle guide section.

In the present invention, the guide pipe and the attitude altering member inserted within the guide pipe may be each provided at two or three locations, and the attitude altering drive source is provided for each of the attitude altering members so that the attitude of the distal member can be altered and maintained in dependence on the balance of respective working forces of the attitude altering members at the two or three locations acting on the distal end member. Since the distal end member can be pressurized by the two or three attitude altering member, the attitude stability of the distal end member can be increased as compared with the case in which the distal end member is pressurized by the sole attitude altering member.

In the present invention, where a plurality of rolling bearings are provided within the spindle guide section for rotatably supporting the rotary shaft, a spring element for applying a preload to the rolling bearings is preferably provided between the neighboring rolling bearings.

In order to achieve a good finish of processing, it is recommended to perform the processing with the spindle driven at a high speed. When the spindle is driven at a high speed, an effect to reduce a cutting resistance acting on the tool can also be appreciated. Since the spindle is transmitted with a rotational force through the elongated rotary shaft in the form of a wire or the like, the rolling bearing used to rotatably support the rotary shaft is to be applied a preload in order to achieve the high speed rotation of the spindle. If the spring element for applying this preload is provided between the neighboring rolling bearings, the spring element can be installed with no need to increase the diameter of the spindle guide section.

Also, where the rolling bearing is provided within the spindle guide section for rotatably supporting the rotary shaft, it is possible for the guide pipe to support the outer diametric surface of the rolling bearing.

By the utilization of the guide pipe, the outer diametric surface of the rolling bearing can be supported with no need to use any extra member.

Where the rolling bearing is provided within the spindle guide section for rotatably supporting the rotary shaft, a cooling unit may be provided for cooling the bearings with a coolant liquid flowing inside the outer shell pipe.

Component parts including, for example, the spindle for rotating the tool and the rotary shaft emit heat by the effect of friction taking place during rotation thereof. The emitting heat so evolved results in heating of the bearing. The use of the cooling unit is effective to cool the bearing and a heated site of those component parts with the coolant liquid. If the coolant liquid is allowed to flow through the inside of the outer shell pipe, the spindle guide section can be simplified and downsized with no need to employ any extra tube for the supply of the coolant liquid.

In addition, an effect to lubricate the bearing with the coolant liquid is appreciated. If the coolant liquid is concurrently used for lubrication of the bearing, there is no need to use such a grease or the like as generally employed in the standard bearings and, yet, there is no need to use an extra lubricating device.

Also, a cooling unit may be provided for cooling the tool with a coolant liquid flowing inside the outer shell pipe, or a coolant liquid supplied from an outside.

During the processing, the tool and the article to be processed tend to emit heat. The use of the cooling unit is effective to cool the tool and the article to be processed with the coolant liquid.

In the present invention, a cooling unit may be provided, which has an interior, into which a coolant liquid is injected through a coolant liquid injecting hole defined in the vicinity of a base end of the spindle guide section, and which is capable of feeding it towards the tip end side through the interiors of the spindle guide section and the distal end member and finally discharging it from the distal end member towards the tool, together with a sealing unit for avoiding an ingress of the coolant liquid from the inside of the spindle guide section into the inside of the drive unit housing.

During the processing, not only are the tool and the article to be processed apt to emit heat, but also such rotatable members as, for example, the rotary shaft and the spindle evolve heat by the effect of friction taking place during rotation thereof. However, the use of the cooling unit makes it possible to cool the rotary shaft and the spindle to be cooled with the coolant liquid supplied towards the tip end side through the spindle guide section and the interior of the distal end member, and also, the tool and the articles to be cooled are also cooled by the coolant liquid discharged from the distal end member. Since the coolant liquid is allowed to flow through the spindle guide section and the interior of the distal end member, there is no need to install tubes for the supply of the coolant liquid outside the spindle guide section and the distal end member and, hence, the spindle guide section and the distal end member can be simplified and configured to have a reduced diameter.

Also, since the sealing unit is provided, an undesirable ingress of the coolant liquid from the inside of the spindle guide section into the drive unit housing can be avoided and as a result, any trouble will hardly occur in various mechanisms including, for example, the tool rotating drive source and the attitude altering drive source, both accommodated within the drive unit housing, thus avoiding an undesirable reduction in lifetime.

In the present invention, the sealing unit referred to above may be a slide bearing for supporting the rotary shaft at a location on the side of the base end and remote from the coolant liquid injecting hole.

Since the slide bearing supports the rotary shaft in contact therewith, a gap in a rotating area between the bearing and the rotary shaft is small as compared with that in the rolling bearing. For this reason, using the slide bearing for a bearing positioned on the base end side of the coolant liquid injecting hole allows it to be concurrently used as a sealing member.

In the present invention, the sealing unit referred to above may include a shielded chamber provided in the drive unit housing and communicated with the inside of the spindle guide section at the base end of the spindle guide section, and the pressure inside the shielded chamber may be chosen to be higher than the atmospheric pressure.

Since the coolant liquid discharge portion of the distal end member is communicated with the atmospheric pressure, selection of the pressure inside the shielded chamber to be higher than the atmospheric pressure is effective to allow the coolant liquid within the spindle guide to flow towards the distal end member side and, therefore, an undesirable ingress of the coolant liquid within the spindle guide section into the drive unit housing can be avoided.

In the present invention, a friction reducing unit may be provided between an inner surface of the guide hole and the attitude altering member for reducing a frictional force developed therebetween.

Since the friction reducing unit is employed, the frictional force developed between the inner surface of the guide hole and the attitude altering member can be reduced. Accordingly, the force applied from the attitude altering drive source to the attitude altering member can be smoothly transmitted to the distal end member, and therefore, the attitude of the distal end member can be altered accurately. Also, even when the spindle guide section is curved, the force applied to the attitude altering member can be accurately transmitted to the distal end member and, therefore, the attitude of the distal end member can be altered accurately. Yet, since the frictional force is reduced as described above, the attitude altering drive source cam be compactized and the amount of electrical energies consumed can also be reduced.

In the present invention, the friction reducing unit may include a coating layer coated on at least one of the inner surface of the guide hole and a surface of the attitude altering member. Alternatively, the friction reducing unit may be a liquid for lubrication existing within the guide hole.

In either case, the frictional force developed between the inner surface of the guide hole and the attitude altering member can be reduced.

Where the friction reducing unit is employed in the form of a liquid for lubrication, the liquid for lubrication referred to above can be employed in the form of water or physiological saline.

When this remote controlled actuator is designed for medical use and the processing is to be performed with the distal end member inserted into the living body, the liquid for lubrication will not adversely affect the living body provided that the liquid for lubrication is employed in the form of water or psychological saline.

In the present invention, when the angle formed between a center line of the rotary shaft and a perpendicular line normal to the tangential line at a point of contact between the distal end member and the attitude altering member is expressed by α, the angle α is preferably within the range of 0° to 45°.

If a contact surface of the distal end member with the attitude altering member lies perpendicular to the direction of selective advance or retraction of the attitude altering member, in other words, the angle α formed between the center line of the rotary shaft and the perpendicular line normal to the tangential line at a point of contact between the distal end member and the attitude altering member is chosen to be 0°, no slip take place between the distal end member and the attitude altering member and, therefore, the distal end member is unable to undergo a swinging motion. However, if the angle α is greater than 0°, that is, α>0°, the distal end member can slide to swing relative to the attitude altering member and, therefore, the attitude of the distal end member can be smoothly altered. For this reason, neither the lubricant nor the coating, both of which are undesirable to the human body, is needed, and as a result, it is suited to the actuator that is to be used in the medical field. On the other hand, if the angle α is equal to or greater than 45°, assuming that the force applied by the attitude altering member to the distal end member is divided into an axially acting force and a radially acting force, the radially acting force is so larger than the axially acting force that no drive force can be sufficiently transmitted to the distal end member. Also, as the radially acting force becomes large, the frictional force developed between the attitude altering member and the inner surface of the guide hole of the guide pipe, which is a guide face thereof, becomes large, requiring a large drive force.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 2A is a longitudinal sectional view showing a distal end member and a spindle guide section both employed in the remote controlled actuator;

FIG. 2B is a cross sectional view taken along the line II-II in FIG. 2A;

FIG. 2C is a diagram showing a structure for coupling the distal end member and a rotary shaft together;

FIG. 2D is a diagram as viewed from a base (or proximate) end side of a housing for the distal end member;

FIG. 5A is a longitudinal sectional view showing the distal end member and the spindle guide section, both employed in the remote controlled actuator according to a second preferred embodiment of the present invention;

FIG. 5B is a plan view of FIG. 5A;

FIG. 7A is a longitudinal sectional view showing the distal end member and the spindle guide section, both employed in the remote controlled actuator according to a fourth preferred embodiment of the present invention;

FIG. 7B is a cross sectional view taken along the line VII-VII in FIG. 7A;

FIG. 7C is a view as viewed from the base end side of the housing for the distal end member;

FIG. 8A is a longitudinal sectional view showing the distal end member and the spindle guide section, both employed in the remote controlled actuator according to a fifth preferred embodiment of the present invention;

FIG. 8B is a cross sectional view taken along the line VIII-VIII in FIG. 8A;

FIG. 8C is a view as viewed from the base end side of the housing for the distal end member;

FIG. 11A is a longitudinal sectional view showing the distal end member and the spindle guide section, both employed in the remote controlled actuator according to an eighth preferred embodiment of the present invention;

FIG. 11B is a cross sectional view taken along the line XI-XI in FIG. 11A;

FIG. 11C is a view as viewed from the base end side of the housing for the distal end member;

FIG. 23A is a longitudinal sectional view showing the distal end member and the spindle guide section, both employed in the remote controlled actuator according to a fourth applied case of the present invention;

FIG. 23B is a cross sectional view taken along the line XXIII-XXIII in FIG. 23A;

FIG. 23C is a view as viewed from the base end side of the housing for the distal end member;

FIG. 25A is a longitudinal sectional view showing the distal end member and the spindle guide section, both employed in the remote controlled actuator according to a sixth applied case of the present invention;

FIG. 25B is a cross sectional view taken along the line XXV-XXV in FIG. 25A;

FIG. 25C is a view as viewed from the base end side of the housing for the distal end member;

FIG. 27A is a longitudinal sectional view showing the distal end member and the spindle guide section, both employed in the remote controlled actuator according to a ninth embodiment of the present invention;

FIG. 27B is a cross sectional view taken along the line XXVII-XXVII in FIG. 27A;

FIG. 27C is a view as viewed from the base end side of the housing for the distal end member;

FIG. 32A is a longitudinal sectional view showing the distal end member and the spindle guide section, both employed in the remote controlled actuator according to an eighth applied case of the present invention;

FIG. 32B is a cross sectional view taken along the line XXXII-XXXII in FIG. 32A;

FIG. 32C is a view showing the connection structure between the distal end member and the rotary shaft;

FIG. 32D is a view as viewed from the base end side of the housing for the distal end member;

FIG. 42A is a longitudinal sectional view showing the distal end member and the spindle guide section, both employed in the remote controlled actuator according to a ninth applied case of the present invention;

FIG. 42B is a cross sectional view taken along the line XXXXII-XXXXII in FIG. 42A;

FIG. 42C is a view showing the connection structure between the distal end member and the rotary shaft;

FIG. 48A is a longitudinal sectional view showing the distal end member and the spindle guide section, both employed in the remote controlled actuator according to a tenth preferred embodiment of the present invention; and FIG. 48B is a cross sectional view taken along the line XXXXVIII-XXXXVIII in FIG. 48A.

DESCRIPTION OF PREFERRED EMBODIMENTS

Figure 1:
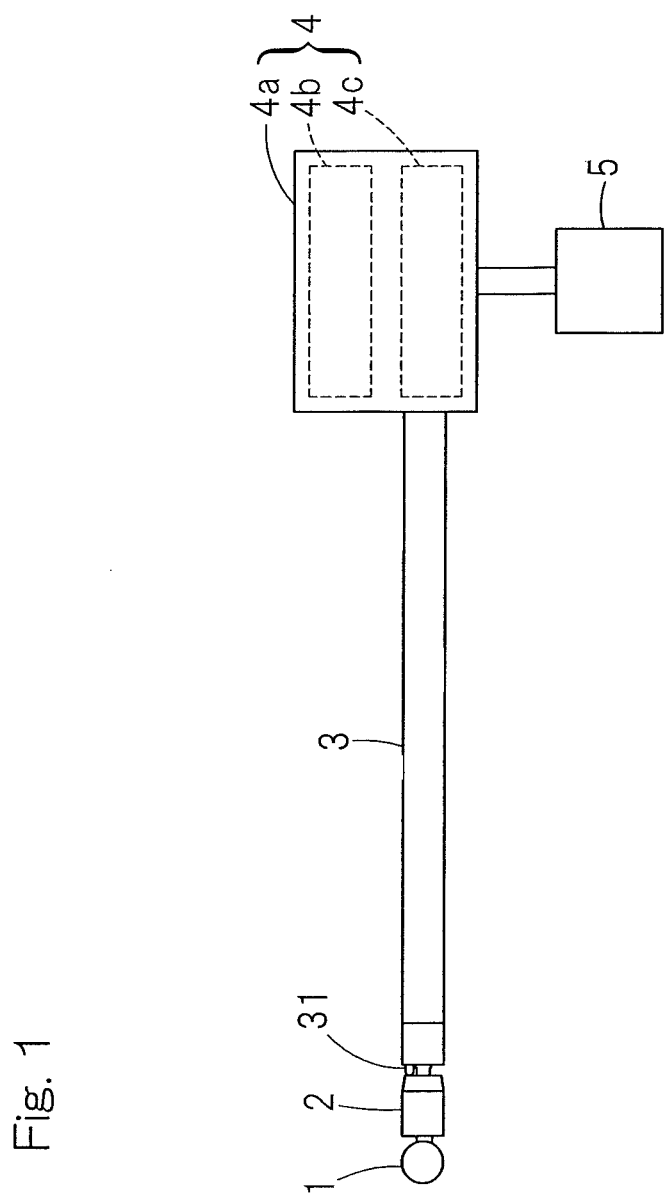
FIG. 1 is a diagram showing a schematic structure of a remote controlled actuator according to a first preferred embodiment of the present invention.

A first preferred embodiment of the present invention will now be described with particular reference to FIG. 1 to FIGS. 3A and 3B. Referring to FIG. 1, a remote controlled actuator according to the first embodiment of the present invention includes a distal end member 2 for holding a rotary tool 1, an elongated spindle guide section 3 having a distal end to which the distal end member 2 is coupled for displacement in attitude, a drive unit housing 4a to which a proximal end of the spindle guide section 3 is coupled, and a controller 5 for controlling a tool rotating drive mechanism 4b and an attitude altering drive mechanism 4c, both accommodated within the drive unit housing 4a. The drive unit housing 4a cooperates with the built-in tool rotating drive mechanism 4b and attitude altering drive mechanism 4c to form a drive unit 4.

As best shown in FIGS. 2A to 2D, the distal end member 2 includes a generally or substantially cylindrical housing 11 and a spindle 13 rotatably accommodated within such cylindrical housing 11 through a pair of bearings 12. The spindle 13 is of a tubular shape having a distal side opening and has a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member coupling unit 15. The distal end member coupling unit 15 is means for supporting the distal end member 2 for displacement in attitude and is comprised of a spherical bearing. More specifically, the distal end member coupling unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered. It is to be noted that since in this example, the distal end member 2 can have its attitude altered about a lateral X-axis passing through the center of curvature O, the guide faces F1 and F2 may be a cylindrical surface having a longitudinal axis represented by the X-axis passing through the point O.

Figure 3A:
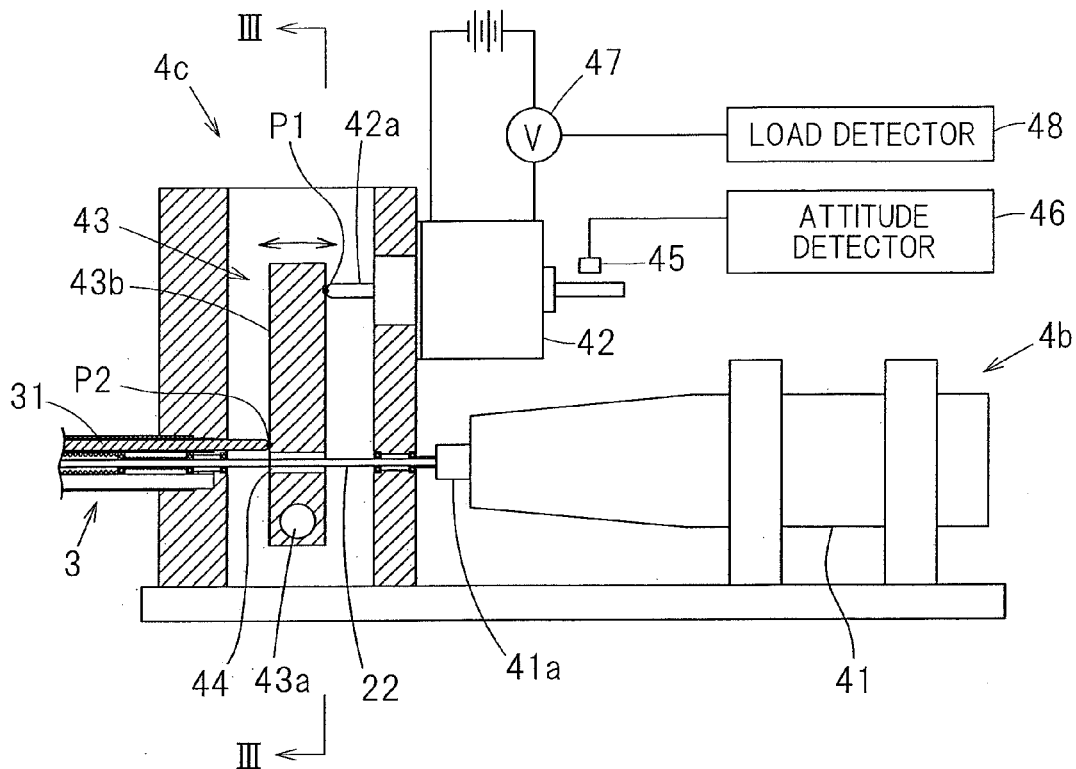
FIG. 3A is a diagram showing a side view of a tool rotating drive mechanism and an attitude altering drive mechanism, both used in the remote controlled actuator, shown together with a control system.
Figure 3B:
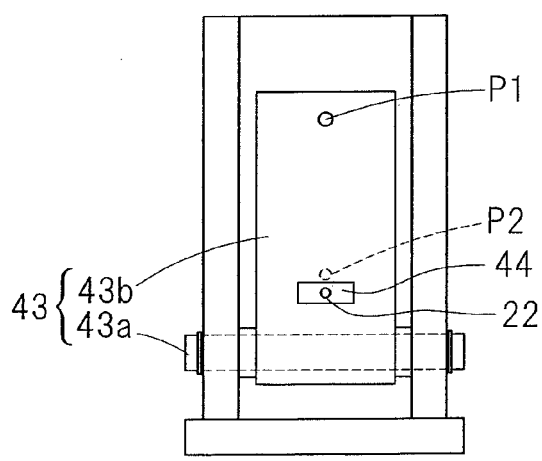
FIG. 3B is a cross sectional view taken along the line III-III in FIG. 3A.

The spindle guide section 3 includes a rotary shaft 22 for transmitting a rotational force exerted by a tool rotating drive source 41 accommodated within the drive unit housing 4a (FIGS. 3A and 3B). In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 2C, the spindle 13 and the rotary shaft 22 are connected together by means of an universal joint 23 for transmitting rotation from the rotary shaft 22 to the spindle 13. The universal joint 23 is made up of a groove 13a, defined in a closed base end of the spindle 13, a projection 22a defined in a distal end of the rotary shaft 22 and engageable in the groove 13a. The center of joint between the groove 13a and the projection 22a is located at the same position as the centers of curvature O of the guide faces F1 and F2. It is, however, to be noted that the rotary shaft 22 and the projection 22a may be formed of members separate from each other.

The spindle guide section 3 includes an outer shell pipe 25 which forms an outer shell for the spindle guide section 3. The outer shell pipe 25 has a hollow extending to opposite ends thereof, which hollow is made up of a round hole portion 24a at a center portion thereof and two grooved portions 24b radially outwardly depressed from respective circumferential locations of an outer periphery of the round hole portion 24a, which locations form a 180° phase relative to each other. A peripheral wall of a tip end of each of those grooved portions 24b represents a semicircular shape in section. By way of example, the outer shell pipe 25 has an outer diameter within the range of 8 to 10 mm and, also, an inner diameter at a location other than the grooved portions 24 that is within the range of 3 to 5 mm. Also, as material for the outer shell pipe 25, stainless steel or titanium or the like is suitably used.

Since the outer shell pipe 25 is chosen to have such a sectional shape as shown and described above, the wall thickness t of the outer shell pipe 25 at the location other than the grooved portions 24b can be increased. Accordingly, the geometric moment of inertia of the outer shell pipe 25 can be rendered to be ½ or more of a solid shaft of the same outer diameter. For example, in the case of the solid shaft of 8 mm in outer diameter made of a stainless steel material, the geometric moment of inertia is about 200 mm$^4$.

The rotary shaft 22 is arranged within the round hole portion 24a of the hollow 24. The rotary shaft 22 so positioned is rotatably supported by a plurality of rolling bearings 26 positioned spaced a distant apart from each other in a direction axially of the spindle guide section 3. Spring elements 27A and 27B for generating a preload on the corresponding rolling bearing 26 are disposed between the neighboring rolling bearings 26. Each of those spring elements 27A and 27B is employed in the form of, for example, a compression spring. There are the spring element 27A for inner ring for generating the preload on the inner ring of the rolling bearing 26 and the spring element 27B for outer ring for generating the preload on the outer ring of the rolling bearing 26, and the both are arranged alternately relative to each other. The constraint member 21 referred to previously is fixed to a pipe end portion 25a of the outer shell pipe 25 by means of a fixing pin 28 and has its distal end inner peripheral portion supporting a distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

One of the grooved portions of the hollow 24, that is, the upper grooved portions 24b as viewed in FIG. 2B is provided with a hollow guide pipe 30 extending to opposite ends thereof. Within a guide hole 30a which is an inner diametric hole of this guide pipe 30, an attitude altering or operating member 31 is reciprocally movably inserted. In the instance as shown, the attitude altering member 31 is in the form of a wire. The attitude altering member 31 has a tip end representing a spherical shape which is held in contact with a bottom face of a radial groove portion 11b formed in a base (or proximal) end face of the housing 11. As shown in FIG. 2D, the groove portion 11b and the attitude altering member 31 cooperate with each other to define a rotation preventing mechanism 37 and, when a tip end portion of the attitude altering member 31 inserted in the groove portion 11b is engaged with a side face of the groove portion 11b, the distal end member 2 is prevented from rotating about a center line CL of the distal end member 2 relative to the spindle guide section 3.

At a position spaced 180° in phase from a peripheral position where the attitude altering member 31 referred to above is positioned, a restoring elastic member 32, which is in the form of, for example, a compression spring, is provided between a base end face of the housing 11 for the distal end member 2 and a tip end face of the outer shell pipe 25 of the spindle guide section 3. This restoring elastic member 32 has a function of biasing the distal end member 2 towards the side of a predetermined attitude.

The other of the grooved portions of the hollow 24, that is, the lower grooved portion 24b as viewed in FIG. 2B has a solid reinforcement shaft 34 arranged therein. The reinforcement shaft 34 is used for securing the rigidity of the spindle guide section 3. The guide pipe 30 and the reinforcement shaft 34 are arranged on the pitch circle C of the same diameter and cooperate with each other to support outer diametric surfaces of the rolling bearings 26.

The tool rotating drive mechanism 4b and the attitude altering drive mechanism 4c, both housed within the drive unit housing 4a, are best shown in FIGS. 3A and 3B. The tool rotating drive mechanism 4b makes use of a tool rotating drive source 41 that is controlled by the controller 5. This tool rotating drive source 41 is in the form of, for example, an electric motor, having its output shaft 41a coupled with a base end or proximal end of the rotary shaft 22. The attitude altering drive mechanism 4c makes use of an attitude altering drive source 42 that is controlled by the controller 5. This attitude altering drive source 42 is in the form of, for example, an electrically operated linear actuator having an output rod 42a, the movement of the output rod 42a in one of leftward and rightward directions one at a time being transmitted to the attitude altering member 31 through a force increasing and transmitting mechanism 43. The force increasing and transmitting mechanism 43 includes a pivot lever 43b pivotable about a support pin 43a and is so designed and so configured as to allow a force of the output rod 42a to work on a working point P1 of the lever 43b, which is spaced a long distance from the support pin 43a, and as to apply a force to the attitude altering member 31 at a force point P2, which is spaced a short distance from the support axis 43a, wherefore an output of the attitude altering drive source 42 can be increased and then transmitted to the attitude altering member 31. Since the use of the force increasing and transmitting mechanism 43 is effective to enable a large force to be applied to the attitude altering member 31 even in the linear actuator of a low output capability, the linear actuator can be downsized. The rotary shaft 22 extends through an opening 44 defined in the pivot lever 43b. It is to be noted that instead of the use of the attitude altering drive source 42 or the like, the attitude of the distal end member 2 may be manually operated from a remote site (by remote control). Also, one or the both of the tool rotation drive source 41 and the attitude altering drive source 42 may be provided outside the drive unit housing 4a.

The attitude altering drive mechanism 4c is provided with an operating amount detector 45 for detecting the operating amount of the attitude altering drive source 42. A detection value outputted from this operating amount detector 45 is outputted to an attitude detector 46. The attitude detector 46 is operable to detect the attitude inclined about the X-axis (FIG. 2B) of the distal end member 2, that is, to detect the attitude of the distal end member 2 that has been inclined about the X-axis. The attitude detector 46 includes a relation setting means (not shown), in which the relation between the output signal of the operating amount detector 45 and the attitude of the distal end member 2 inclined is set in terms of an arithmetic equation or table, and makes use of the relation setting means to detect the inclination in attitude in reference to the output signal inputted. This attitude detector 46 may be provided either in the controller 5 or in an external control device.

Also, the attitude altering drive mechanism 4c is provided with a supply power meter 47 for detecting the electric energy supplied to the attitude altering drive source 42, which is an electrically operated actuator. A detection value of this supply power meter 47 is outputted to a load detector 48. This load detector 48 in turn detects a load acting on the distal end member 2 in reference to an output of the supply power meter 47. This load detector 48 includes a relation setting means (not shown), in which the relation between the load and the output signal of the supply power meter 47 is set in terms of an arithmetic equation or table, and makes use of the relation setting means to detect the load in reference to the output signal so inputted. This load detector 48 may be provided either in the controller 5 or in an external control device.

The controller 5 referred to above is operable to control the tool rotation drive source 41 and the attitude altering drive source 42, based on the respective detection values outputted by the attitude detector 46 and the load detector 48.

The operation of the remote controlled actuator of the construction hereinabove described will now be described in detail.

When the tool rotating drive source 41 is driven, the rotational force thereof is transmitted to the spindle 13 through the rotary shaft 22 to thereby rotate the tool 1 together with the spindle 13. The load acting on the distal end member 2 when the tool 1 then being rotated cuts a bone or the like is detected from the detection value of the supply power meter 47 by the load detector 48. Accordingly, when the amount of feed of the remote controlled actuator in its entirety and the alteration of attitude of the distal end member 2, as will be described later, are controlled in dependence on the value of the load detected in the manner described above, cutting of the bone with the load acting on the distal end member 2 can be properly carried out while the load acting on the distal end member 2 is maintained properly.

During the use, the attitude altering drive source 42 is driven to alter the attitude of the distal end member 2 by remote control. By way of example, if the attitude altering member 31 is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 2A. If the attitude altering member 31 is conversely retracted by the attitude altering drive source 42, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 2A. At this time, a pressure from the attitude altering member 31, the elastic repulsive force from the restoring elastic member 32 and a reactive force from the constraint member 21 are applied to the distal end member coupling unit 15 and, depending on the balance of those applied forces, the attitude of the distal end member 2 is determined. The attitude of the distal end member 2 is detected by the attitude detector 46 from the detection value of the operating amount detector 45. For this reason, the attitude of the distal end member 2 can be properly controlled by remote control.

Also, since the rotation preventing mechanism 37 is provided for preventing the distal end member 2 from rotating about the center line CL relative to the spindle guide section 3, even when the distal end member 2 then holding the tool 1 becomes uncontrollable as a result of any trouble occurring in the attitude altering drive mechanism 4c for controlling the selective advance and retraction of the attitude altering member 31 and/or the control device therefor, it is possible to avoid the possibility that the site to be processed may be impaired as a result of rotation of the distal end member 2 about the center line CL or the distal end member 2 itself may be broken.

Since the attitude altering member 31 is inserted through the guide hole 30a of the guide pipe 30, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is made up of the wire 31a either and has a flexible property, the attitude altering operation of the distal end member 2 is carried out accurately even though the spindle guide section 3 is curved. In addition, since the center of the junction between the spindle 13 and the rotary shaft 22 lies at the same position as the respective centers of curvature O of the guide faces F1 and F3, no force tending to press and pull will not act on the rotary shaft 22 as a result of the alteration of the attitude of the distal end member 2 and the distal end member 2 can be smoothly altered in attitude.

The remote controlled actuator of the foregoing construction is utilized in grinding the femoral marrow cavity during, for example, the artificial joint replacement surgery and during the surgery, it is used with the distal end member 2 in its entirety or a part thereof inserted into the body of a patient. Because of this, if the distal end member 2 can be altered in attitude by remote control, the bone can be processed in a condition with the tool 1 maintained in a proper attitude at all times and the opening for insertion of the artificial joint can be finished accurately and precisely.

Since the spindle guide section 3 of the elongated shape includes the rotary shaft 22 provided in the center portion of the outer shell pipe 25, the guide pipe 30, in which the attitude altering member 31 is accommodated, and the reinforcement shaft 34, while the guide pipe 30 and reinforcement shaft 34 are arranged around the rotary shaft 22 so as to be juxtaposed in the circumferential locations spaced 180° in phase from each other, the arrangement balance of the rotary shaft 22, the guide pipe 30 and the reinforcement shaft 34 is rendered good.

Since the outer shell pipe 25 has a large wall thickness at its principal portion other than the grooved portions 24b, the rigidity (geometric moment of inertia) of the spindle guide section 3 is high. For this reason, not only can the positioning accuracy of the distal end member 2 be increased, but the cutting capability can also be increased. Also, since the guide pipe 30 and the reinforcement shaft 34 are arranged in the respective grooved portions 24b, positioning of the guide pipe 30 and the reinforcement shaft 34 in the circumferential direction can be facilitated, resulting in a good assemblability.

Since the outer diametric surfaces of the rolling bearings 26 supporting the rotary shaft 22 are supported by the guide pipe 30 and the reinforcement shafts 34, the outer diametric surfaces of the rolling bearings 26 can be supported with no need to use any extra member. Also, since the preload is applied to the rolling bearings 26 by means of the spring elements 27A and 27B, the rotary shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

Figures 6A, 6B:
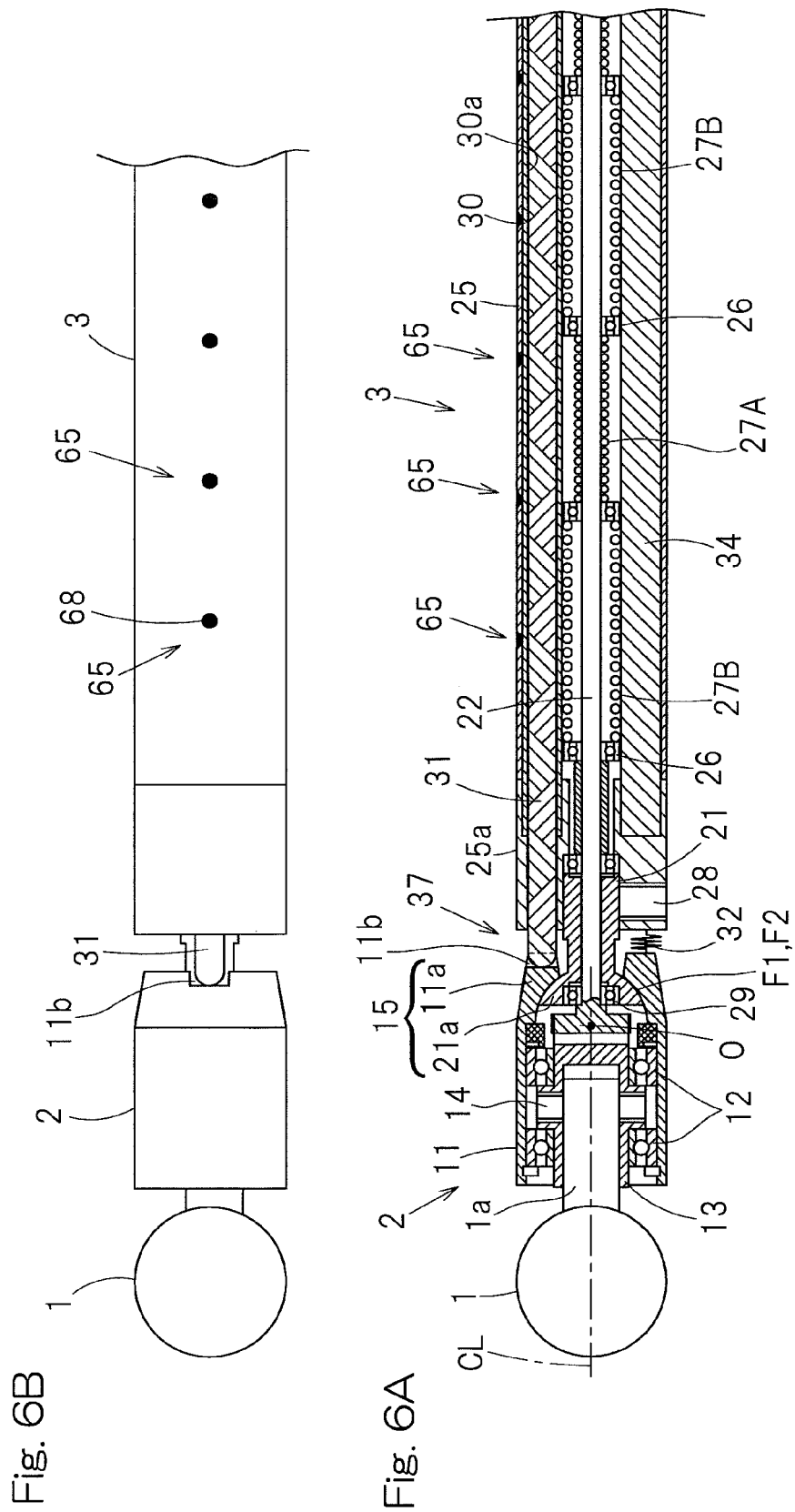
FIG. 6A is a longitudinal sectional view showing the distal end member and the spindle guide section, both employed in the remote controlled actuator according to a third preferred embodiment of the present invention.
FIG. 6B is a plan view of FIG. 6A.

In order to further increase the rigidity of the spindle guide section 3, it is recommended to fix the outer shell pipe 25 and the guide pipe 30 by means of a pipe fixture segment 65 such as shown in FIGS. 5A and 5B pertaining to a second preferred embodiment of the present invention or in FIGS. 6A and 6B pertaining to a third preferred embodiment of the present invention. The pipe fixture segment 65 shown in FIGS. 5A and 5B and employed in the practice of the second embodiment is such that openings 66 is provided in a peripheral wall of the outer shell pipe 25 so as to extend from inside to outside thereacross and portions of the outer shell pipe 25 around the openings 66 are fixed to the guide pipe 30 by means of solder or weld at locations 67. The pipe fixture segment 65 shown in FIGS. 6A and 6B and employed in the practice of the third embodiment of the present invention is such that the outer shell pipe 25 and the guide pipe 30 are fixed together by means of laser weld at locations 68 from an outer diametric surface side of the outer shell pipe 25. With either of those pipe fixture segments 65, the outer shell pipe 25 and the guide pipe 30 can be relatively easily and firmly fixed together. In particular, as compared with the former, the latter does not require formation of the openings 66 in the outer shell pipe 25 and is, therefore, effective to still further increase the rigidity of the spindle guide section, accompanied by an increase of the assemblability.

It is to be noted that although not shown in the accompanying drawings, the outer shell pipe 25 and the reinforcement shaft 34 may be fixed together in a manner similar to that described above and even in this case, the rigidity of the spindle guide section 3 can be increased similarly.

Figure 4:
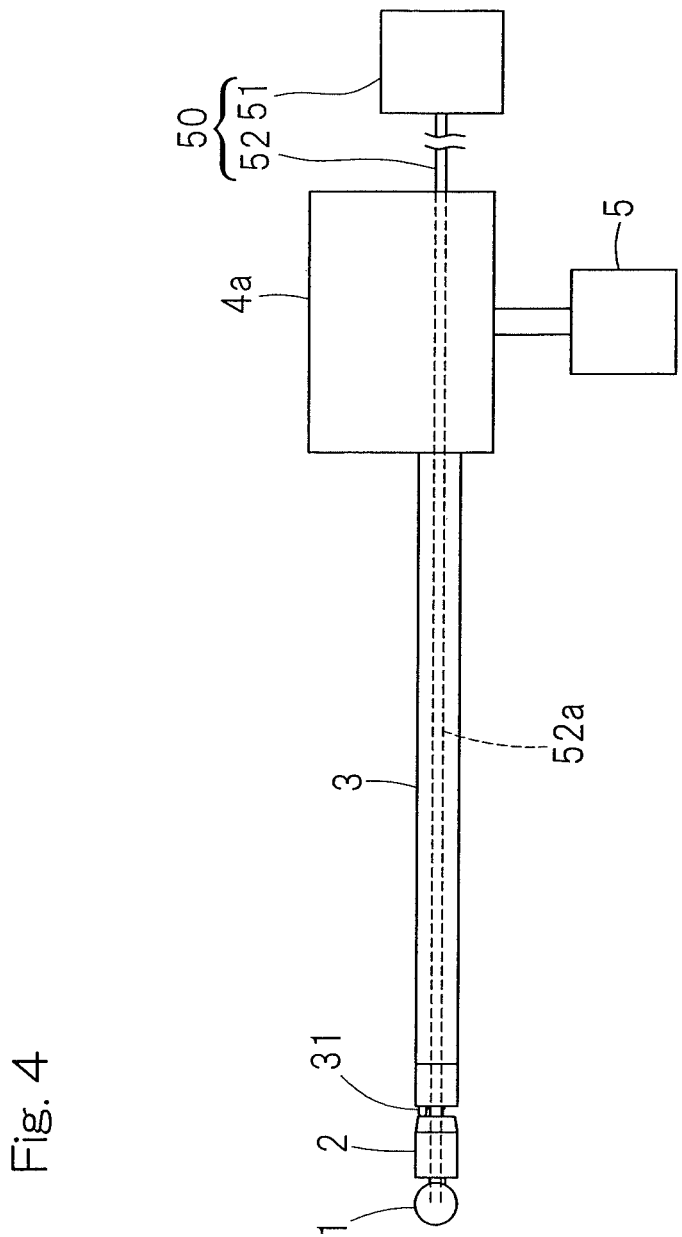
FIG. 4 is a diagram showing the schematic structure, which is applicable where the remote controlled actuator in FIG. 1 is provided with a cooling unit.

In view of the spindle guide section 3 being of a hollow shape, the remote controlled actuator of the present invention can be provided with a cooling unit 50 for cooling the tool 1 as shown in FIG. 4. In other words, the cooling unit 50 includes a liquid coolant supply device 51, provided outside the drive unit housing 4a, and a liquid coolant supply passage or tube 52 for guiding a liquid coolant from the liquid coolant supply device 51 towards the tool 1 through the drive unit housing 4a, the spindle guide section 3 and the interior of the distal end member 2. A portion 52a of the liquid coolant supply passage 52, which extends within the spindle guide section 3, is constituted by the outer shell pipe 25 itself serving as the liquid coolant supply passage 52 and the liquid coolant flows through an interior of the outer shell pipe 25 accordingly. The liquid coolant guided to the tool 1 is discharged to an outer periphery of the tool 1. If the cooling unit 50 is provided in this way, heat emitting areas such as, for example, the tool 1, a to-be-processed article, the spindle 13, the rotary shaft 22 and the bearings 26 and 29 can be cooled. Since the liquid coolant is passed through the outer shell pipe 25, there is no need to use any extra tube for the purpose of supplying the liquid coolant and the spindle guide section 3 can therefore be simplified and made small in diameter. Also, the liquid coolant may be concurrently used for lubrication of the rolling bearings 26 and 29. By so doing, the use of a grease or the like, which is generally used, can be dispensed with and, also, there is no need to use any extra lubricating device. It is to be noted that a liquid coolant recirculating system may be designed, in which the liquid coolant once guided to the tool 1 is returned to the liquid coolant supply device 51 without being discharged to the outer periphery of the tool 1. It is, however, noted that where the flow of the liquid coolant passing through the outer shell pipe 25 is small, an extra liquid coolant has to be supplied from the outside to cool the tool 1 and the to-be-processed article.

The liquid coolant referred to above is preferably in the form of water or physiological saline. If the liquid coolant is employed in the form of water or physiological saline, the liquid coolant will bring no adverse influence on the living body when the processing is performed with the distal end member 2 inserted into the living body. Where water or physiological saline is employed for the liquid coolant, component parts, with which the liquid coolant contacts, are preferably made of stainless steel that is excellent in resistance to corrosion. Any other component parts forming the remote controlled actuator may be made of stainless steel.

Although in the above described embodiments, the attitude alteration of the distal end member 2 is accomplished when the attitude altering member 31 presses the housing 11, such as in a fourth preferred embodiment of the present invention shown in FIGS. 7A to 7C, the tip end of the attitude altering member 31 in the form of the wire and the housing 11 are connected with each other by means of a connecting member 31a so that when the attitude altering member 31 is retracted towards the base end side by an attitude altering drive source (not shown), the housing 11 can be pulled by the attitude altering member 31 to allow the distal end member 2 to be altered in attitude. In such case, the restoring elastic member 32 is employed in the form of a tensile coil spring.

FIGS. 8A to 8C illustrate a fifth preferred embodiment of the present invention. The remote controlled actuator according to this fifth embodiment is similar to the remote controlled actuator according to the first embodiment of the present invention shown in and described with particular reference to FIGS. 3A and 3B, but differs therefrom in that in place of the reinforcement shaft 34, a guide pipe 30 is provided and the attitude altering member 31 is reciprocally movably inserted within a guide hole 30a forming an inner diametric hole of the guide pipe 30. In other words, two sets of the guide pipes 30 and the attitude altering members 31 are arranged at respective circumferential locations spaced 180° in phase from each other. No restoring elastic member 32 is provided. The guide faces F1 and F2 are spherical surfaces each having the center of curvature lying at the point O or cylindrical surfaces each having a lateral X-axis as a longitudinal axis passing through the point O.

The drive unit 4 (not shown in FIGS. 8A to 8C) is provided with two attitude altering drive sources 42 (not shown in FIGS. 8A to 8B) for selectively advancing and retracting respective attitude altering members 31 so that when those two attitude altering drive sources 42 are driven in respective directions opposite to each other, the distal end member 2 can be altered in attitude. By way of example, when the upper attitude altering member 31 shown in FIG. 8A is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards as viewed in FIG. 8A. Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 8A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces. According to this construction, since the housing 11 for the distal end member 2 is pressed by the two attitude altering members 31, as compared with the previously described embodiment in which it is pressed by the only attitude altering member 31, the attitude stability of the distal end member 2 can be increased.

Figure 9A:
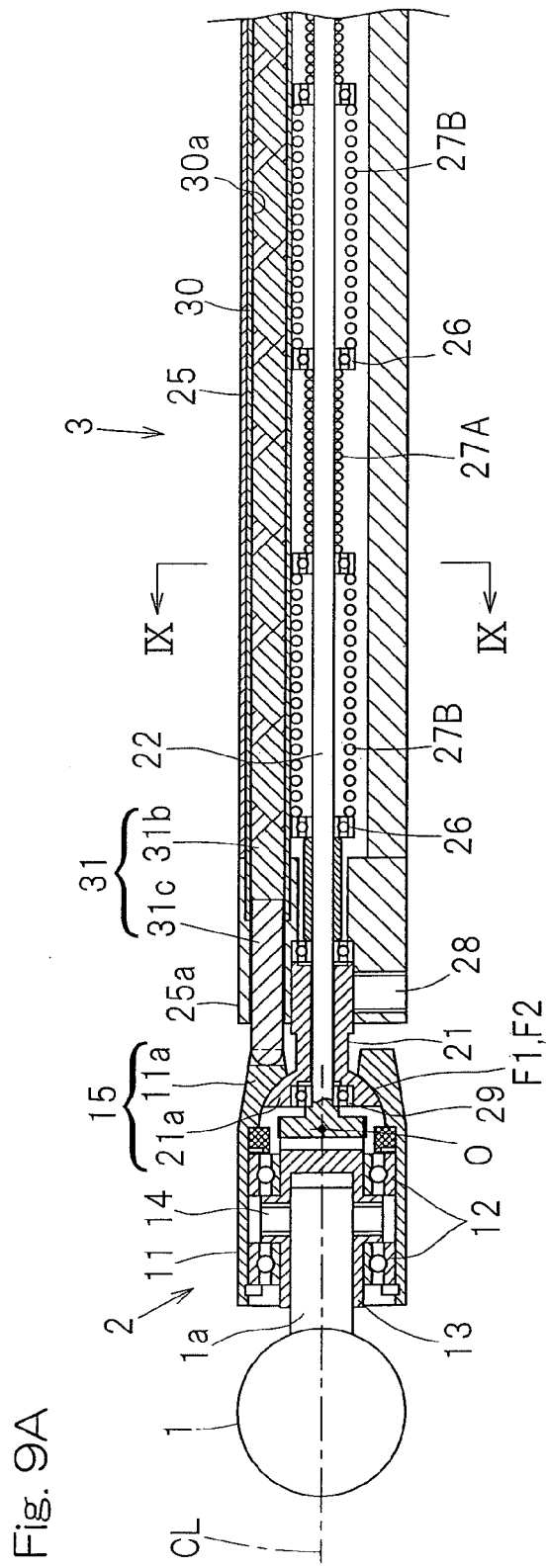
FIG. 9A is a longitudinal sectional view showing the distal end member and the spindle guide section, both employed in the remote controlled actuator according to a sixth preferred embodiment of the present invention.
Figure 9C:
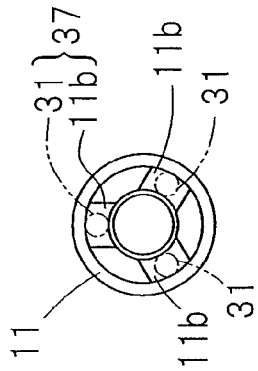
FIG. 9C is a view as viewed from the base end side of the housing for the distal end member.
Figure 9B:
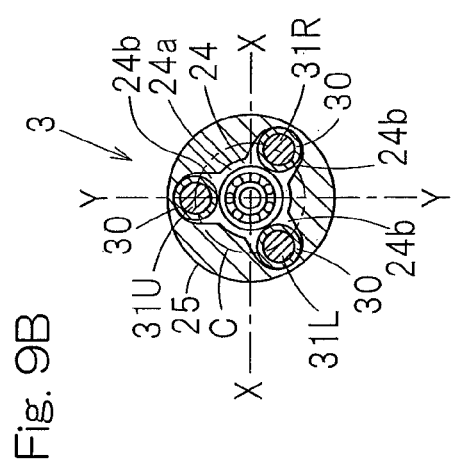
FIG. 9B is a cross sectional view taken along the line IX-IX in FIG. 9A.

FIGS. 9A to 9C illustrate a sixth preferred embodiment of the present invention. In the remote controlled actuator according to this sixth embodiment the hollow 24 of the outer shell pipe 25 is made up of a round hole portion 24a at a center portion thereof and three grooved portions 24b radially outwardly depressed from respective circumferential locations of an outer periphery of the round hole portion 24a, which locations form a 120° phase relative to each other. The guide pipes 30 are arranged in the respective grooved portions 24b, and the attitude altering members 31 are accommodated within respective guide holes 30a, which are inner diametric holes of those guide pipes 30, for reciprocal movement relative to the associated guide pipes 30. In this embodiment, the attitude altering members 31 is made up of the wire 31a and the pillar shaped pins 31c. The pillar shaped pins 31c has a tip end representing a spherical shape which is held in contact with a bottom face of the radical groove portion 1b formed in a base end face of the housing 11. No restoring elastic member 32 is provided. The guide surfaces F1 and F2 represents spherical surface having respective centers of curvature lying at the point O and the distal end member 2 can be tilted in any desired direction.

The drive unit 4 is provided with three attitude altering drive sources 42 (42U, 42L and 42R) (FIG. 12) for reciprocally operating respective attitude altering members 31 (31U, 31L and 31R), and those attitude altering drive sources 42 cooperate with each other to drive the distal end member 2 to alter the attitude thereof.

By way of example, when one of the attitude altering members 31U, which is shown in an upper side of FIGS. 9A to 9C, is advanced towards the tip end side while the other two attitude altering members 31L and 31R are retracted, the housing 11 for the distal end member 2 is pressed by the upper attitude altering member 31U to allow the distal end member 2 to be altered in attitude along the guide surfaces F1 and F2 with the tip end side consequently oriented downwardly as viewed in FIG. 9A. At this time, those attitude altering drive sources 42 are controlled so that the amount of advance or retraction of each of the attitude altering members 31 may become proper. On the other hand, when each of those attitude altering members 31 is conversely retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 9A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 9A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased. It is, however, to be noted that if the number of the attitude altering members 31 used is increased, the attitude stability of the distal end member 2 can be still further increased.

Figure 10A:
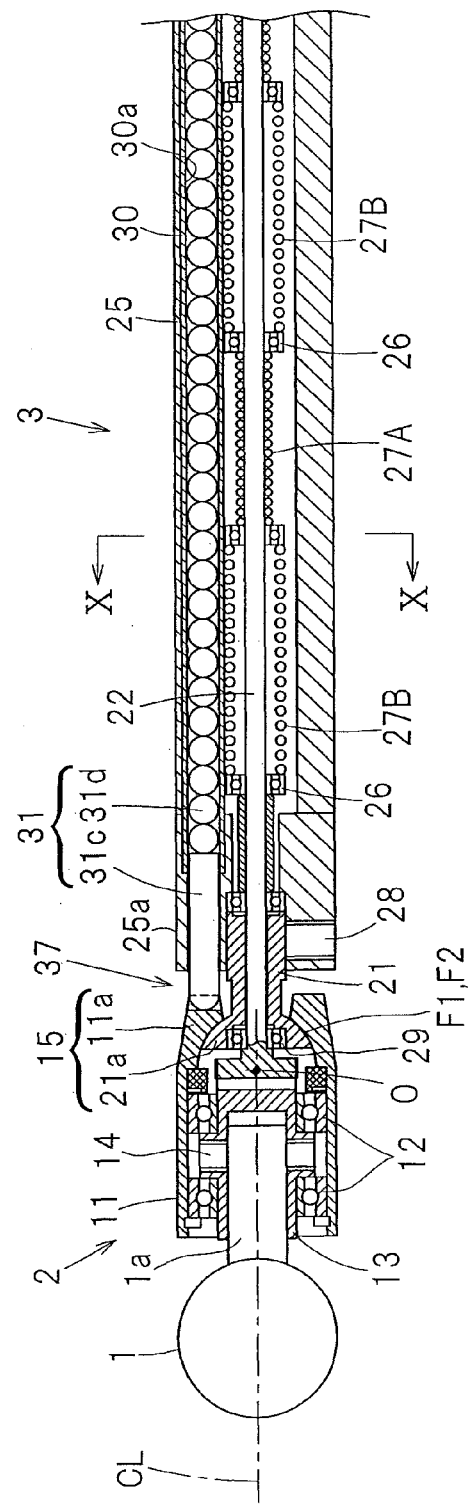
FIG. 10A is a longitudinal sectional view showing the distal end member and the spindle guide section, both employed in the remote controlled actuator according to a seventh preferred embodiment of the present invention.
Figure 10C:
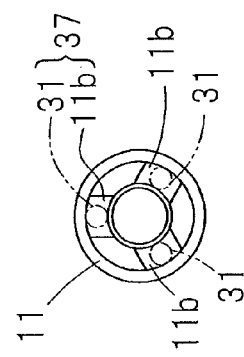
FIG. 10C is a view as viewed from the base end side of the housing for the distal end member.
Figure 10B:
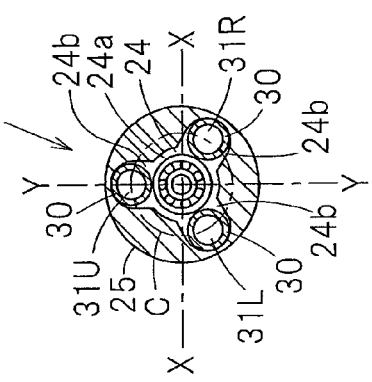
FIG. 10B is a cross sectional view taken along the line X-X in FIG. 10A.

The attitude altering member 31 may be constituted by a row of force transmitting members that are arranged in a lengthwise direction of the guide hole 30a with no gap formed between the neighboring force transmitting members such as shown in FIGS. 10A to 10C, which pertain to a seventh preferred embodiment of the present invention, or in FIGS. 11A to 11C which pertain to an eighth preferred embodiment of the present invention. In the example shown in FIGS. 10A to 10C, the row of the force transmitting members are employed in the form of balls 31d and a pillar shaped pin 31c is disposed on a distal end side of the row of those balls 31d. In the example shown in FIGS. 11A to 11C, the row of the force transmitting members are employed in the form of pillar shaped elements 31e such as, for example, cylinders and a pillar shaped pin 31c is disposed on the distal end side of the row of those pillar shaped elements 31e. The pillar shaped pin 31c is the one similar to that described hereinbefore and has a spherical tip end held in engagement with the bottom face of the radial groove portion 11b formed in the base end face of the housing 11.

Where the attitude altering member 31 is constituted by the plural force transmitting members 31d and 31e as hereinabove described, the attitude of the distal end member 2 can be altered by operating the tip end of the attitude altering member 31 toward the side in which the distal end member 2 is pressed. Accordingly, even though the attitude altering member 31 is constituted by the plural force transmitting members 31d and 31e, it is possible to assuredly bring the work on the distal end member 2. Since the force transmitting members 31d and 31e are arranged within the guide hole 30a, the distal end member 2 can be worked on properly at all times without the attitude altering member 31 displacing in position in a direction transverse to the longitudinal direction thereof, and the attitude alteration of the distal end member 2 can be accomplished accurately. Also, even though the individual force transmitting members 31d and 31e are rigid elements, the attitude alteration of the distal end member 2 can be accomplished assuredly even in the case of the curved spindle guide section 3 since the attitude altering member 31 as a whole is flexible.

Figure 12:
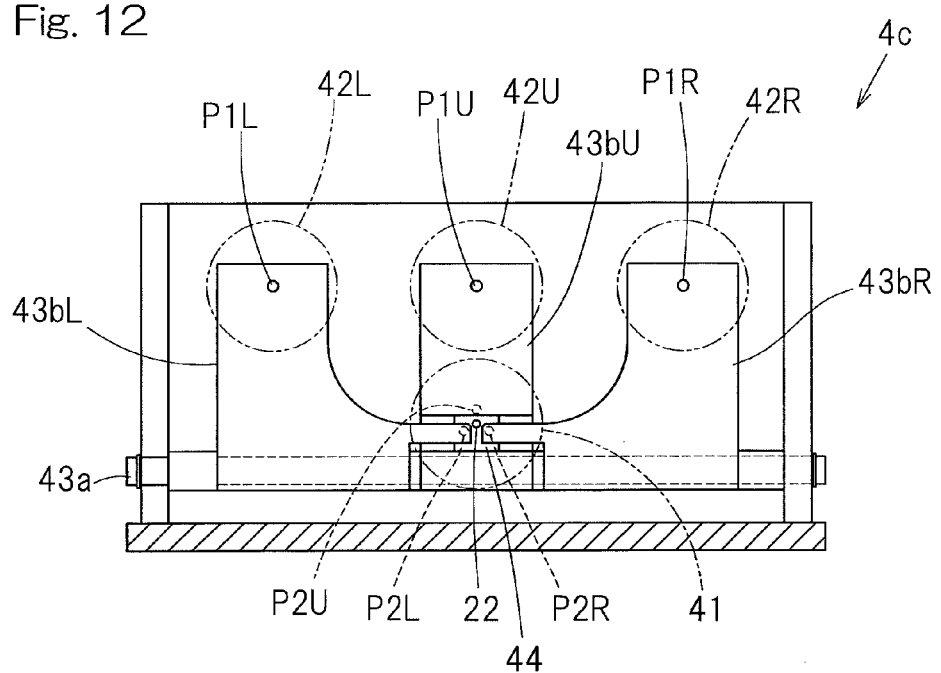
FIG. 12 is a fragmentary front view, with a portion cut out, showing the tool rotating drive mechanism and the attitude altering drive mechanism, both employed in the remote controlled actuator shown in FIGS. 9A to 9C, FIGS. 10A to 10C and FIGS. 11A to 11C.

Although FIGS. 10A to 10C and FIGS. 11A to 11C have been shown and described as illustrating respective examples in which the attitude altering member 31 is provided at three circumferential locations spaced 120° in phase from each other, the use of the attitude altering member 31 made up of the plural force transmitting members 31d and 31e can be made even where the attitude altering member 31 is provided at two circumferential locations spaced 180° in phase from each other and, also, where a combination of the attitude altering member 31, provided at one circumferential location, with the corresponding restoring elastic member 32 is made.

Where the attitude altering members 31 are provided at the three circumferential locations such as in any one of the examples shown and described with reference to FIGS. 9A to 9C, FIGS. 10A to 10C, and FIGS. 11A to 11C, respectively, the attitude altering drive mechanism 4c may be constructed, for example, such as shown in FIG. 12. In other words, the attitude altering drive mechanism 4c is so constructed that the three attitude altering drive sources 42 (42U, 42L and 42R) for selectively advancing and retracting the attitude altering members 31 (31U, 31L and 31R) may be arranged along a leftward and rightward direction and parallel to each other. Levers 43b (43bU, 43bL and 43bR) corresponding to the attitude altering drive sources 42 may be provided for pivotal movement about a common support pin 43a to enable the force of the output rod 42a (42aU, 42aL and 42aR) of each of the attitude altering drive sources 42 to work on the point P1 (P1U, P1L and P1R) of the respective lever 43b, which is spaced a long distance from the support pin 43a, and to enable the force to work on the attitude altering member 31 at the point P2 (P2U, P2L and P2R), which is spaced a short distance from the support pin 43a. Accordingly, the output of each of the attitude altering drive sources 42 can be increased and then transmitted to the corresponding attitude altering member 31. It is to be noted that the rotary shaft 22 is passed through an opening 44 defined in the lever 43bU for the attitude altering member 31U on the upper side.

Figure 13:
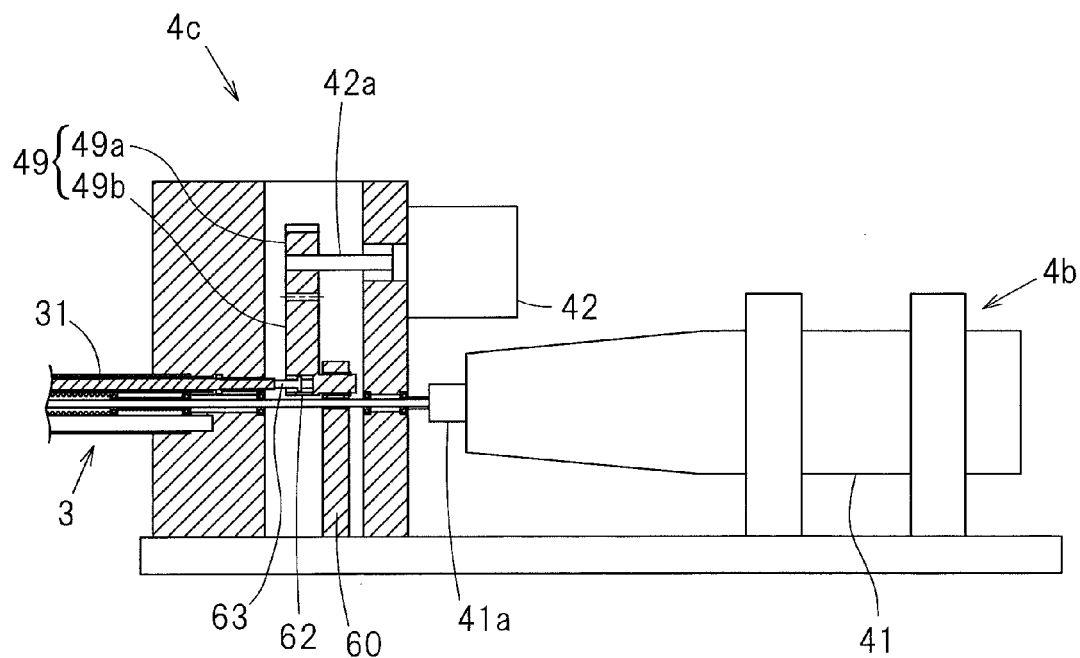
FIG. 13 is a fragmentary side view, with a portion cut out, showing the tool rotating drive mechanism and the attitude altering drive mechanism, both employed in the remote controlled actuator employing the attitude altering drive mechanism of a different structure.
Figure 14:
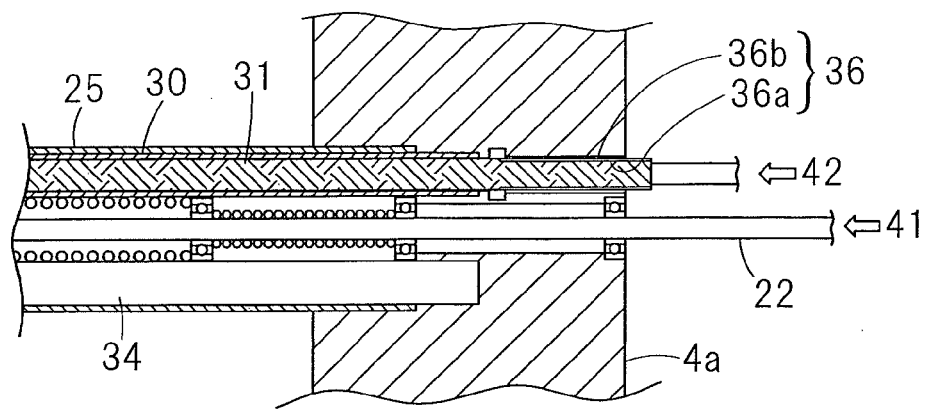
FIG. 14 is a longitudinal sectional view showing, on an enlarged scale, a connection area between an attitude operating or altering member and a drive unit housing, both employed in the remote controlled actuator.

FIG. 13 illustrates a side view, with a portion cut out, of the tool rotating drive mechanism 4b and the attitude altering drive mechanism 4c of the remote controlled actuator of a type utilizing the attitude altering drive mechanism of a different structure and FIG. 14 illustrates an enlarged view showing a connecting unit between the attitude altering member 31 and the drive unit housing 4a. In this example, a male screw portion 36a is formed in the base end of the attitude altering member 31 composed of a wire and is threadingly engaged with a female screw portion 36b formed in the drive unit housing 4a. The male screw portion 36a and the female screw portion 36b altogether constitute a screw mechanism 36. Hence, the attitude altering member 31 is selectively advanced and retracted one at a time by the action of the screw mechanism 36, when the base end of the attitude altering member 31 is rotated by the drive of the attitude altering drive source 42.

The attitude altering drive mechanism 4c is such that the rotation of the output shaft 42a of the attitude altering drive source 42, which is in the form of, for example, an electrically operated rotary actuator, is reduced in speed and transmitted to the base end of the attitude altering member 31 through a rotation reducing and transmitting mechanism 49. The rotation reducing and transmitting mechanism 49 includes a round spur gear 49a, mounted on the output shaft 42a of the attitude altering drive source 42, and a sector shaped spur gear 49b rotatably mounted on a support member 60, which is fixed to the drive unit housing 4a, and meshed with the round spur gear 49a and is so designed and so configured as to transmit rotation from the sector shaped spur gear 49b to a base end side extension 63 of the attitude altering member 31 at a rotary sliding unit 62 provided on the axis of rotation of the sector shaped gear 49b. The sector shaped spur gear 49b has a larger pitch circle diameter than that of the round spur gear 49a so that the rotation of the output shaft 42a can be transmitted to the base end of the attitude altering wire 31a after having been reduced in speed. Since the use of the rotation reducing and transmitting mechanism 49 is effective even in a compact rotary actuator of a type rotatable at a high speed to rotate the base end of the attitude altering member 31 at a low speed, such compact rotary actuator can be employed as the attitude altering drive source 42. The tool rotating drive mechanism 4b is similar in structure to that hereinbefore described.

Figure 15:
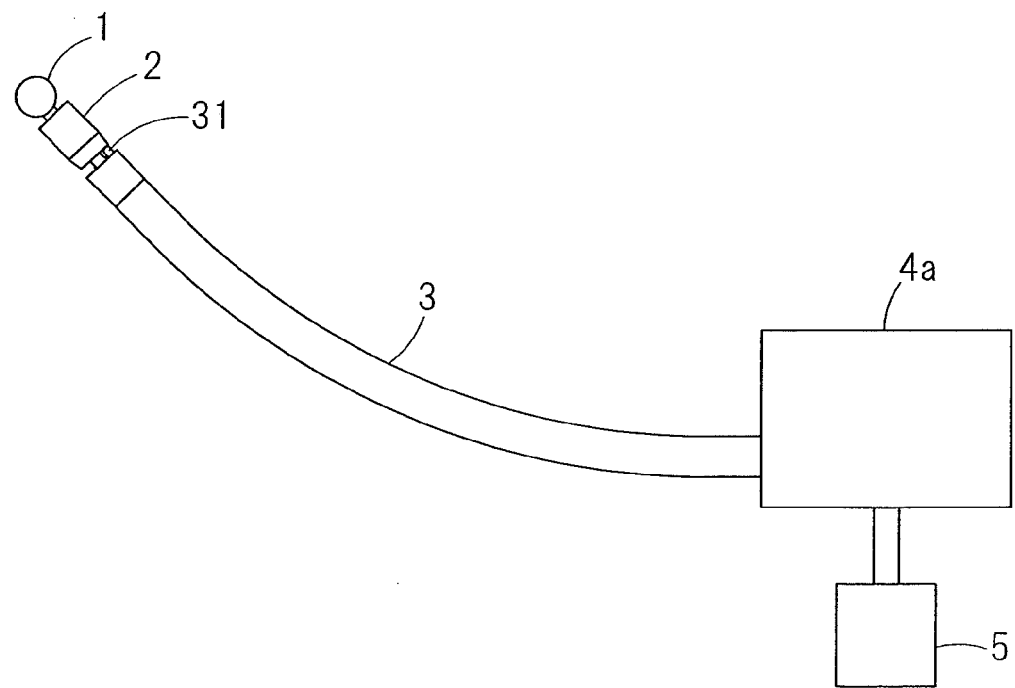
FIG. 15 is a diagram showing a schematic structure of the remote controlled actuator employing the spindle guide section of a different shape.

While in any one of the foregoing embodiments the spindle guide section 3 has been shown and described as extending straight, since the remote controlled actuator of the present invention is such that the attitude altering member 31 has a flexibility and, even when the spindle guide section 3 is curved, the attitude alteration of the distal end member 2 take place assuredly, the spindle guide section 3 may have a curved shape in an initial condition as shown in FIG. 15. Alternatively, only a portion of the spindle guide section 3 may have a curved shape. If the spindle guide section 3 has a curved shape, it may happen that insertion of the distal end member 2 deep into the bore, where the spindle guide section of the straight shape fails to reach, can be accomplished, and, therefore, the processing of the opening for insertion of the artificial joint prior to a surgery being performed to replace with the artificial joint can be formed precisely and accurately.

Where the spindle guide section 3 is designed to represent the curved shape, the outer shell pipe 25, the guide pipes 30 and the reinforcement shafts 34 need be curved in shape. Also, an easily deformable material is preferably used for the rotary shaft 22 and a shape memory alloy, for example, can be suitably employed therefor.

In the next place, first to seventh applied cases, in which the hollow 24 having the round hole portion 24a and the grooved portions 24b is not provided, will be described.

In any one of the foregoing embodiments of the present invention, the outer shell pipe 25 forming the outer shell for the spindle guide section 3 has been shown and described as having the hollow 24 including the round center hole portion 24a at the center thereof and the grooved portions 24b that are radially outwardly depressed from the respective circumferential locations and situated on the outer periphery of the round hole portion 24a. In contrast thereto, in any one of the first to seventh applied cases which will now be described, the outer shell pipe 25, although being in the form of a hollow pipe, is provided with neither the round hole portion 24a nor the grooved portions 24b and the rotary shaft 22 is positioned at the center of this outer shell pipe 25. Between the inner diametric surface of the outer shell pipe 25 and the rotary shaft 22, the guide pipe 30 or a plurality of reinforcement shafts 34 is/are arranged on the pitch circle C of the same diameter. The guide pipe 30 and the reinforcement shafts 34 are arranged equidistantly relative to each other. The guide pipe 30 and the reinforcement shafts 34 are held in contact with the inner diametric surface of the outer shell pipe 25 and respective outer diametric surfaces of the rolling bearings 26. In this manner, the outer diametric surfaces of those rolling bearings 26 are supported.

Any one of the first to seventh applied cases makes use of a cooling unit 50 having an interior, into which a coolant liquid is injected through a coolant liquid injecting hole 75 defined in the vicinity of the base end of the spindle guide section 3, and capable of feeding it towards the tip end side through the interiors of both the spindle guide section 3 and the distal end member 2 and finally discharging it from the distal end member 2 towards the tool 1.

It is to be noted that in each of the first to seventh applied cases, component parts employed therein and similar to those referred to in the foregoing description are designated by like reference numerals and the details thereof are not reiterated for the sake of brevity.

The first applied case of the present invention will be described in detail with particular reference to FIGS. 16 to 18. This first applied case corresponds to the first embodiment of the present invention shown and described with particular reference to FIG. 1 to FIGS. 3A and 3B.

Figure 16:
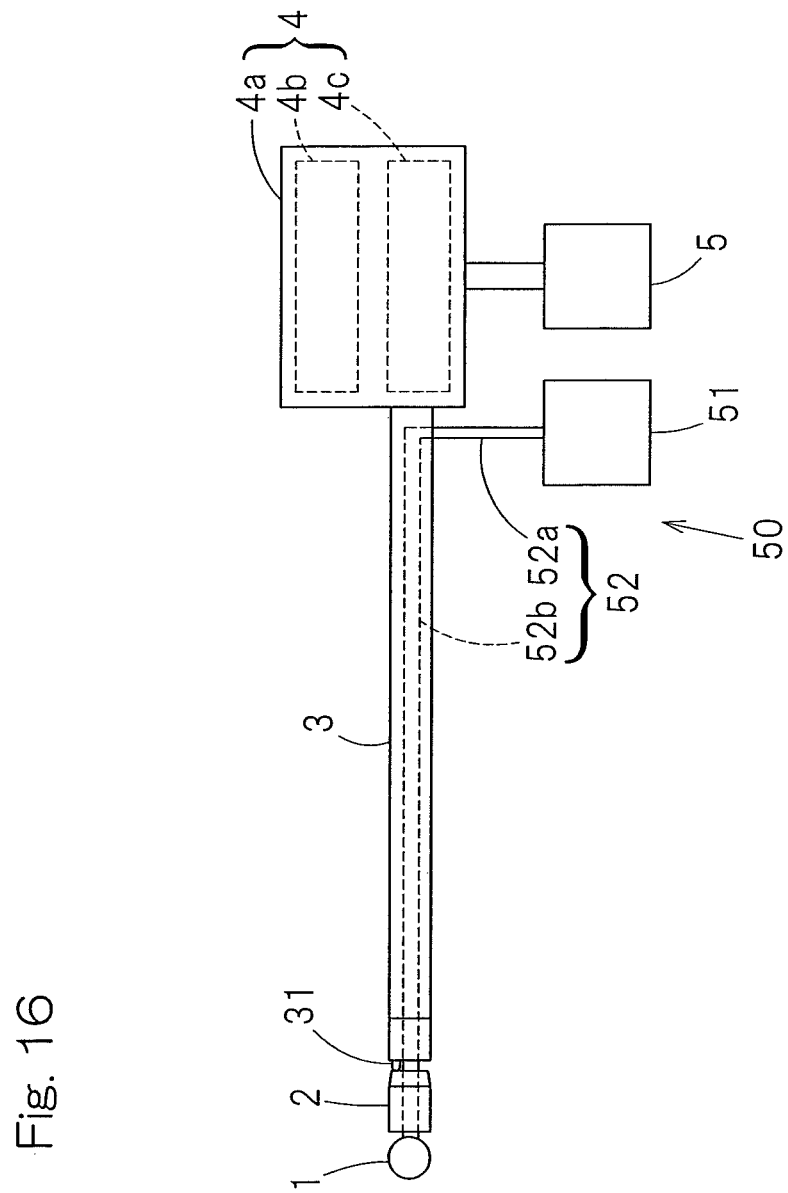
FIG. 16 is a diagram showing a schematic structure of the remote controlled actuator according to a first applied case of the present invention.
Figure 17:
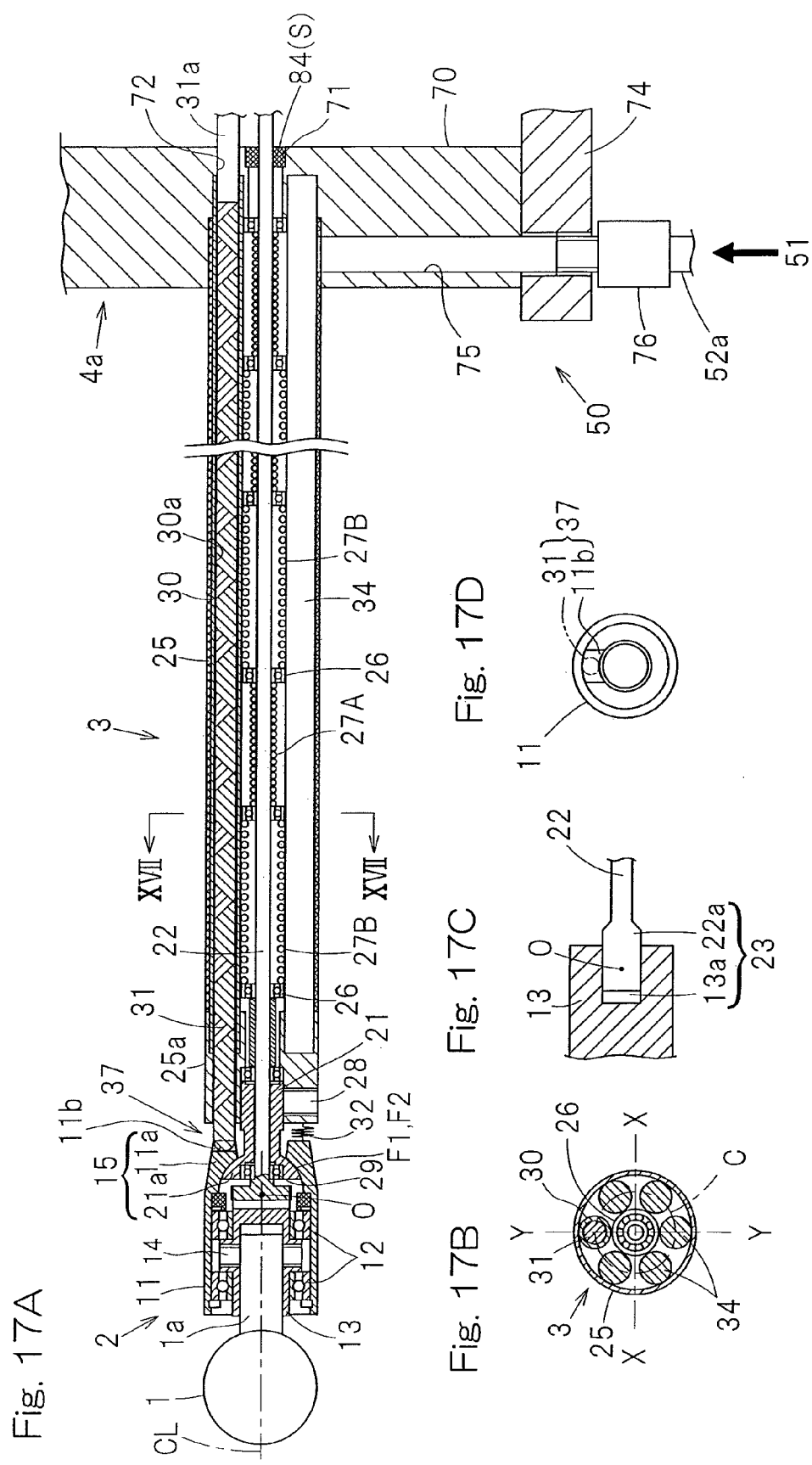
FIG. 17A is a longitudinal sectional view showing the distal end member, the spindle guide section and a portion of the drive unit housing, all employed in the remote controlled actuator.
FIG. 17B is a cross sectional view taken along the line XVII-XVII in FIG. 17A.
FIG. 17C is a diagram showing a coupling structure between the distal end member and the rotary shaft.
FIG. 17D is a view as viewed from the base end side of the housing for the distal end member.

Referring first to FIG. 16, the cooling unit 50 includes a coolant liquid supply device 51 provided outside the remote controlled actuator and a coolant liquid supply passage or tube 52 for supplying a coolant liquid, fed from the coolant liquid supply device 51, towards the tip end side through the interiors of the spindle guide section 3 and the distal end member 2 and is capable of discharging the coolant liquid from a tip end of the distal end member 2 towards the tool 1 in the axial direction. The coolant liquid supply passage 52 is made up of an outer passage portion 52a, extending from the coolant liquid supply device 51 to the spindle guide section 3, and an inner passage portion 52b extending through the interiors of the spindle guide section 3 and the distal end member 2, and in the inner passage portion 52b, the outer shell pipe 25 (FIGS. 17A to 17D) of the spindle guide section 3 and the housing 11 (FIGS. 17A to 17D) for the distal end member 2 form the coolant liquid supply passage 52.

As best shown in FIG. 17A, the spindle guide section 3 has its base end portion inserted into a side plate 70 on the tip end side of the housing and then coupled with the drive unit housing 4a. The side plate 70 of the drive unit housing 4a is provided with a bearing mounting hole 71 coaxial with the axis of the spindle guide section 3 and an extended guide hole 72 that is continued from the guide hole 30a. A slide bearing 84 is disposed inside the bearing mounting hole 71, with the rotary shaft 22 supported by the slide bearing 84. The extended guide hole 72 has the pillar shaped pin 31c inserted therethrough.

Also, the coolant liquid injecting hole 75 communicating between the inside of the spindle guide section 3 and the outside is provided in the side plate 70 and a substrate 74 of the drive unit housing 4a and the outer passage portion 52a of the coolant liquid supply passage 52 is coupled with an outer side end of the coolant liquid injecting hole 75 through a coupling member 76. The slide bearing 84 is disposed on the base end side of the coolant liquid injecting hole 75. The slide bearing 84 referred to previously is a sealing unit S for avoiding an undesirable ingress of the coolant liquid from the inside of the spindle guide section 3 into the inside of the drive unit housing 4a.

Figure 18:
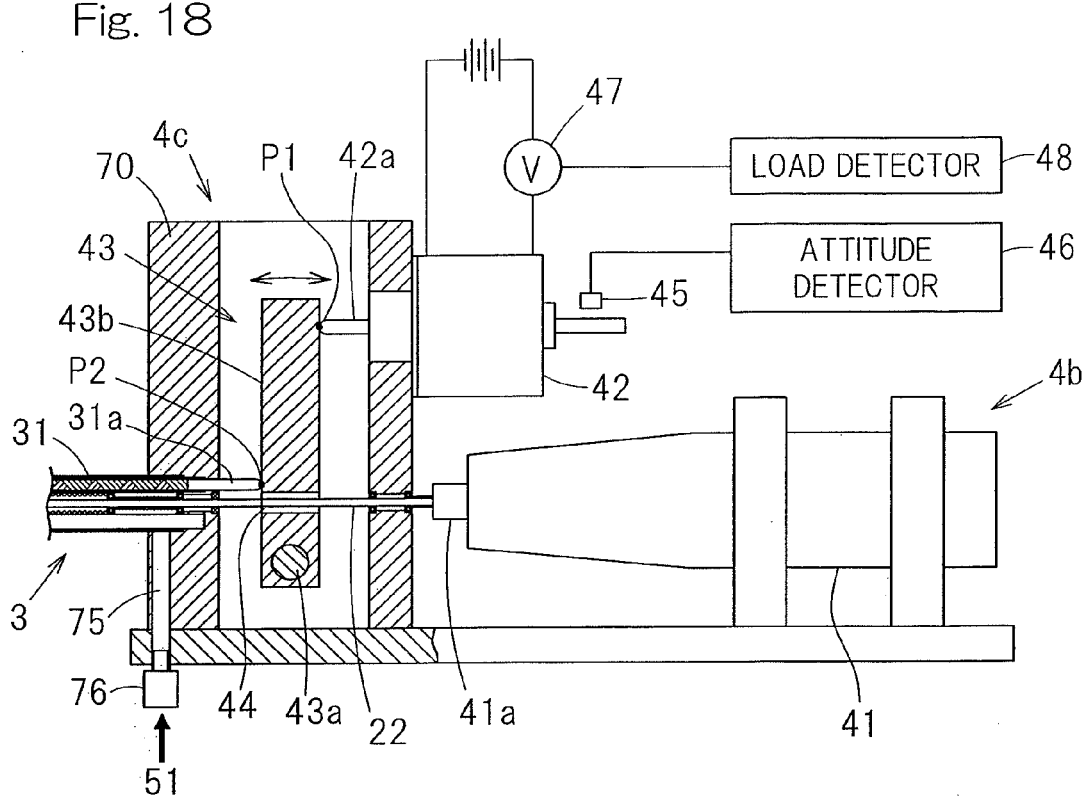
FIG. 18 is a diagram showing a side view of the tool rotating drive mechanism and the attitude altering drive mechanism, both employed in the remote controlled actuator, shown together with the control system.

FIG. 18 illustrates the tool rotating drive mechanism 4b and the attitude altering drive mechanism 4c both accommodated within the drive unit housing 4a. FIG. 18 corresponds to FIGS. 3A and 3B, and other structural features excluding the presence or absence of the coolant liquid supply device 51, which forms the cooling unit 50, are similar to those shown in and described with reference to FIGS. 3A and 3B and, therefore, the details thereof are not reiterated for the sake of brevity.

The operation of the remote controlled actuator according to this first applied case of the present invention is similar to that in the previously described first embodiment of the present invention and, therefore, only the difference between the both will be described.

The spindle guide section 3 of an elongated configuration requires the rotary shaft 22 and the attitude altering member 31 to be provided therein in a protected fashion. Since the rotary shaft 22 is provided at the center of the outer shell pipe 25 and the guide pipe 30, accommodating the attitude altering member 31 therein, and the reinforcement shafts 34 are positioned between the outer shell pipe 25 and the rotary shaft 22 and juxtaposed relative to each other in the circumferential direction, the rotary shaft 22 and the attitude altering member 31 are thus protected and also the interior can be made hollow to thereby reduce the weight without sacrificing the rigidity. Also, the arrangement balance as a whole is rendered good.

By the action of the cooling unit 50, the coolant liquid supplied from the coolant liquid supply device 51 flows from the coolant liquid injecting hole 75 into the inside of the spindle guide section 3 and then towards the tip end side after having flowed through the interiors of the spindle guide section 3 and the distal end member 2 before it is discharged in the axial direction from the tip end of the distal end member 2 towards the tool 1. More specifically, within the interior of the spindle guide section 3, the coolant liquid flows through a hollow area between the rotary shaft 22, the guide pipe 30 and the reinforcement shaft 34 within the outer shell pipe 25 and a gap between inner and outer rings of the rolling bearings 26. Over the range from the spindle guide section 3 to the distal end member 2, the coolant liquid flows through a gap, delimited between the constraint member 21 and the rotary shaft 22, and a gap delimited between inner and outer rings of the rolling bearings 29. Within the interior of the distal end member 2, the coolant liquid flows through a gap delimited between inner and outer rings of the bearing 12.

When the coolant liquid flows through the interiors of the spindle guide section 3 and the distal end member 2, the rotary shaft 22, the rolling bearings 26 and 29 and the spindle 13 are cooled. Those rotatable members tend to emit heat under the influence of friction occurring during the rotation. Also, by the action of the coolant liquid discharged from the distal end member 2, the tool 1 and an article to be processed are cooled. In this way, as a result of the flow of the coolant liquid through the interiors of the spindle guide section 3 and the distal end member 2, there is no need to provide the outside with any tube for the supply of the coolant liquid, and therefore, the spindle guide section 3 and the distal end member 2 can be simplified and downsized.

It is to be noted that the coolant liquid may be concurrently used for lubrication of the rolling bearings 26 and 29. By so doing, there is no need to use any grease or the like that is generally utilized in bearings and, moreover, there is no need to employ an extra lubricating device.

In general, since the slide bearing supports the rotary shaft in a contact fashion, a gap in a rotatable area between the bearing and the rotary shaft is small as compared with that in the rolling bearing. For this reason, if a bearing used to support the rotary shaft 22 on the base end side of the coolant liquid injecting hole 75 is employed in the form of the slide bearing 84, an undesirable ingress of the coolant liquid from the spindle guide section 3 into the interior of the drive unit housing 4a is avoided. In other words, the slide bearing 84 can be concurrently used as the sealing unit S. By the provision of the sealing unit S, any trouble will hardly occur in the tool rotating drive mechanism 4b and the attitude altering drive mechanism 4c both housed within the drive unit housing 4a.

Figure 19:
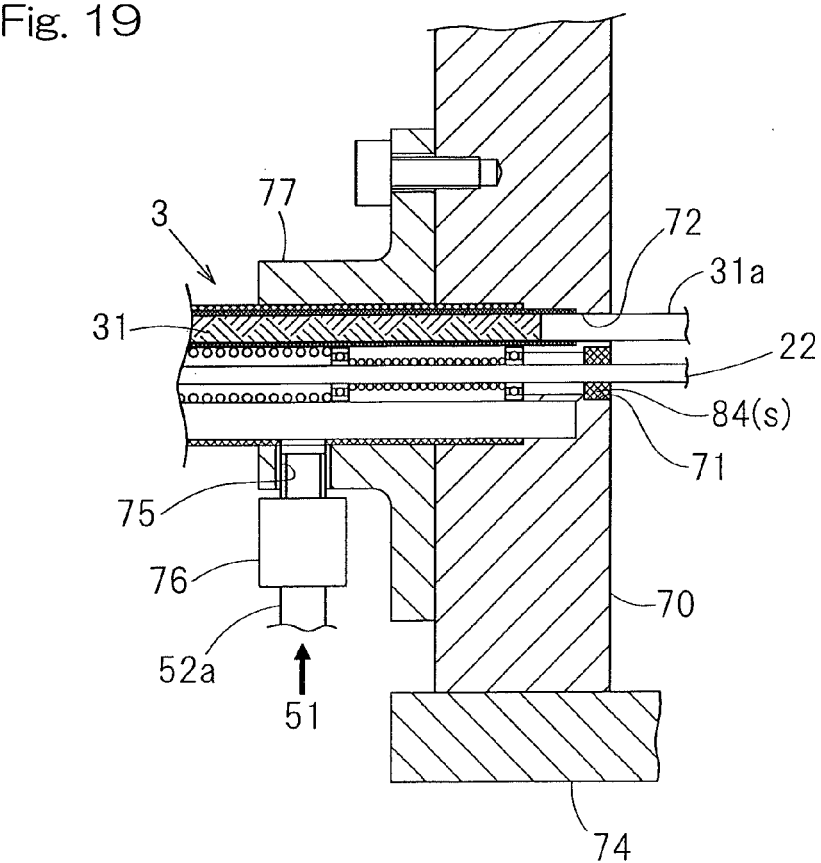
FIG. 19 is a longitudinal sectional view showing the connection area between the spindle guide section and the drive unit housing, both employed in the remote controlled actuator according to a second applied case of the present invention.

Although in the first applied case discussed above, the base end portion of the spindle guide section 3, which is inserted into the inside of the side plate 70 of the drive unit housing 4a, is provided with the coolant liquid injecting hole 75, the coolant liquid injecting hole 75 may be provided at a site exposed from the side plate 70 of the spindle guide section 3. In such case, in order to avoid the possibility that fitting of the outer passage portion 52a of the coolant liquid supply passage 52 relative to the coolant liquid injecting hole 75 may become instable, it is recommended that a root portion of the spindle guide section 3 may be fixed to the side plate 70 by the utilization of a flanged member 77, with the coolant liquid injecting hole 75 defined in such flanged member 77 as shown in FIG. 19 in connection with the second applied case.

Figure 20:
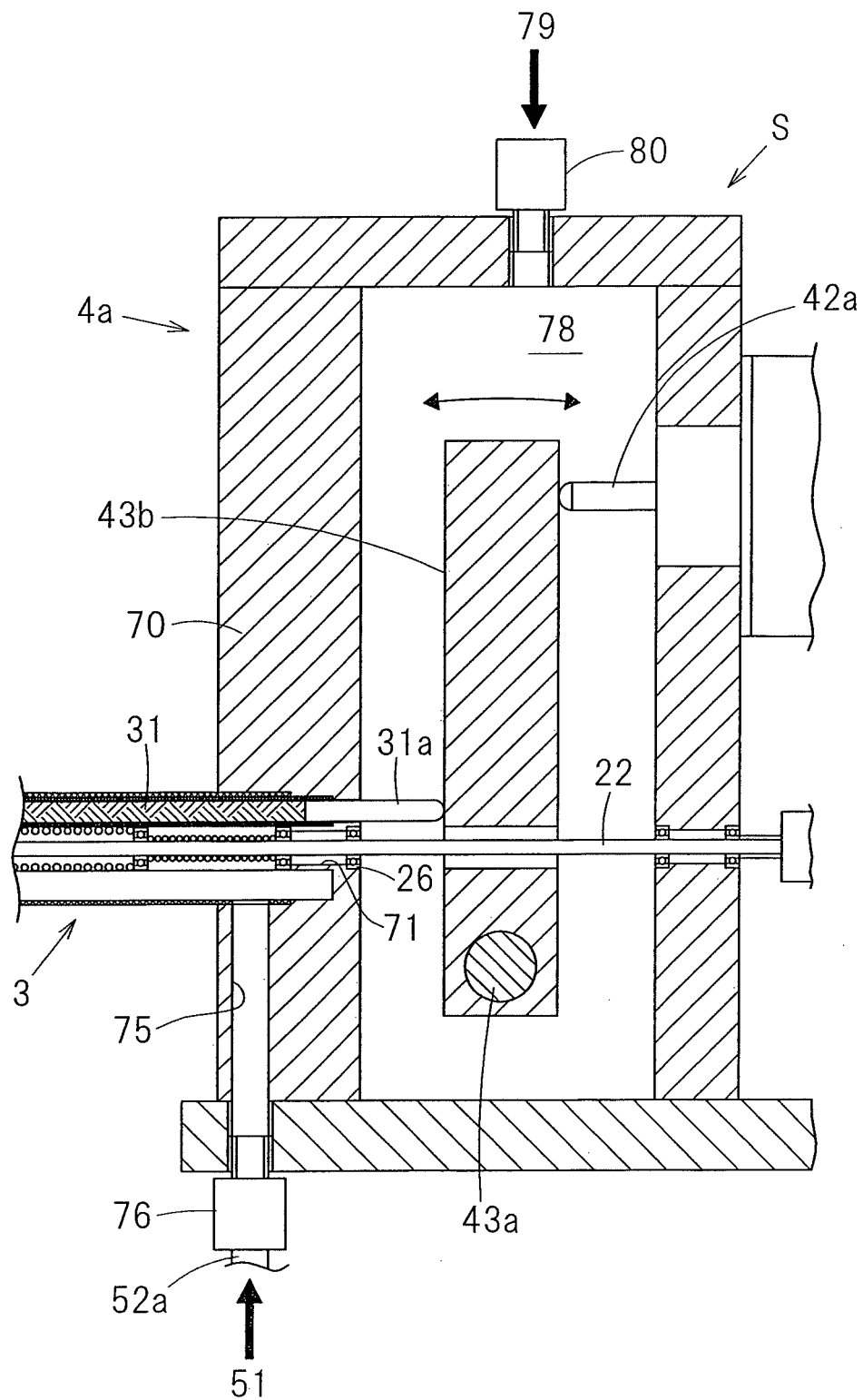
FIG. 20 is a longitudinal sectional view of the spindle guide section and a portion of the drive unit housing, showing another structure of a sealing unit.

FIG. 20 illustrates the sealing unit S of a different structure. This sealing unit S shown in FIG. 20 is of a structure, in which the drive unit housing 4a is provided with a shielded chamber 78 communicated with the inside of the spindle guide section 3 through the bearing mounting hole 71, which chamber 78 is connected by means of a tube coupling 80 with an external pressure generating device 79 so that the pressure inside the shielded chamber 78 may be caused by the pressure generating device 79 to be higher than the atmospheric pressure. For the pressure generating device 79, a pneumatic pump, for example, can be employed. A bearing engaged within the bearing mounting hole 71 for supporting the rotary shaft 22 is rendered to be a rolling bearing 26.

According to the sealing unit S of the structure described above, since the pressure at a coolant liquid discharge portion of the distal end member 2 is equal to the atmospheric pressure, to render the pressure inside the shielded chamber 78 to be higher than the atmospheric pressure allows the coolant liquid within the spindle guide section 3 to flow towards the side of the distal end member 2 and, accordingly, an undesirable ingress of the coolant liquid within the spindle guide section 3 to flow into the drive unit housing 4a can be avoided. It is to be noted that if the shielded chamber 78 can be completely sealed, that is, can be held in a condition with no air leakage taking place absolutely, the pressure generating device 79 need not be employed.

Figure 21:
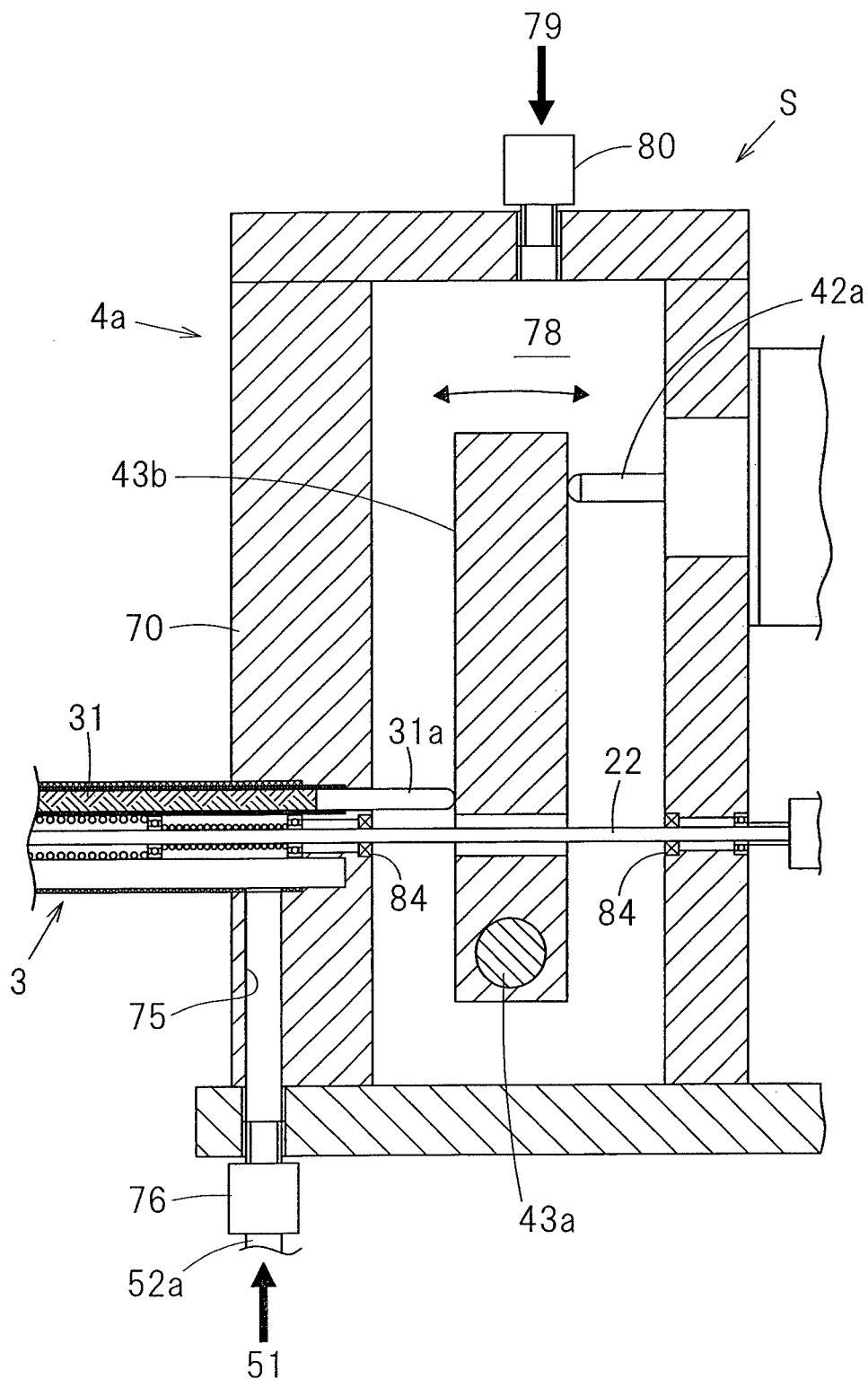
FIG. 21 is a longitudinal sectional view of the spindle guide section and a portion of the drive unit housing, showing a different structure of a sealing unit.

If the bearing for supporting the rotary shaft 22 at both sides of the shielded chamber 78 is employed in the form of a slide bearing 84 as shown in FIG. 21, the pressure inside the shielded chamber 78 can be easily increased and, therefore, the undesirable ingress of the coolant liquid from the spindle guide section 3 into the drive unit housing 4a can be avoided further effectively.

Figure 22A:
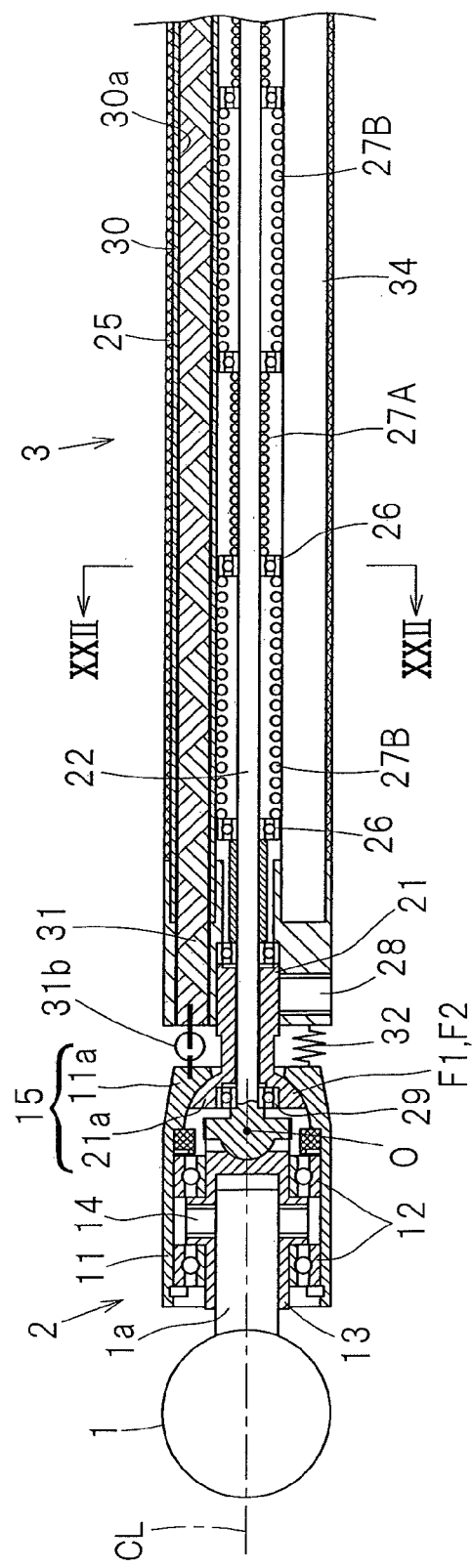
FIG. 22A is a longitudinal sectional view showing the distal end member and the spindle guide section, both employed in the remote controlled actuator according to a third applied case of the present invention.
Figure 22C:
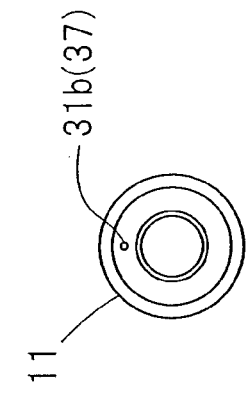
FIG. 22C is a view as viewed from the base end side of the housing for the distal end member.
Figure 22B:
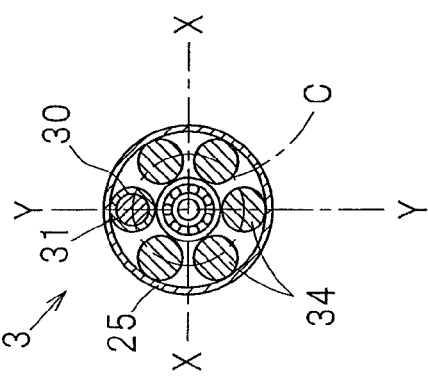
FIG. 22B is a cross sectional view taken along the line XXII-XXII in FIG. 22A.

While in the applied case discussed above, the attitude of the distal end member 2 has been shown and described to be altered as the attitude altering member 31 presses the housing 11, arrangement may be made as shown in FIGS. 22A to 22C in connection with the third applied case of the present invention, corresponding to the fourth embodiment in FIGS. 7A to 7C, that the tip end of the attitude altering member 31 in the form of a wire is connected with the housing 11 by means of a connecting member 31b so that the attitude altering member 31 can pull the housing 11 to cause the distal end member 2 to alter in attitude when the attitude altering member 31 is retracted by the attitude altering drive source (not shown) towards a base end side.

Figure 24A:
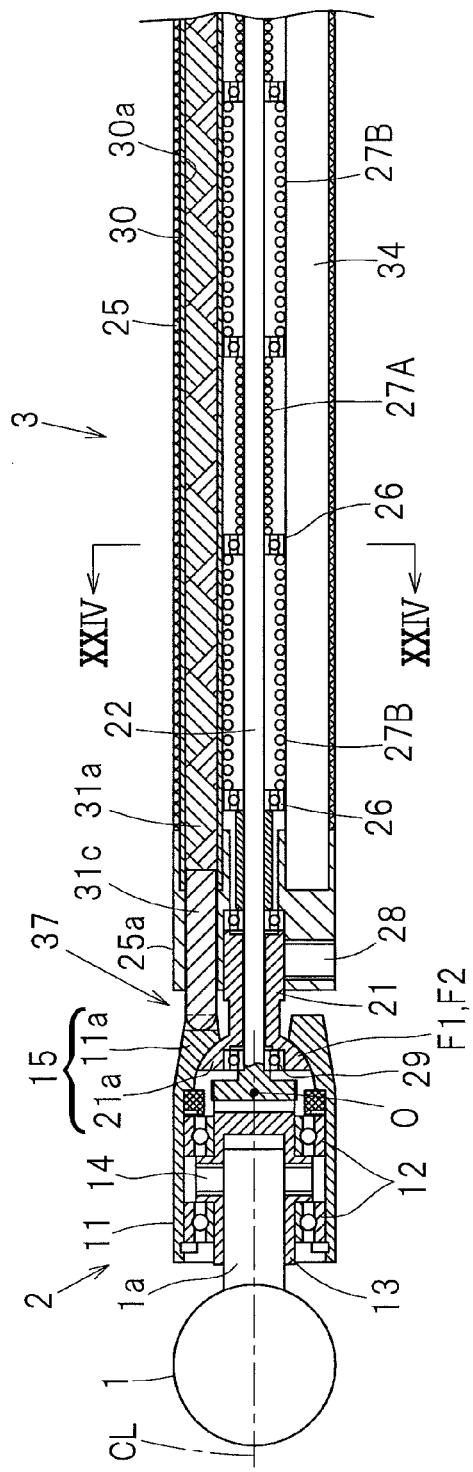
FIG. 24A is a longitudinal sectional view showing the distal end member and the spindle guide section, both employed in the remote controlled actuator according to a fifth applied case of the present invention.
Figure 24C:
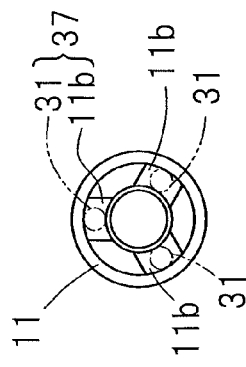
FIG. 24C is a view as viewed from the base end side of the housing for the distal end member.
Figure 24B:
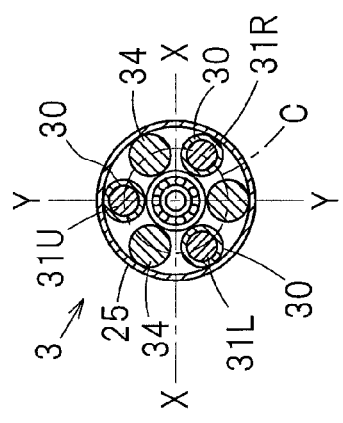
FIG. 24B is a cross sectional view taken along the line XXIV-XXIV in FIG. 24A.
Figure 26A:
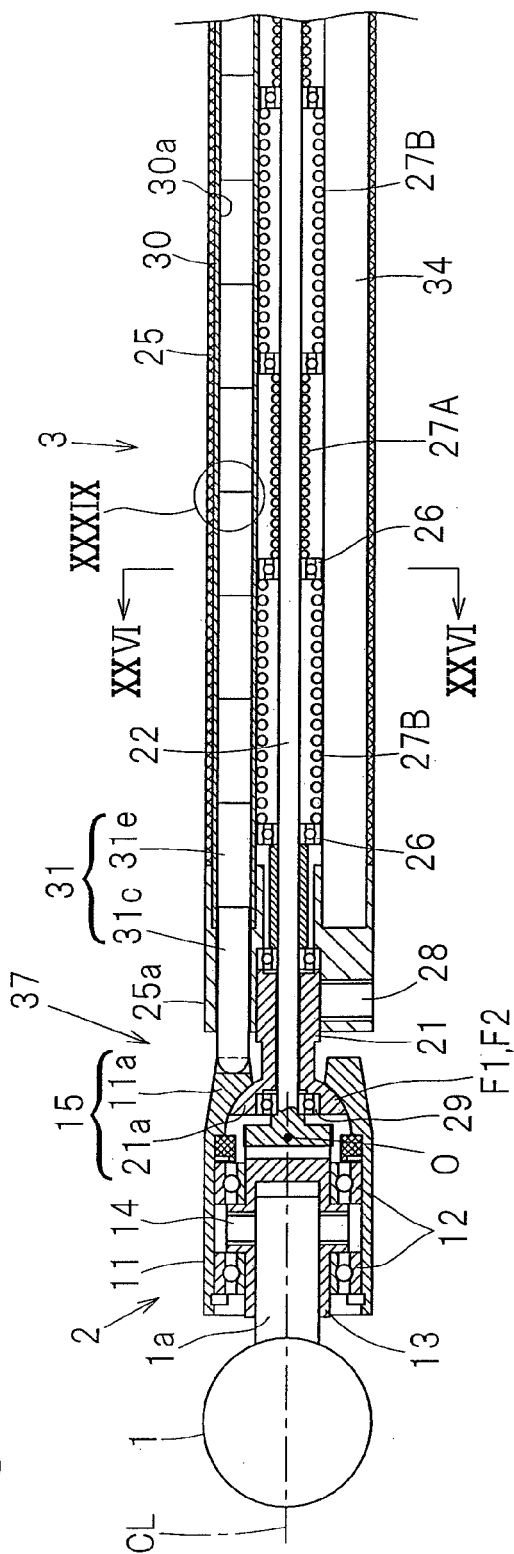
FIG. 26A is a longitudinal sectional view showing the distal end member and the spindle guide section, both employed in the remote controlled actuator according to a seventh applied case of the present invention.
Figure 26C:
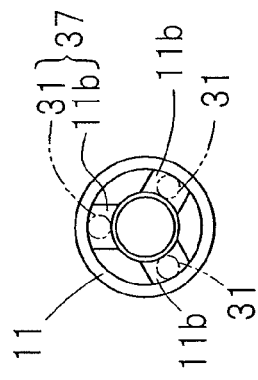
FIG. 26C is a view as viewed from the base end side of the housing for the distal end member.
Figure 26B:
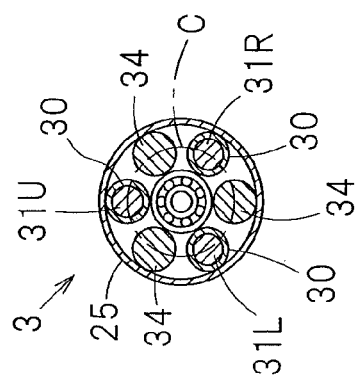
FIG. 26B is a cross sectional view taken along the line XXVI-XXVI in FIG. 26A.

FIGS. 23A to 23C illustrate the fourth applied case of the present invention and FIGS. 24A to 24C illustrate the fifth applied case of the present invention. The remote controlled actuator according to the fourth applied case corresponds to that according to the fifth preferred embodiment of the present invention shown in and described with particular reference to FIGS. 8A to 8C whereas the remote controlled actuator according to the fifth applied case corresponds to that according to the sixth preferred embodiment of the present invention shown in and described with reference to FIGS. 9A to 9C. While in the first applied case the attitude altering member 31 has been shown and described as provided at one location, the attitude altering member 31 may be provided at two locations or three locations as shown in the fourth and fifth applied cases, respectively.

The attitude altering member 31 may be constituted by a plurality of force transmitting members 31d or 31e arranged in a row extending parallel to the lengthwise direction of the guide hole 30a with no gap formed between the neighboring force transmitting members 31d or 31e as shown in FIGS. 25A to 25C or FIGS. 26A to 26C in correction with the sixth or seventh applied cases of the present invention, which corresponds to the seventh or eighth preferred embodiment of the present invention shown in and described with reference to FIGS. 10A to 10C or FIG. 11A to 11C, respectively.

FIGS. 27A to 27C illustrate a ninth preferred embodiment of the present invention, in which the outer shell pipe 25 has a different sectional shape. This embodiment corresponds to the sixth embodiment shown in and described with reference to FIGS. 9A to 9C and, therefore, component parts employed in FIGS. 27A to 27C, but similar to those shown in FIGS. 9A to 9C are shown by like reference numerals employed in FIGS. 9A to 9C.

Figure 28:
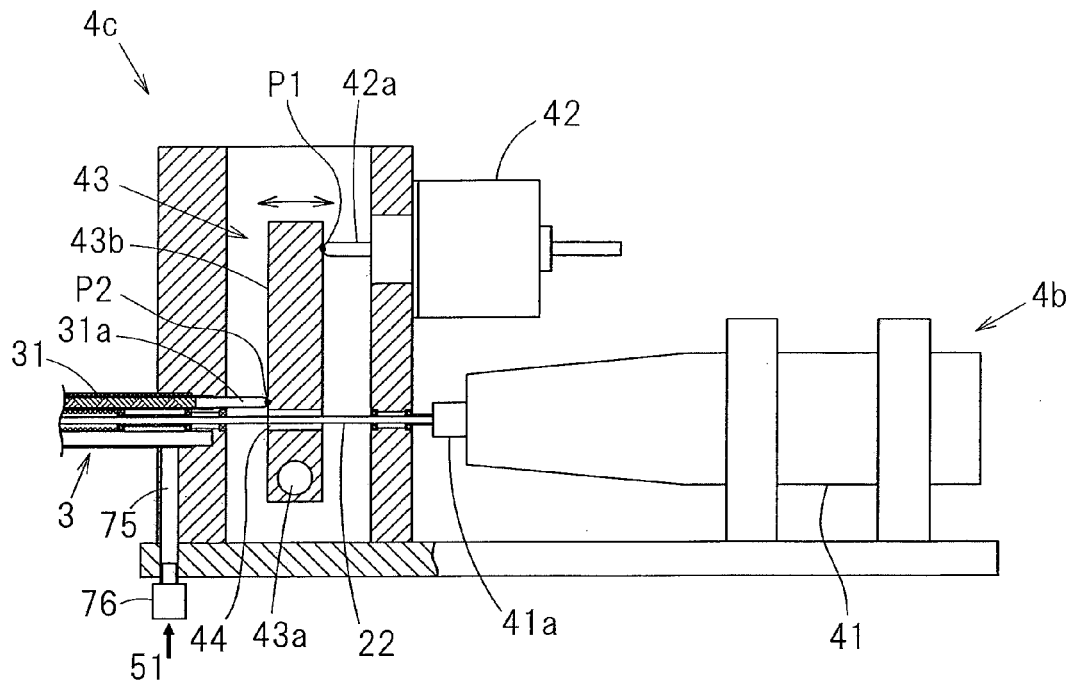
FIG. 28 is a side view showing the tool rotating drive mechanism and the attitude altering drive mechanism, both employed in each of the remote controlled actuators shown respectively in FIGS. 24A to 24C to FIGS. 27A to 27C.

In the case of this ninth embodiment, since the guide pipes 30 are arranged in the grooved portions 24b, positioning of the guide pipe 30 in the circumferential direction can be facilitated and a good assemblability can be appreciated. Also, since there is a site of a thick walled portion at a location of the outer shell pipe 25 other than the grooved portions 24b, the coolant liquid injecting hole 75 can be provided in the spindle guide section 3 with no need to using any other reinforcement member such as, for example, the flanged member 77 referred to previously if the site of the thick walled portion is opened to form the coolant liquid injecting hole 75.

Where the attitude altering member 31 is provided at three circumferential locations such as in any one of the fifth to seventh applied cases and the ninth preferred embodiment of the present invention, shown in and described with reference to FIGS. 24A to 24C to FIGS. 27A to 27C, the attitude altering drive mechanism 4c can be structured as shown in FIG. 28, which corresponds to, for example, FIG. 3A. The description made with reference to FIG. 3A can be equally applied to FIG. 28 and, therefore, the details of the attitude altering drive mechanism 4c shown in FIG. 28 will not be reiterated for the sake of brevity.

Figure 29:
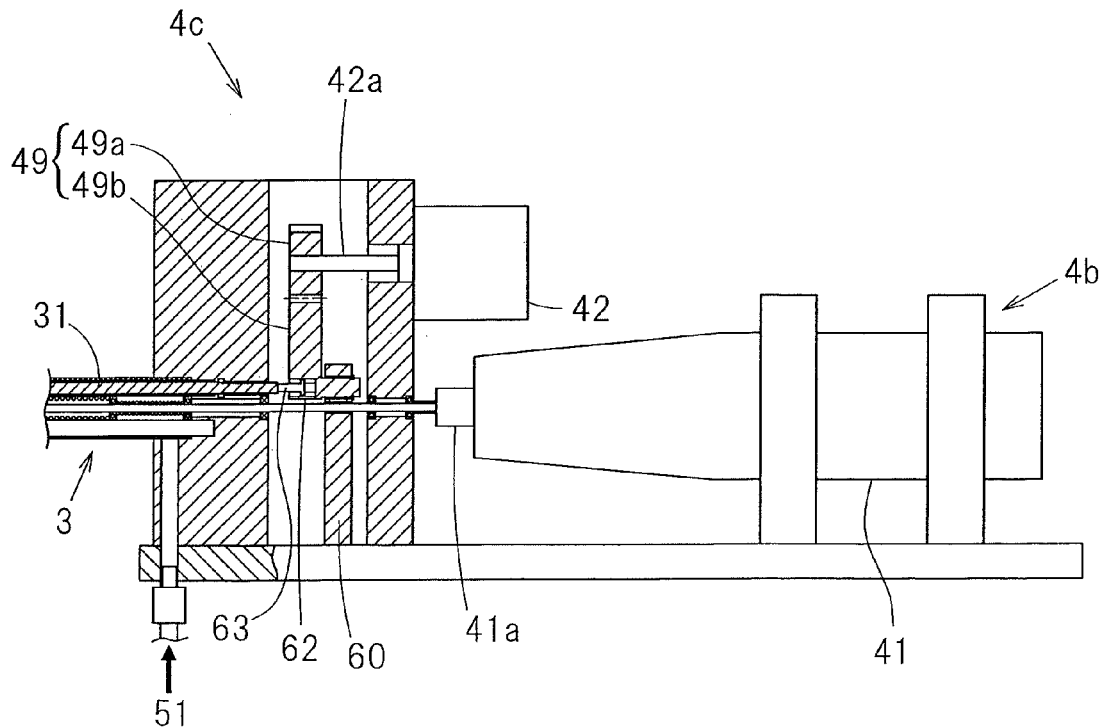
FIG. 29 is a side view showing the tool rotating drive mechanism and the attitude altering drive mechanism, both employed in the remote controlled actuator of a type employing the attitude altering drive mechanism of a different structure.
Figure 30:
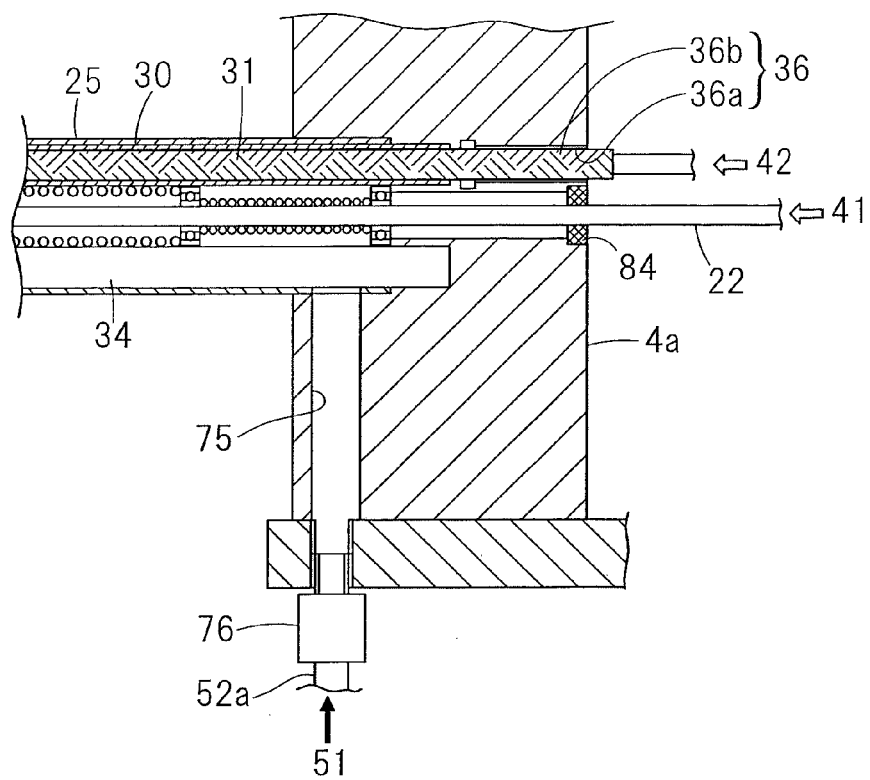
FIG. 30 is a longitudinal sectional view showing the connection area between the attitude altering member and the drive unit housing, both employed in the remote controlled actuator.

FIG. 29 illustrates a side view with a portion cutout showing the tool rotating drive mechanism 4b and the attitude altering drive mechanism 4c both employed in an embodiment in which the attitude altering drive mechanism 4c of a different structure is employed, and FIG. 30 is an enlarged view showing the connecting unit between the attitude altering member 31 and the drive unit housing 4a. FIG. 29 corresponds to FIG. 13 and FIG. 30 corresponds to FIG. 14 and structural features shown in FIGS. 29 and 30, excluding the coolant liquid supply device 51 forming the cooling unit 50, are similar to those shown in and described with reference to FIGS. 13 and 14 and, therefore, the details thereof are not reiterated for the sake of brevity.

Figure 31:
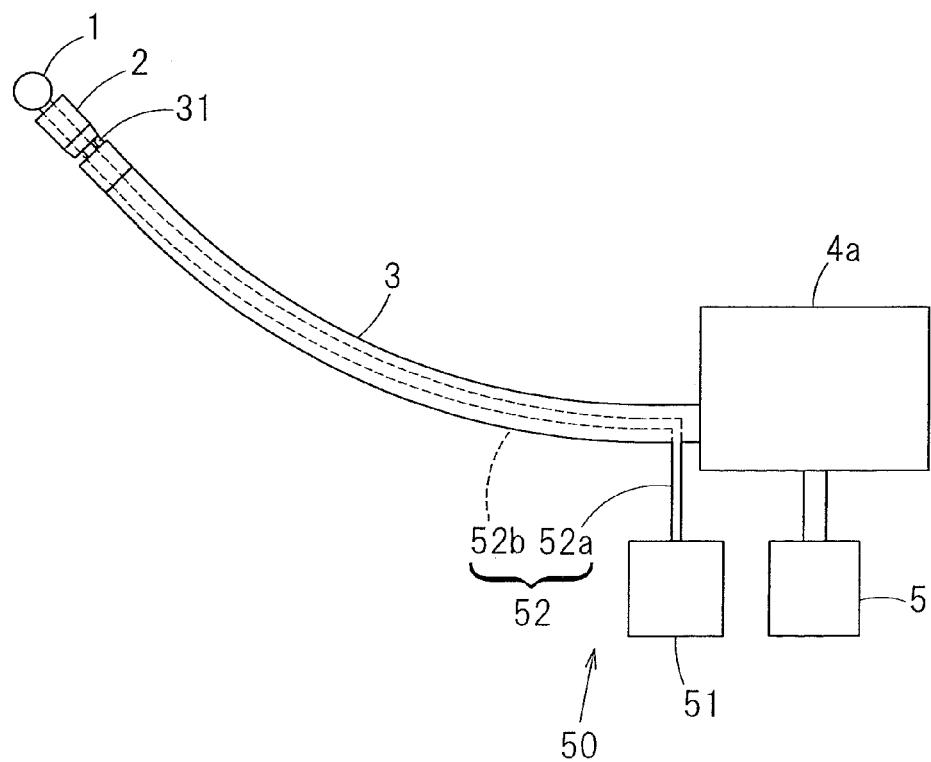
FIG. 31 is a diagram showing a schematic structure of the remote controlled actuator of a type employing the spindle guide section of a different shape.

Also, even in each of the first to seventh applied cases and the ninth embodiment of the present invention, the spindle guide section 3 in the initial condition may have a curved shape, as shown in FIG. 31, in a manner similar to that shown in FIG. 15 pertaining to the first to eighth embodiments of the present invention. Alternatively, only a portion of the spindle guide section 3 may have a curved shape.

Where the spindle guide section 3 is so designed and so configured as to have a curved shape, the outer shell pipe 25, the guide pipe 30 and the reinforcement shafts 34 are equally required to have a curved shape. Also, the use of an easily deformable material is desirable as a material for the rotary shaft 22 and, for this purpose, a shape memory alloy can be suitably employed therefor.

It is to be noted that the cooling unit 50 which has been described in connection with each of the first to seventh applied cases and the ninth embodiment of the present invention, that is, the cooling unit 50 of the structure, which has an interior, into which a coolant liquid is injected through a coolant liquid injecting hole 75 defined in the vicinity of the base end of the spindle guide section 3, and which is capable of feeding it towards the tip end side through the interiors of the spindle guide section 3 and the distal end member 2 and finally discharging it from the distal end member 2 towards the tool 1, can be introduced in place of the cooling unit 50 employed in the practice of the first embodiment of the present invention shown in and described with particular reference to FIG. 4.

Hereinafter, an eighth applied case of the present invention, in which the remote controlled actuator is not provided with the hollow 24 having the round hole portion 24a and the grooved portions 24b, will now be described with particular reference to FIGS. 32A to 32D and FIG. 33.

This eights applied case makes use of a friction reducing unit disposed between an inner surface of the guide hole 30a and the attitude altering member 31 for reducing a frictional force developed between the inner surface of the guide hole 30a and the attitude altering member 31. It is to be noted that in this applied case, component parts similar to those employed in any one of the previously described embodiments are designated by like reference numerals and, therefore, the details thereof are not reiterated for the sake of brevity.

Figure 33:
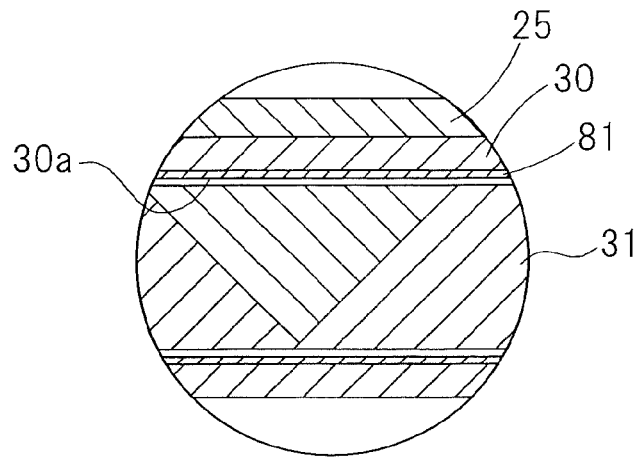
FIG. 33 is a diagram showing, on an enlarged scale, a portion indicated by XXXIII in FIG. 32A.

As shown in FIG. 33 which illustrates, on an enlarged scale, a portion indicated by XXXIII in FIG. 32A, the guide hole 30a has an inner surface provided with a coating layer 81 as a friction reducing unit for reducing the frictional force developed between the inner surface of the guide hole 30a and the attitude altering member 31. This coating layer 81 is made of a material such as, for example, a resin.

In addition, since the coating layer 81 is provided in the inner surface of the guide hole 30a as a friction reducing unit, the frictional force developed between the inner surface of the guide hole 30a and the attitude altering member 31 can be reduced. Accordingly, a force applied from the attitude altering drive source 42 to the attitude altering member 31 is smoothly transmitted to the distal end member 2 to allow the attitude of the distal end member 2 to be altered accurately. Also, even though the spindle guide section 3 is curved, the force applied to the attitude altering member 31 can be accurately transmitted to the distal end member 2 to allow the attitude of the distal end member 2 to be accomplished accurately. Yet, since the frictional force is thus reduced, the attitude altering drive source 42 can be compactized and the amount of an electric power consumed can be reduced.

Figure 34:
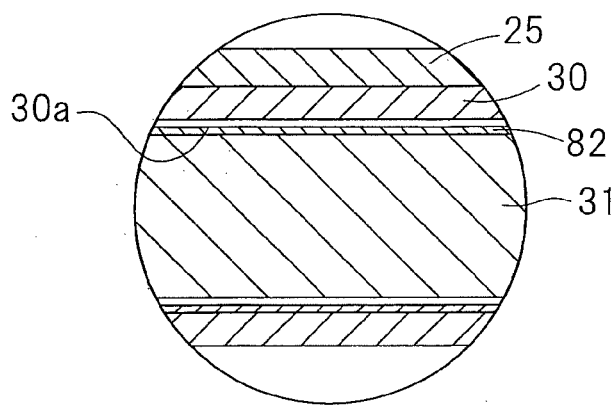
FIG. 34 is a diagram showing a sectional portion of the remote controlled actuator of a type employing a friction reducing unit of a structure different from that shown in FIG. 33.

Although in the eighth applied case discussed above the coating layer 81 as the friction reducing unit is provided in the inner surface of the guide hole 30a (as best shown in FIG. 33), a coating layer 82 may be provided in a surface of the attitude altering member 31 as a friction reducing unit as shown in FIG. 34. In such case, the coating layer 82 is operable to reduce the frictional force developed between it and the guide pipe 30 opposed thereto.

Figure 35:
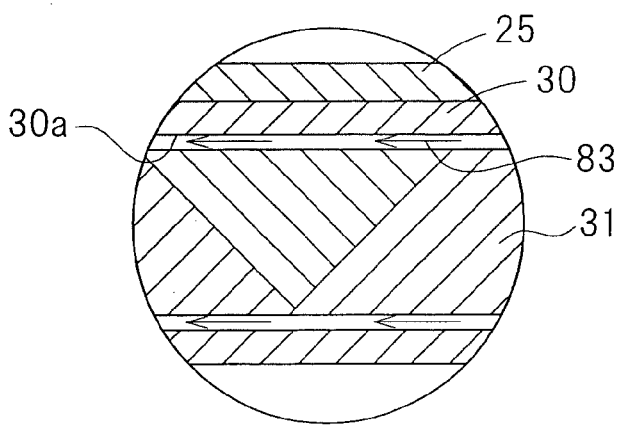
FIG. 35 is a diagram showing that sectional portion of the remote controlled actuator of a type employing the friction reducing unit of a structure different from those shown in FIGS. 33 and 34.

Also, as shown in FIG. 35, a liquid 83 for lubrication may exist within the guide hole 30a as a friction reducing unit. In such case, the liquid 83 for lubrication is employed, which is of a kind capable of reducing the frictional force developed between the guide pipe 30 and the attitude altering member 31 when existing between the inner surface of the guide hole 30a and the attitude altering member 31. For the liquid 83 for lubrication, water or physiological saline can be suitably employed. If water or physiological saline is employed, the liquid 83 for lubrication will not bring about any influence on the living body in the event that the remote controlled actuator of the present invention is for use in medical application and the processing is performed with the distal end member 2 inserted into the living body.

Even in the respective remote controlled actuators according to third, fourth and fifth applied cases of the present invention shown in FIGS. 22A to 22C, FIGS. 23A to 23C and FIGS. 24A to 24C, the friction reducing unit shown in and described with reference to each of FIGS. 33, 34 and 35 can be provided between the inner surface of the guide hole 30a and the attitude altering member 31. Accordingly, effects similar to those described previously can be equally obtained.

Figure 36:
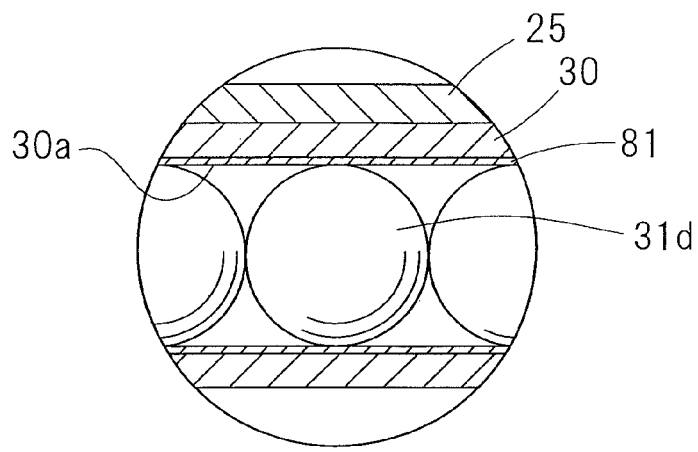
FIG. 36 is a diagram showing, on a large scale, a portion indicated by XXXVI in FIG. 25A.
Figure 37:
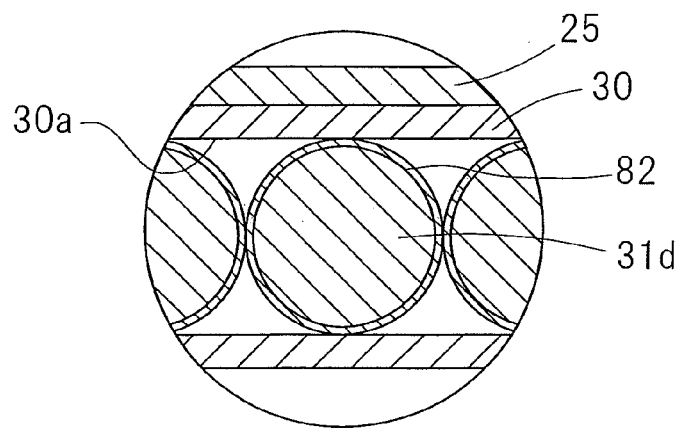
FIG. 37 is a diagram showing a sectional portion of the remote controlled actuator of a type employing a friction reducing unit of a structure different from that shown in FIG. 36.
Figure 38:
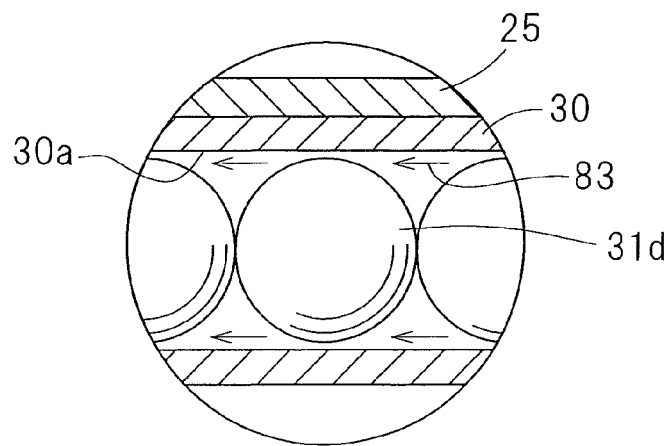
FIG. 38 is a diagram showing that sectional portion of the remote controlled actuator of a type employing the friction reducing unit of a structure different from those shown in FIGS. 36 and 37.
Figure 39:
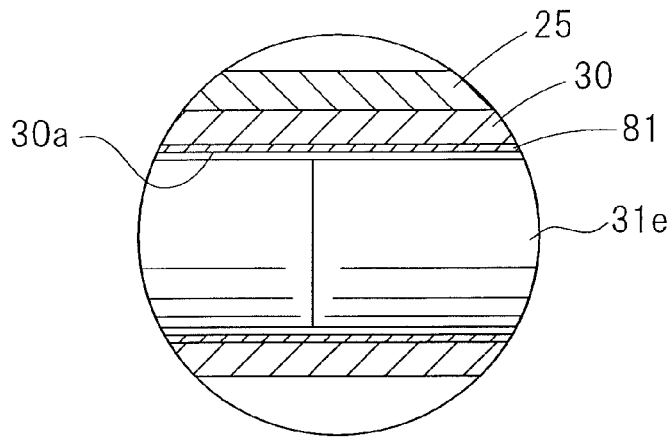
FIG. 39 is a diagram showing, on a large scale, a portion indicated by XXXIX-XXXIX in FIG. 26A.
Figure 40:
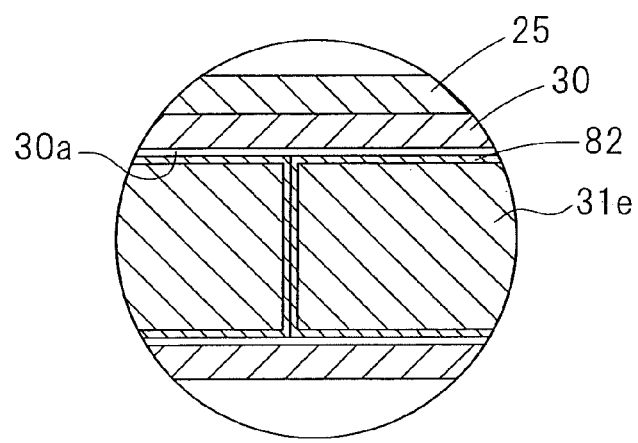
FIG. 40 is a diagram showing a sectional portion of the remote controlled actuator of a type employing a friction reducing unit of a structure different from that shown in FIG. 39.
Figure 41:
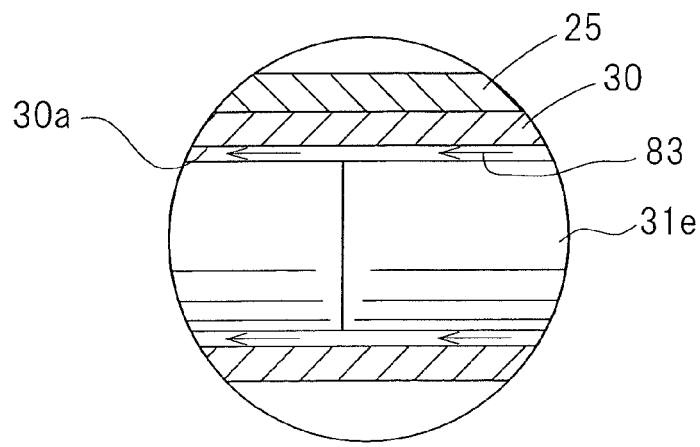
FIG. 41 is a diagram showing a sectional portion of the remote controlled actuator of a type employing a friction reducing unit of a structure different from those shown in FIGS. 39 and 40.

In the case of the sixth applied case shown in FIGS. 25A to 25C, the friction reducing unit shown in each of FIGS. 36, 37 and 38 can be provided between the inner surface of the guide hole 30a and the attitude altering member 31. Also, in the case of the seventh applied case shown in FIGS. 26A to 26C, the friction reducing unit shown in each of FIGS. 39, 40 and 41 is provided between the inner surface of the guide hole 30a and the attitude altering member 31. FIGS. 36 and 39 illustrate the coating layer 81 provided in the inner surface of the guide hole 30a. FIGS. 37 and 40 illustrate the coating layer 82 provided in the surface of the force transmitting members 31d or 31e forming the attitude altering member 31. FIGS. 38 and 41 illustrate the liquid 83 for lubrication existing within the guide hole 30a. The provision of such friction reducing unit as described above is effective to provide effects similar to those described previously.

It is to be noted that even in each of the previously described first to eighth embodiments of the present invention, the friction reducing unit can be provided, and, therefore, effects similar to those described in connection with the previously described eighth applied case above can be equally obtained even when the friction reducing unit is employed in each of those first to eighth embodiments.

Ninth to twelfth applied cases, in which the hollow 24 having the round hole portion 24a and the grooved portions 24b is not provided, will be described hereinafter.

In each of the ninth to twelfth applied cases, when the angle formed between the center line of the rotary shaft 22 and the line normal to the tangential line at a contact point between the distal end member 2 and the attitude altering member 31 is so chosen as to be α, the attitude of the tool 1 fitted to a tip end of an elongated pipe section can be altered by remote control and, yet, such attitude of the tool can be smoothly altered without relying on the use of any lubricant nor coating, provided that the angle α is under specific conditions. It is to be noted that in each of the ninth to twelfth applied cases, component parts similar to those employed in any one of the foregoing embodiments are designated by like reference numerals and, therefore, the details thereof are not reiterated for the sake of brevity.

The ninth applied case will now be described in detail with particular reference to FIGS. 42A to 42C.

Referring to FIG. 42A, the base end face 11c of the housing 11 represents an inclined face with an outer diametric portion thereof closer to the side of the spindle guide section 3 and the attitude altering member 31 and, when the angle formed between the center line CL2 of the rotary shaft 22 and the perpendicular line PL normal to the tangential line at the point of contact P between the distal end member 2 and the attitude altering member 31 is chosen to be α, the angle α is rendered to be larger than 0° at all times. In this applied case, the base end face 11c of the housing 11 has a sectional shape representing a rectilinear shape. If the base end face 11c represents a plane and does not intersect the center line of the attitude altering member 31, the relation of α>0° is always maintained. If the sectional shape of the base end face 11c is rectilinear, processing is relatively easy to accomplish and, therefore, the cost of manufacture can be reduced. The tip end of the pillar shaped pin 31c on the side of the drive unit housing 4a is spherical, too, and is held in engagement with a side face of the lever 43b (FIGS. 3A and 3B) described above. The attitude altering member 31 may be constituted solely by a single wire 31a with the pillar shaped pin 31c dispensed with.

The operation of the remote controlled actuator of the structure according to the ninth applied case is basically similar to that of the remote controlled actuator according to any one of the previously described embodiments of the present invention and, therefore, the details thereof are not reiterated for the sake of brevity, but particularly in the case of this ninth applied case, the attitude altering member 31 is positioned at a location offset from the center line CL2 of the rotary shaft 22 such that the attitude altering member 31 selectively advance or retract in a direction parallel to the center line CL2 of the rotary shaft 22 while the tip end thereof is kept in contact with the base end face 11*c* of the housing 11 for the distal end member 2. As the tip end of the attitude altering member 31 pushes the base end face 11*c* of the housing 11, which is a contact surface of the distal end member 2, the distal end member 2 swings accompanied by alteration in attitude thereof. If at this time, the base end face 11*c* of the housing 11 lies perpendicular to the direction of advance or retraction of the attitude altering member 31, that is, the angle α formed between the center line CL2 of the rotary shaft 22 and the perpendicular line PL normal to the tangential line at the point of contact P of the distal end member 2 with the attitude altering member 31 is 0°, no slip occurs between the distal end member 2 and the attitude altering member 31 and, therefore, the distal end member 2 is unable to swing. However, if the angle α is greater than 0°, that is, α>0°, the distal end member 2 can slide to swing, having overcome the friction developed between the distal end member 2 and the attitude altering member 31 and, also, the friction acting on the distal end member connecting unit 15 and, therefore, the attitude of the distal end member 2 can be smoothly altered. For this reason, neither the lubricant nor the coating is needed.

Figure 43:
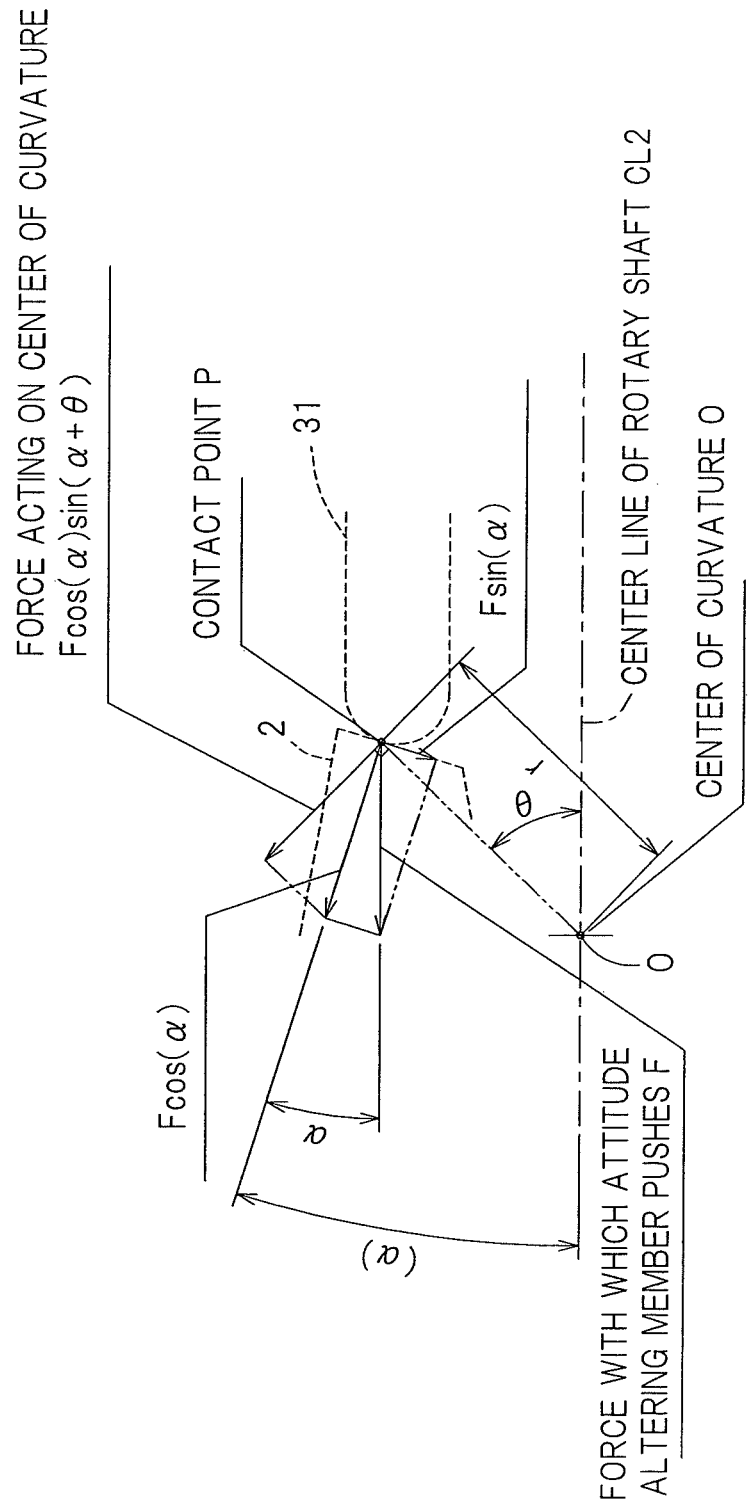
FIG. 43 is an explanatory diagram showing a force acting on a point of contact between the distal end member and the attitude altering member.

FIG. 43 illustrates an explanatory diagram showing the force acting on the point of contact P of the distal end member 2 with the attitude altering member 31. Assuming that the force necessary for the attitude altering member 31 to push the distal end member 2 is expressed by F and the coefficient of static friction at the contact area between the distal end member 2 and the attitude member 31 is expressed by μ, the maximum value of the static frictional force and the force acting in the tangential direction can be expressed by μF cos (α) and F sin (α), respectively. Since when the relation, μF cos (α)<F sin (α) is established, slippage occurs at the point of contact P between the distal end member 2 and the attitude altering member 31, the attitude of the distal end member 2 can be altered if the coefficient of static friction μ is smaller than tan(α), that is, μ<tan (α). The value of the angle α at which the distal end member 2 can be altered in attitude can be determined if the coefficient of static friction μ is measured beforehand. By way of example, if the coefficient of static force μ is 0.3, the angle α is larger than 16.7°, that is, α>16.7°. In general, the static frictional force is larger than the kinetic frictional force. Accordingly, if the operation can take place having overcome the static frictional force, such operation can overcome the kinetic frictional force as well. Since the coefficient of static friction μ is of a value intermediate between 0 and 1, that is, 0<μ<1, the foregoing relation (μF cos (α)<F sin (α)) can be applied to all frictional surfaces.

Also, if the angle formed between the center line CL2 of the rotary shaft 22 and the line drawn to connect between the center of curvature O of the guide faces F1 and F2 and the contact point P is chosen to be θ and the distance between the center of curvature O and the contact point P is chosen to be r, the torque of a magnitude expressed by rF cos (α) sin (α+θ) acts around the center of curvature O. This torque becomes large as (α+θ) approaches 90°. In the case other than θ=90°, the torque of 0°<α<45° is larger than the torque of α=0°.

In the case of the angle α equal to or greater than 45°, when the force applied by the attitude altering member 31 to the distal end member 2 is divided into an axially acting force and a radially acting force, the radially acting force is so larger than the axially acting force that no drive force can be sufficiently transmitted to the distal end member 2. Also, when the radially acting force becomes large, the frictional force developed between the attitude altering member 31 and the inner surface of the guide hole 30*a* of the guide pipe 30, which is a guide face of the attitude altering member 31, becomes large, requiring a large drive force. Accordingly, for the purpose of calculation, it is desirable that the angle α is within the range of 0° to 45°, that is, 0°<α<45°. In practice, the coefficient of static friction μ seldom exceeds the value of 0.7 and, therefore, selection of the angle α within the range of 0° to 35° is sufficient.

Figure 44A:
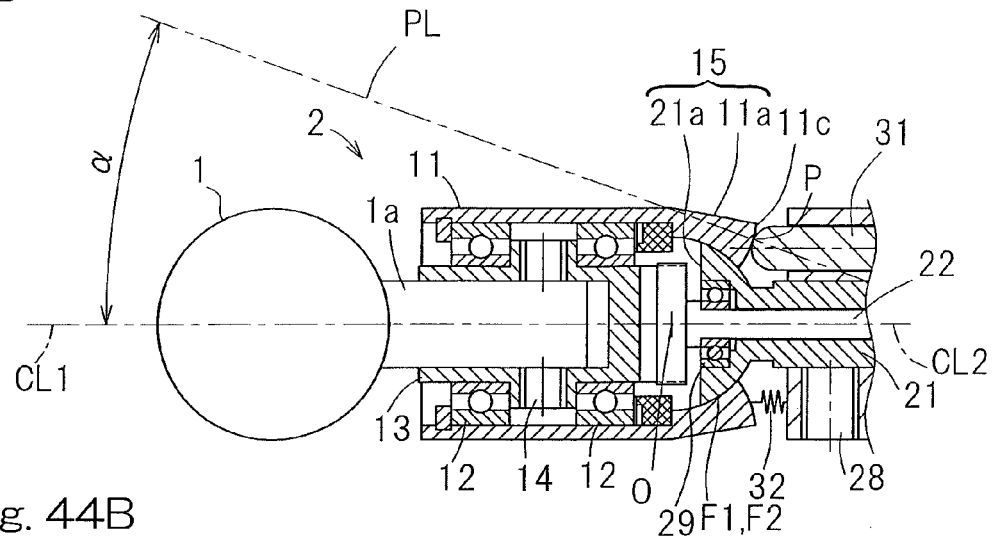
FIG. 44A is a fragmentary sectional view of the remote controlled actuator of a type, in which the distal end member has a contact face of a different shape, showing the distal end member assuming an attitude.
Figure 44B:
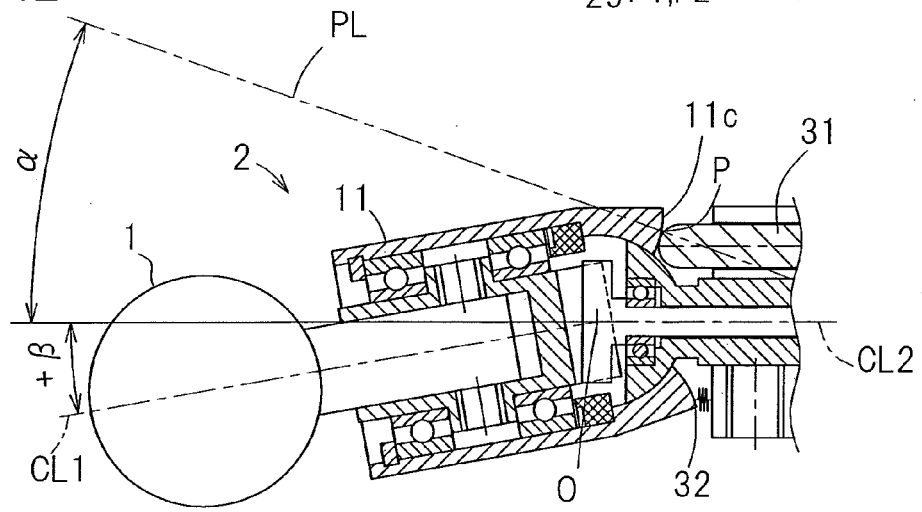
FIG. 44B is a fragmentary sectional view of the remote controlled actuator of a type, in which the distal end member has a different attitude.
Figure 44C:
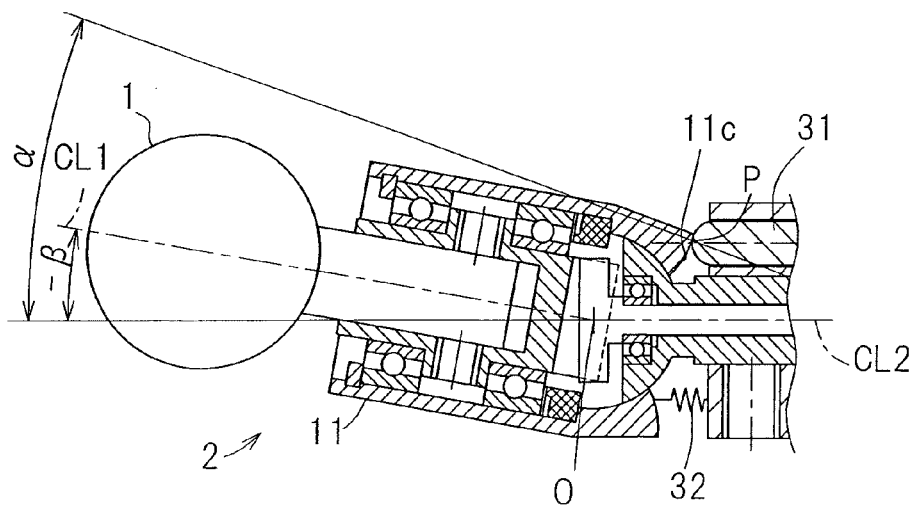
FIG. 44C is a fragmentary sectional view of the remote controlled actuator of a type, in which the distal end member has a further different attitude.

The sectional shape of the base end face 11*c* of the housing 11, which is the surface of the distal end member 2 that contacts the attitude altering member 31, may be an arcuate shape protruding towards the attitude altering member side as shown in FIGS. 44A to 44C. In such case, unless the center of the arcuate shape lies on the center line of the attitude altering member 31, the relation of α>0° is maintained at all times. With the sectional shape of the base end face 11*c* so chosen as to be an arcuate shape as described above, even when the distal end member 2 assumes any attitude as shown in FIGS. 44A, 44B and 44C, the design can be made so that the angle α may almost assume a constant value. FIG. 44A illustrates the condition in which the swinging angle β of the distal end member 2 is 0°, FIG. 44B illustrates the condition in which the swinging angle β thereof is 10°, and FIG. 44C illustrates the condition in which the swinging angle β thereof is −10°. In any of those conditions, the angle α is almost constant. For this reason, regardless of the attitude of the distal end member 2, a smooth movement of the distal end member 2 can be realized.

Figure 45A:
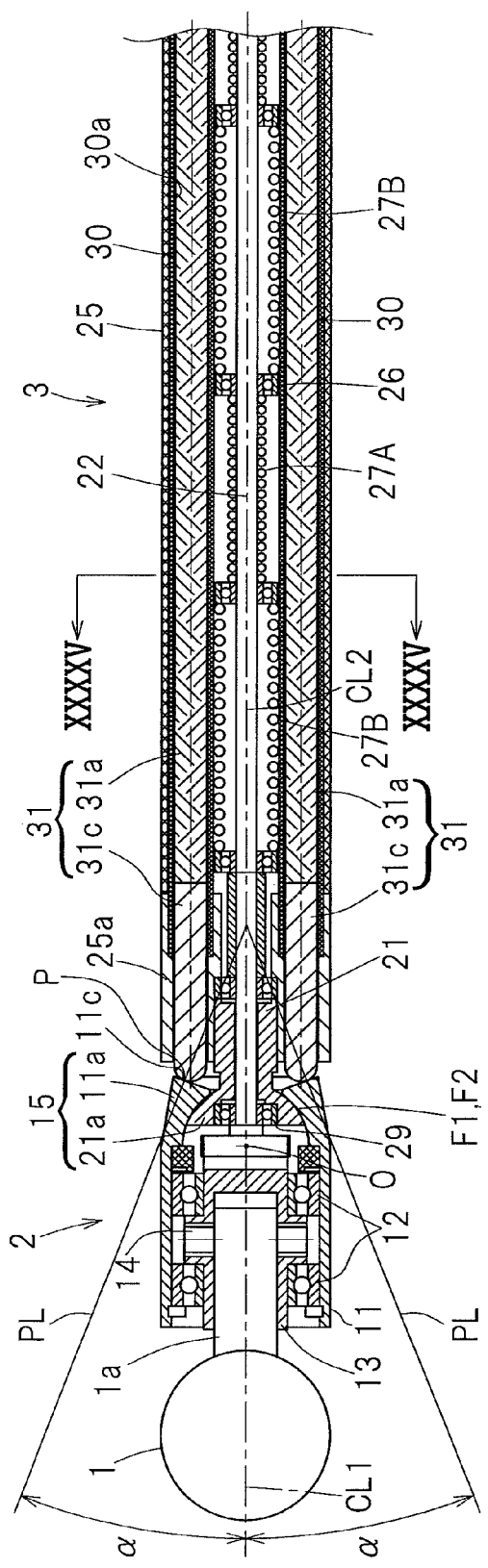
FIG. 45A is a longitudinal sectional view showing the distal end member and the spindle guide section, both employed in the remote controlled actuator according to a tenth applied case of the present invention.
Figure 45B:
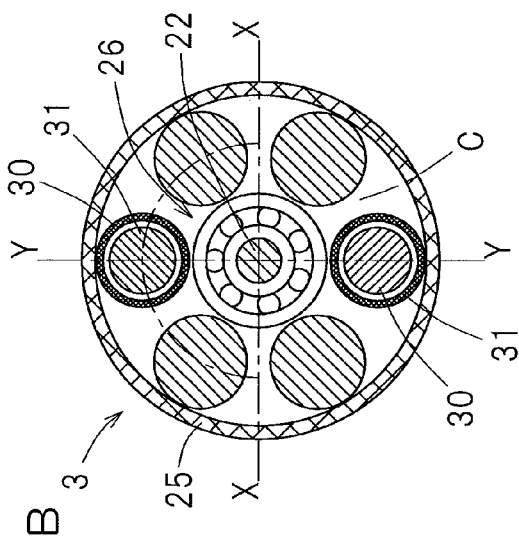
FIG. 45B is a cross sectional view taken along the line XXXXV-XXXXV in FIG. 45A.

FIGS. 45A and 45B illustrate a tenth applied case. The remote controlled actuator according to this tenth applied case is such that two guide pipes 30 are provided within the outer shell pipe 25 and positioned at respective circumferential locations spaced 180° in phase from each other and the attitude altering member 31 similar to that described previously is reciprocally movably inserted within the guide hole 30*a*, which is an inner diametric hole of each of the guide pipes 30. Between the two guide pipes 30, a plurality of reinforcement shafts 34 are arranged on the same pitch circle diameter C as that of the guide pipes 30. No restoring elastic member 32 is employed. The guide faces F1 and F2 are each a spherical face having a center of curvature at the point O or a cylindrical face having a longitudinal axis represented by an X-axis passing across the point O. This tenth applied case corresponds to the fifth embodiment of the present invention shown in and described with particular reference to FIGS. 8A to 8C and, therefore, further details thereof are not reiterated for the sake of brevity.

Figures 46A, 46B:
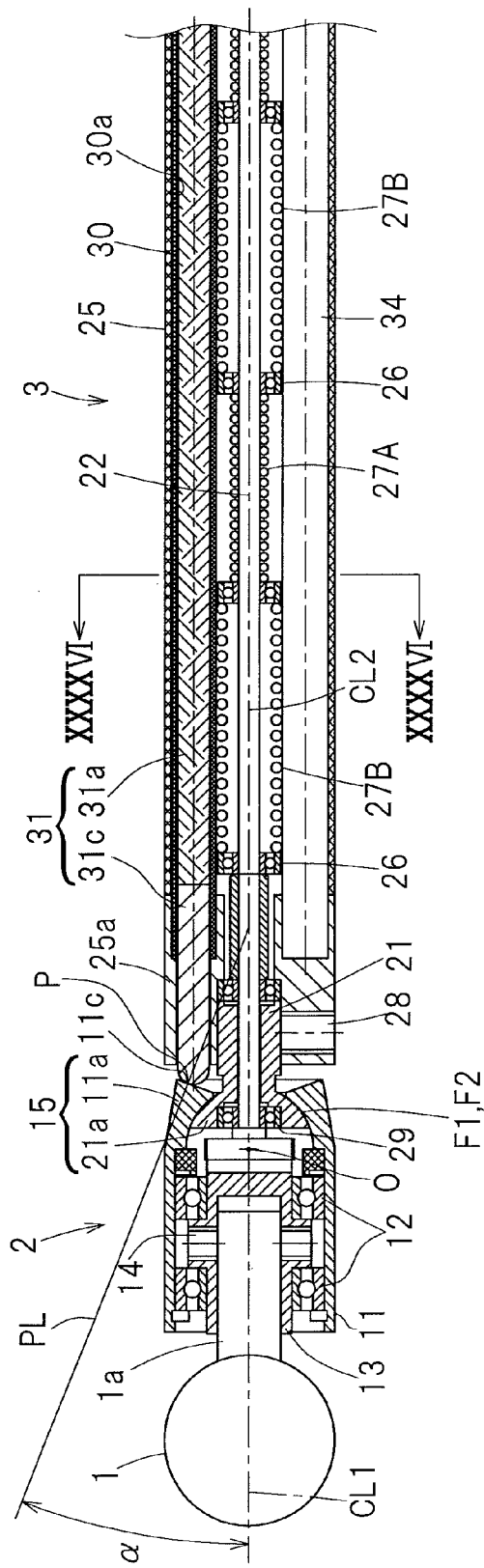
FIG. 46A is a longitudinal sectional view showing the distal end member and the spindle guide section, both employed in the remote controlled actuator according to an eleventh applied case of the present invention.
FIG. 46B is a cross sectional view taken along the line XXXXVI-XXXXVI in FIG. 46A.

FIGS. 46A and 46B illustrate an eleventh applied case. The remote controlled actuator according to this eleventh applied case is such that three guide pipes 30 are provided within the outer shell pipe 25 and positioned at respective circumferential locations spaced 120° in phase from each other and the attitude altering member 31 similar to that described previously is reciprocally movably inserted within the guide hole 30*a*, which is an inner diametric hole of each of the guide pipes 30. Between those three guide pipes 30, a plurality of reinforcement shafts 34 are arranged on the same pitch circle diameter C as that of the guide pipes 30. No restoring elastic member 32 is employed. The guide faces F1 and F2 are each a spherical face having a center of curvature at the point O and the distal end member 2 can be tilted in any arbitrary direction. This eleventh applied case corresponds to the sixth embodiment of the present invention shown in and described with particular reference to FIGS. 9A to 9C and, therefore, further details thereof are not reiterated for the sake of brevity.

Figure 47A:
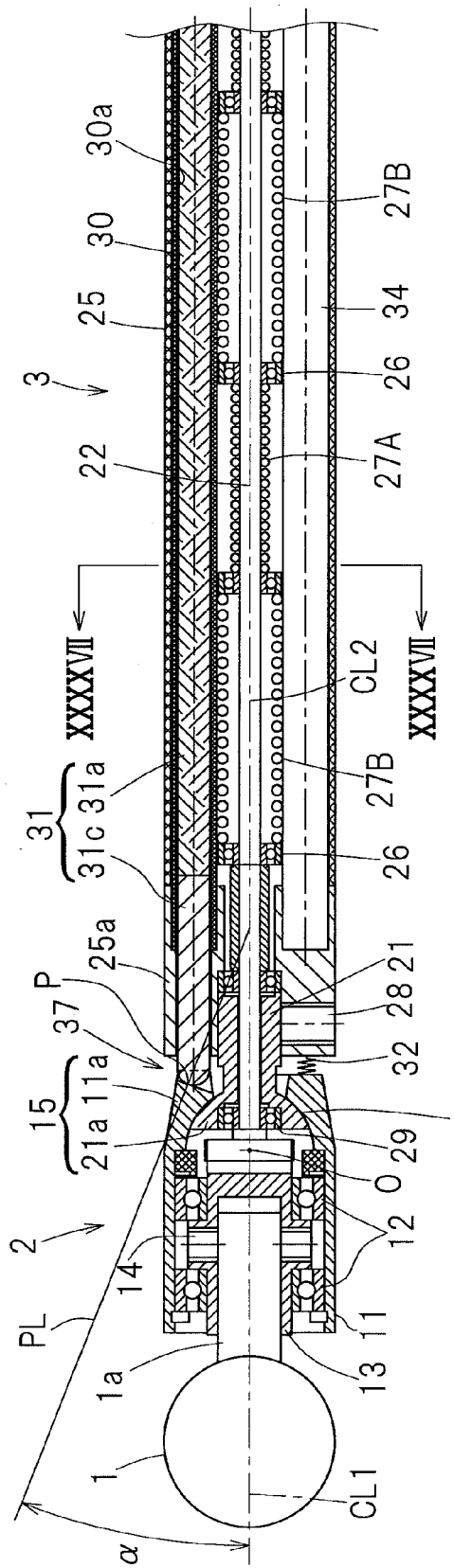
FIG. 47A is a longitudinal sectional view showing the distal end member and the spindle guide section, both employed in the remote controlled actuator according to a twelfth applied case of the present invention.
Figure 47C:
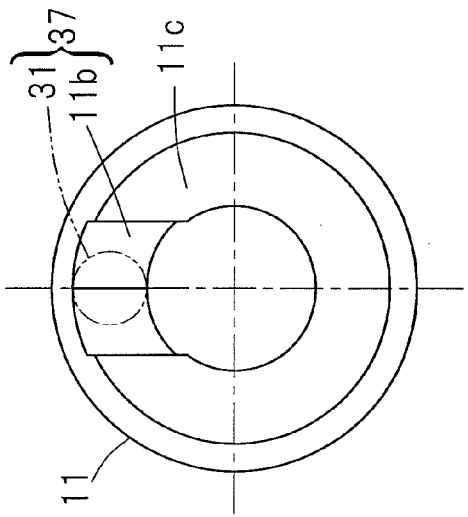
FIG. 47C is a view as viewed from the base end side of the housing for the distal end member.
Figure 47B:
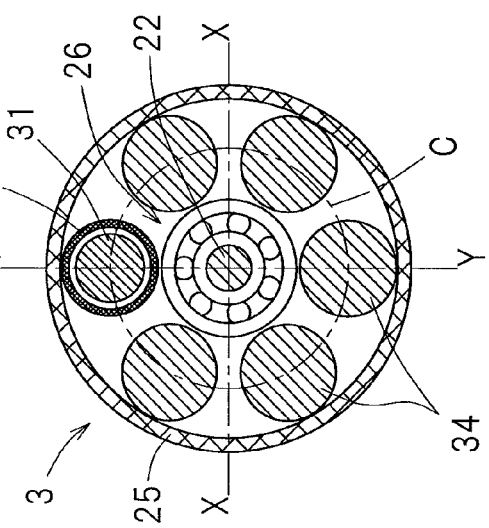
FIG. 47B is a cross sectional view taken along the line XXXXVII-XXXXVII in FIG. 47A.

FIGS. 47A to 47C illustrate a twelfth applied case. The remote controlled actuator according to this twelfth applied case is such that the base end face 11c (FIG. 47C) of the housing 11 for the distal end member 2 is formed with a radial groove portion 11b (as best shown in FIG. 47C) and the spherical tip end of the attitude altering member 31 is held in contact with a bottom face of the radial groove portion 11b. This radial groove 11b cooperates with the attitude altering member 31 to form a rotation preventing mechanism 37 and, accordingly, when the tip end portion of the attitude altering member 31, then inserted into the radial groove 11b, contacts a side face of the radial groove 11b, the distal end member 2 can be prevented from rotating about the center line CL1 of the spindle 13 relative to the spindle guide section 3. This twelfth applied case corresponds to the first embodiment of the present invention shown in and described with particular reference to FIGS. 2A to 2C and, therefore, further details thereof are not reiterated for the sake of brevity.

FIGS. 48A and 48B illustrate a tenth preferred embodiment of the present invention. The remote controlled actuator according to this tenth embodiment makes use of the spindle guide section 3 of a type, in which the hollow 24 of the outer shell pipe 25 has a round hole portion 24a at the center thereof and three grooved portions 24b depressed radially outwardly from respective circumferential locations on the outer periphery of the round hole portion 24a, which are spaced 120° in phase from each other in the circumferential direction. A peripheral wall at a tip end of each of the grooved portions 24b represents a semicircular sectional shape. The rotary shaft 22 and the rolling bearing 26 are accommodated within the round hole portion 24a and the attitude altering member 31 is accommodated within each of the grooved portions 24b.

Although this tenth embodiment of the present invention has been shown and described as having the attitude altering member 31 provided at the three circumferential locations spaced 120° in phase form each other, the present invention equally applies to the use of the attitude altering member 31 at two circumferential locations spaced 180° in phase from each other and also to the use of a combination of the attitude altering member 31, provided at one circumferential location, with the corresponding restoring elastic member 32. By way of example, in the structure having the attitude altering member 31 provided at one circumferential location, arrangement may be made that as is the case with the outer shell pipe 25 shown in and described with reference to FIGS. 48A and 48B, the grooved portion 24b of the hollow 24 is provided at three circumferential location and one of those grooved portions 24b is used to accommodate therein the attitude altering member 31 while the remaining two grooved portions 24b are used to accommodate therein the reinforcement shafts 34 (See, for example, FIGS. 2A to 2C).

In any one of each of the foregoing embodiments and the various applied cases, the use has been shown and described of the rotation preventing mechanism 37 for the distal end member 2, but the use of the rotation preventing mechanism 37 may not be essential and may therefore be dispensed with.

Also, even where the guide pipe 30 and the attitude altering member 31 are each provided at a plurality of circumferential locations, the outer shell pipe 25 and each of the guide pipes 30 may be fixed by means of the pipe fixture segment 65. Accordingly, the rigidity of the spindle guide section 3 can be further increased.

Although the spindle guide section 3 employed in the tenth embodiment described above and each of the eighth to twelfth applied cases has been shown and described as having a rectilinear shape, the remote controlled actuator of the present invention is such that the attitude altering member 31 has a flexibility and even when the spindle guide section 3 is in a curved condition, the alteration of the attitude of the distal end member 2 can be assuredly accomplished and, therefore, the spindle guide section 3 may have a curved shape in its initial condition as shown in FIG. 15 and FIG. 31. Alternatively, only a portion of the spindle guide section 3 may have a curved shape. If the spindle guide section 3 has a curved shape, it may occur that insertion of the distal end member 2 deep into the bore, where the spindle guide section of the rectilinear shape fails to reach, can be accomplished, and, therefore, the processing of the opening for insertion of the artificial joint prior to a surgery being performed to replace with the artificial joint can be formed precisely and accurately.

Where the spindle guide section 3 is designed to represent the curved shape, the outer shell pipe 25, the guide pipes 30 and the reinforcement shafts 34 need be similarly curved in shape. Also, an easily deformable material is preferably used for the rotary shaft 22 and a shape memory alloy, for example, can be suitably employed therefor.

Although the present invention has been fully described as applied to the remote controlled actuator for medical use, the present invention can be equally applied to the remote controlled actuator for any other use than the medical use. By way of example, if it is designed for use in machine processing, drilling to form a curved hole and cutting at a site deep into the groove can be accomplished.

Some modes will be hereinafter described in detail, in which the hollow 24 having the round hole portion 24a and the grooved portions 24b, which is essential in the practice of any one of the foregoing embodiments of the present invention hereinbefore fully described, is not required.

[Mode 1]

The remote controlled actuator according to the first mode 1 includes a spindle guide section of an elongated configuration, a distal end member fitted to a tip end of the spindle guide section through a distal end member connecting unit for alteration in attitude, and a drive unit housing to which a base end of the spindle guide section is connected;

in which the distal end member rotatably supports a spindle for holding a tool and the spindle guide section includes a rotary shaft for transmitting rotation of a tool rotating drive source, provided within the drive unit housing, to the spindle, a guide hole so as to extend to opposite ends thereof, and attitude altering members reciprocally movably inserted within the guide pipe for altering the attitude of the distal end member;

in which the attitude altering members are, while a tip end thereof is held in contact with the distal end member, selectively advanced or retracted one at a time;

in which an attitude altering drive source for selectively advancing or retracting the or each attitude altering member is provided within the drive unit housing; and in which a cooling unit is provided, which has an interior, into which a coolant liquid is injected through a coolant liquid injecting hole defined in the vicinity of a base end of the spindle guide section, and capable of feeding it towards the tip end side through the interiors of the spindle guide section and the distal end member and finally discharging it from the distal end member towards the tool, and a sealing unit is also provided for avoiding an ingress of the coolant liquid from the inside of the spindle guide section into the drive unit housing.

[Mode 2]

In the mode 1 described above, a plurality of rolling bearings are provided for rotatably supporting the rotary shaft within the spindle guide section and a spring element for applying a preload to those rolling bearings are provided between the neighboring rolling bearings.

[Mode 3]

In the mode 1 described above, the coolant liquid is water or physiological saline.

[Mode 4]

The remote controlled actuator according to the mode 4 includes a spindle guide section of an elongated configuration, a distal end member fitted to a tip end of the spindle guide section through a distal end member connecting unit for alteration in attitude, and a drive unit housing to which a base end of the spindle guide section is connected;

in which the distal end member rotatably supports a spindle for holding a tool and the spindle guide section includes a rotary shaft for transmitting rotation of a tool rotating drive source, provided within the drive unit housing, to the spindle, a guide hole so as to extend to opposite ends thereof, and flexible attitude altering members reciprocally movably inserted within the guide pipe for altering the attitude of the distal end member;

in which the attitude altering members are, while a tip end thereof is held in contact with the distal end member, selectively advanced or retracted one at a time;

in which an attitude altering drive source for selectively advancing or retracting the or each attitude altering member is provided within the drive unit housing; and in which a friction reducing unit is provided between an inner surface of the guide hole and the attitude altering member for reducing a frictional force developed therebetween.

[Mode 5]

In the mode 4 described above, an actuation amount detector is provided for detecting the amount of actuation of the attitude altering drive source and an attitude detector is also provided for detecting the attitude of the distal end member from a detection value of the actuation amount detector.

[Mode 6]

In the mode 4 described above, a plurality of rolling bearings are provided for rotatably supporting the rotary shaft within the spindle guide section and a spring element for applying a preload to those rolling bearings are provided between the neighboring rolling bearings.

[Mode 7]

The remote controlled actuator according to the mode 7 includes a spindle guide section of an elongated configuration, a distal end member fitted to a tip end of the spindle guide section through a distal end member connecting unit for alteration in attitude, and a drive unit housing to which a base end of the spindle guide section is connected;

in which the distal end member rotatably supports a spindle for holding a tool and the spindle guide section includes a rotary shaft for transmitting rotation of a tool rotating drive source, provided within the drive unit housing, to the spindle, a guide hole so as to extend to opposite ends thereof, and attitude altering members reciprocally movably inserted within the guide pipe for altering the attitude of the distal end member;

in which the attitude altering members are, while a tip end thereof is held in contact with the distal end member, selectively advanced or retracted one at a time;

in which an attitude altering drive source for selectively advancing or retracting the or each attitude altering member is provided within the drive unit housing; and in which when the angle formed between a center line of the rotary shaft and a perpendicular line normal to the tangential line at a point of contact between the distal end member and the attitude altering member is expressed by $\alpha$, the angle $\alpha$ is greater than 0°, that is, $\alpha > 0°$.

[Mode 8]

In the mode 7 described above, the distal end member includes a tubular housing, the spindle arranged in an inner periphery of the housing and a bearing for supporting the spindle for rotation relative to the housing, such that when the attitude of the distal end member is held in a neutral condition, it assumes a position on a center line of the spindle and a line of extension of the center line of the rotary shaft and the attitude altering member assumes a position offset from the center line of the rotary shaft with its tip end capable of selectively advancing or retracting in a direction parallel to the center line of the rotary shaft in a fashion contacting an end face of the housing for the distal end member, the end face of the housing being rendered to be an inclined face having its outer diametric side closer to the side of the attitude altering member.

[Mode 9]

In the mode 7 described above, when the coefficient of static friction at the contact area between the distal end member and the attitude altering member is expressed by $\mu$, the relation of $\mu < \tan(a)$ establishes between the coefficient of static friction $\mu$ and the angle $\alpha$.

[Mode 10]

In the mode 7 described above, the surface of the distal end member that contacts the attitude altering member has a sectional shape representing a rectilinear shape.

[Mode 11]

In the mode 7 described above, the surface of the distal end member that contacts the attitude altering member has a sectional shape that is an arcuate shape enough to protrude on the side of the attitude altering member.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1: Tool
2: Distal end member
3: Spindle guide section
4a: Drive unit housing
5: Controller
13: Spindle
15: Distal end member connecting unit
22: Rotary shaft
24: Hollow
24a: Round hole portion
24b: Grooved portion
25: Outer shell pipe
26, 29: Rolling bearing
27A, 27B: Spring element
30: Guide pipe
30a: Guide hole
32: Restoring elastic member
34: Reinforcement shaft 41: Tool rotating drive source
42: Attitude altering drive source
50: Cooling unit
65: Pipe fixture unit
66: Opening
67: Solder or weld deposit
68: Laser weld deposit
75: Coolant liquid injecting hole
78: Shielded chamber
81: Coating layer in the guide pipe (Friction reducing means)
82: Coating layer in the attitude altering member (Friction Reducing Means)
83: Liquid for lubrication (Friction reducing means)
84: Slide bearing
CL1: Center line of the spindle
CL2: Center line of the rotary shaft
P: Point of contact
PL: Perpendicular line
S: Sealing unit

What is claimed is:

1. A remote controlled actuator which comprises a spindle guide section of an elongated configuration, a distal end member fitted to a tip end of the spindle guide section through a distal end member connecting unit for alteration in attitude, and a drive unit housing to which a base end of the spindle guide section is connected;
in which the distal end member rotatably supports a spindle for holding a tool;
in which the spindle guide section includes a hollow outer shell pipe forming an outer shell for the spindle guide section, a rotary shaft provided within a hollow of the outer shell pipe, which hollow extends to opposite ends of the outer shell pipe, for transmitting rotation of a tool rotating drive source, provided within the drive unit housing, to the spindle, a guide pipe provided within the hollow and having a guide hole so as to extend to opposite ends thereof, and one or a plurality of attitude altering members reciprocally movably inserted within the guide pipe for altering the attitude of the distal end member;
in which one or a plurality of attitude altering members is, while a tip end thereof is held in contact with the distal end member, selectively advanced or retracted one at a time;
in which an attitude altering drive source for selectively advancing or retracting the or each attitude altering member is provided within the drive unit housing; and
in which the hollow has a round hole portion at a center and a grooved portion depressed radially outwardly from the round hole portion, and the rotary shaft is arranged within the round hole portion whereas the guide pipe is arranged within the grooved portion.

2. The remote controlled actuator as claimed in claim 1, in which the geometric moment of inertia of the outer shell pipe is of a value equal to or larger than ½ of a solid shaft of the same outer diameter.

3. The remote controlled actuator as claimed in claim 1, in which the or each attitude altering member comprises a plurality of force transmitting members arranged in a row extending in a direction along a lengthwise direction of the guide pipe, or a wire extending in a direction along the lengthwise direction of the guide pipe.

4. The remote controlled actuator as claimed in claim 1, in which the guide pipe and the attitude altering member inserted within the guide pipe are each provided at two or three locations, and the attitude altering drive source is provided for each of the attitude altering members so that the attitude of the distal member can be altered and maintained in dependence on the balance of respective working forces of the attitude altering members at the two or three locations acting on the distal end member.

5. The remote controlled actuator as claimed in claim 1, further comprising a rolling bearing for rotatably supporting the rotary shaft within the spindle guide section, the rolling bearing having an outer diametric surface supported by the guide pipe.

6. The remote controlled actuator as claimed in claim 1, further comprising a cooling unit for cooling the tool with a coolant liquid flowing inside the outer shell pipe, or a coolant liquid supplied from an outside.

7. The remote controlled actuator as claimed in claim 1, in which when the angle formed between a center line of the rotary shaft and a perpendicular line normal to the tangential line at a point of contact between the distal end member and the attitude altering member is expressed by $\alpha$, the angle $\alpha$ is within the range of 0° to 45°.

8. The remote controlled actuator as claimed in claim 1, further comprising a plurality of rolling bearings for rotatably supporting the rotary shaft within the spindle guide section and a spring element for applying a preload to the rolling bearings, the spring element being provided between the neighboring rolling bearings.

9. The remote controlled actuator as claimed in claim 8, further comprising a cooling unit for cooling the bearings with a coolant liquid flowing inside the outer shell pipe.

10. The remote controlled actuator as claimed in claim 1, further comprising a cooling unit having an interior, into which a coolant liquid is injected through a coolant liquid injecting hole defined in the vicinity of a base end of the spindle guide section, and capable of feeding it towards the tip end side through the interiors of the spindle guide section and the distal end member and finally discharging it from the distal end member towards the tool; and a sealing unit for avoiding an ingress of the coolant liquid from the inside of the spindle guide section into the inside of the drive unit housing.

11. The remote controlled actuator as claimed in claim 10, in which the sealing unit comprises a slide bearing for supporting the rotary shaft at a location on the side of the base end and remote from the coolant liquid injecting hole.

12. The remote controlled actuator as claimed in claim 10, in which the sealing unit includes a shielded chamber provided in the drive unit housing and communicated with the inside of the spindle guide section at the base end of the spindle guide section, the pressure inside the shielded chamber being chosen to be higher than the atmospheric pressure.

13. The remote controlled actuator as claimed in claim 1, further comprising a friction reducing unit provided between an inner surface of the guide hole and the attitude altering member for reducing a frictional force developed therebetween.

14. The remote controlled actuator as claimed in claim 13, in which the friction reducing unit comprises a coating layer coated on at least one of the inner surface of the guide hole and a surface of the attitude altering member.

15. The remote controlled actuator as claimed in claim 13, in which the friction reducing unit comprises a liquid for lubrication existing within the guide hole.

* * * * *